(12) United States Patent
Berthelot et al.

(10) Patent No.: US 10,272,157 B2
(45) Date of Patent: Apr. 30, 2019

(54) POROUS SOLID WITH OUTER SURFACE GRAFTED WITH A POLYMER

(71) Applicants: COMMISSARIAT A L'ENERGIE ATOMIQUE ET AUX ENERGIES ALTERNATIVES (CEA), Paris (FR); CENTRE NATIONAL DE LA RECHERCHE SCIENTIFIQUE (CNRS), Paris (FR); UNIVERSITE VERSAILLES SAINT-QUENTIN-EN-YVELINES, Versailles (FR); UNIVERSITE PARIS-SUD 11, Orsay (FR)

(72) Inventors: Thomas Berthelot, Les Ulis (FR); Elena Bellido Vera, Sabadell (ES); Ruxandra Gref, Verrieres le Buisson (FR); Patricia Horcajada Cortes, Versailles (FR); Christian Serre, Plaisir (FR); Patrick Couvreur, Villebon sur Yvette (FR)

(73) Assignees: COMMISSARIAT A L'ENERGIE ATOMIQUE ET AUX ENERGIES ALTERNATIVES (CEA), Paris (FR); CENTRE NATIONAL DE LA RECHERCHE SCIENTIFIQUE (CNRS), Paris (FR); UNIVERSITE VERSAILLES SAINT-QUENTIN-EN-YVELINES, Versailles (FR); UNIVERSITE PARIS-SUD 11, Orsay (FR)

( * ) Notice: Subject to any disclaimer, the term of this patent is extended or adjusted under 35 U.S.C. 154(b) by 458 days.

(21) Appl. No.: 14/878,421

(22) Filed: Oct. 8, 2015

(65) Prior Publication Data

US 2016/0101192 A1   Apr. 14, 2016

(30) Foreign Application Priority Data

Oct. 8, 2014   (EP) .................................. 14188166

(51) Int. Cl.

| | | |
|---|---|---|
| A61K 31/522 | (2006.01) |
| A61K 8/02 | (2006.01) |
| A61K 8/81 | (2006.01) |
| A61L 31/04 | (2006.01) |
| A61K 47/48 | (2006.01) |
| C08F 220/10 | (2006.01) |
| C09D 4/00 | (2006.01) |
| C09D 133/06 | (2006.01) |
| C09J 4/00 | (2006.01) |
| C09J 133/06 | (2006.01) |
| A61L 31/16 | (2006.01) |
| C07F 15/02 | (2006.01) |
| A61Q 19/00 | (2006.01) |
| C08L 71/02 | (2006.01) |
| A61K 47/58 | (2017.01) |
| A61K 47/69 | (2017.01) |

(52) U.S. Cl.
CPC ...... *A61K 47/48869* (2013.01); *A61K 8/0279* (2013.01); *A61K 8/8152* (2013.01); *A61K 31/522* (2013.01); *A61K 47/58* (2017.08); *A61K 47/6923* (2017.08); *A61K 47/6925* (2017.08); *A61L 31/048* (2013.01); *A61L 31/16* (2013.01); *A61Q 19/00* (2013.01); *C07F 15/02* (2013.01); *C08F 220/10* (2013.01); *C08L 71/02* (2013.01); *C09D 4/00* (2013.01); *C09D 133/06* (2013.01); *C09J 4/00* (2013.01); *C09J 133/06* (2013.01); *A61K 2800/614* (2013.01)

(58) Field of Classification Search
CPC ...................................................... A61K 47/58
See application file for complete search history.

(56) References Cited

U.S. PATENT DOCUMENTS

| | | |
|---|---|---|
| 2008/0145706 A1 | 6/2008 | Mevellec et al. |
| 2008/0152949 A1 | 6/2008 | Mevellec et al. |
| 2009/0117391 A1 | 5/2009 | Mevellec et al. |
| 2010/0226991 A1 | 9/2010 | Horcajada-Cortes et al. |
| 2015/0150981 A1 | 6/2015 | Gref et al. |

FOREIGN PATENT DOCUMENTS

| | | |
|---|---|---|
| WO | 2008/078052 | 7/2008 |
| WO | 2009/077670 | 6/2009 |
| WO | 2009/077671 | 6/2009 |
| WO | 2013/178954 | 12/2013 |

*Primary Examiner* — Alma Pipic
(74) *Attorney, Agent, or Firm* — Young & Thompson

(57) ABSTRACT

A process for preparing a porous solid with an outer surface modified by at least one polymer; the polymer being simultaneously synthetized in solution and grafted on the outer surface of the solid, includes contacting:
  a porous solid; and
  a polymer-precursor solution comprising an adhesion primer, and at least one polymerizable monomer;
under conditions enabling the formation of radical entities.

7 Claims, 10 Drawing Sheets

(a)

(b)

POROUS SOLID WITH OUTER SURFACE GRAFTED WITH A POLYMER

FIELD OF INVENTION

The present invention relates to a porous solid which is preferably a crystalline porous solid, and more specifically a metal-organic framework (MOF) having modified outer surface, said outer surface being modified by the grafting of a polymer thereon. The invention further relates to a process for manufacturing the modified porous solid of the invention.

The modified porous solid of the invention may be used, for example, for carrying pharmaceutical compounds and/or used as a contrast agent. Moreover, it may be used for applications in the cosmetic field. It may also be used for vectorizing and/or monitoring pharmaceutical compounds in a living body.

BACKGROUND OF INVENTION

The use of carriers and vectors for molecules of interest, especially molecules with a therapeutic effect or markers, has become a major issue for the development of novel diagnostic methods or novel medicines. Specifically, the molecules of interest possess characteristics that influence their pharmacokinetics and biodistribution and which are not always favorable or adaptable to the medium into which they are introduced. These characteristics are, for example, physicochemical properties, such as instability (degradation, a strong tendency toward crystallization . . . ), poor water solubility and/or biological characteristics such as important protein binding, poor physiological barrier bypass, toxicity or biodegradability.

In this context, original nanocarriers were developed from very promising materials never used previously in the biomedical field: porous hybrid organic-inorganic crystalline solids also referred to as Metal-Organic Frameworks (MOFs) (see WO2009/077670, WO2009/077671 and WO2013/178954).

MOFs are crystalline hybrid coordination polymers comprising inorganic units and organic polycomplexant ligands coordinated through ionocovalent bonds to the cations. These materials are organized in three-dimensional frameworks in which the metal clusters are periodically connected together via spacer ligands. These materials are usually porous and are used in many industrial applications such as gas storage, liquid adsorption, liquid or gas separation, catalysis, etc.

Porous hybrid organic-inorganic nanoparticles (nanoMOFs) based on iron carboxylate or zinc imidazolate for instance, have recently been developed to address some of the challenges of galenic. Research in this area started from the statement that there is still a number of active agents with very short plasmatic half-life, difficultly crossing natural barriers of the body, or leading to resistance or toxicity. Nanoencapsulation was proposed as an interesting alternative for the administration of these active agents. Some of these molecules could not be successfully encapsulated in the currently used nanocarriers (liposomes, polymer-based nanoparticles or inorganic-based nanoparticles . . . ). The main reason is the incompatibility of these active molecules, in terms of sufficient interaction to be properly encapsulated, with the materials currently used to develop nanocarriers (such as polymers, lipids or oils). Another reason is the uncontrolled release of the challenging active molecules as a consequence of the fast diffusion from the nanoparticles to the aqueous medium due for instance to their important polarity (such as nucleoside analogues).

NanoMOFs are for example formed from units of iron (III) which produce amphiphilic large cages of defined size (3 to 60 Å) by bridging with endo or exogenous polycarboxylic acid, such as fumaric acid or trimesic acid. It is possible to modulate their pore size, structure and internal microenvironment (hydrophilic/hydrophobic balance) by varying the nature and the functionalization of the carboxylic acids used in the synthesis of nanoMOFs.

Due to their large pore volume and specific surface, nanoparticles or iron carboxylate nanoMOFs proved to be capable of adsorbing, by a simple impregnation in solutions of active principle, very large quantities of such active principle. Especially, they may adsorb more than 40% by weight in the case of some hydrophilic, amphiphilic or hydrophobic molecules. Therapeutic molecules having never before been effectively encapsulated (encapsulated quantities <1 or at most 5% by weight) are thus able to be encapsulated.

The degradability of these nanoMOFs in the body and their biocompatibility was evidenced. For example, injection of doses up to 220 mg/kg did not reveal any signs of toxicity in rats (as assessed by the animal behavior, weight, histology, changes in biological markers, metabolism, biodistribution, elimination). The ability of these nanoMOFs to produce an in vivo magnetic resonance imaging signal (MRI) was also shown. The contrast was attributed to both paramagnetic iron atoms and interconnected channels filled with water, coordinated to the metal sites and/or free. This observation has opened up attractive prospects in theranostic, for monitoring in vivo fate of nanoparticles loaded with active ingredients.

Reference may be made for example to international patent application WO2009/077670 for a description of such MOF nanoparticles.

Methods for modifying the outer surface of nanoMOFs were explored in order to control their interaction with the living environment and enable them selectively addressing in vivo. This is important insofar as the non-modified nanoMOFs are quickly recognized as foreign bodies and are eliminated after a few minutes by the reticuloendothelial system (accumulation in the liver and spleen).

International patent application WO2009/077671 describes methods of surface modification of nanoMOFs. For example, it is currently proposed to adsorb polyethyleneglycol linear chains (PEG) on the surface of nanoMOFs either during their synthesis or post-synthesis. This renders nanoMOFs "stealth", that is, capable of preventing accumulation in the liver and spleen leading then to longer circulation times.

However, this surface modification strategy has drawbacks, mainly due to the porous nature of MOFs materials, which leads to the adsorption of the surface agent not only on the outer surface of the nanoparticle but also within their porosity and then to a loss of pore volume and surface area. Especially, it was found that the capacity of encapsulation decreased, and there is a greater difficulty in controlling the release of active ingredients encapsulated therein. Thus, there is a need to develop other techniques than adsorption for modifying a porous solid while keeping good encapsulation and release capacities of molecules of interest.

International patent application WO2009/077671 also describes the use of polymers carrying hydrophobic groups capable of interacting with the outer surface of MOFs (such as dextran moieties grafted with fluorescein and biotin) for covering the surface MOFs. However, resulting modified MOF solids lack of stability, especially in physiological medium, which is an obstacle to their in vivo biomedical applications. There is a need to have methods for preparation of modified porous solids keeping a good stability in physiological medium.

International patent application WO2013/178954 describes a further method of surface modification of nanoMOFs. Especially, a surface agent comprising at least one complexing group is used to modify the outer surface of the nanoMOF. The surface agent is linked to the nanoMOF by complexation of metal ions and organic ligands which constitute the nanoMOF outer surface. However, it was found that by this method, the choice of the surface agent, and particularly its dimension in view of the pore size, was an important parameter to consider modifying MOFs in order to keep the porosity of these structures. Indeed, it is required both a surface agent size greater than pore size and functional groups allowing strong interaction between the surface agent and the MOF outer surface. Moreover, by this method, it is not possible to control the polymerization at the MOF outer surface, and as a consequence, the thickness of the polymer coating. Thus, there is a need to have a versatile procedure with regard to the choice of surface agent.

There is thus a need for improvements in terms of functionalization of the outer surface of porous solids, especially MOFs particles. In particular, there is a real need for improved compounds able to evade the immune system and/or rapid capture by certain organs, such as the liver, thus preventing their accumulation in these organs, and capable of vectorizing active ingredients to specific targets. There is a need to develop modified porous solids allowing retaining encapsulation and release capacities, i.e. retaining porosity.

The aim of the present invention is, precisely, to meet these needs and drawbacks of the prior art by providing an outer surface-modified porous solid, especially porous crystalline MOF solid, used as carrier for molecules of interest while keeping a good colloidal stability and a high porosity.

The Applicant unexpectedly evidenced that the Graftfast® method (WO2008/078052) of the invention allows under certain conditions, obtaining modified porous solids. This method enables chemically grafting a polymer at the surface of a solid support. The method is based on chemical reactions, essentially radical reactions of chemisorption and polymerization, hereafter referred to as "copolymerization-like reaction".

The Graftfast® method may be implemented using adhesion primers as sole building entities and a radical polymerizable monomer.

Adhesions primers are molecules capable of being chemisorbed at the surface of the substrate by radical reaction and allow indirect polymer grafting on any surface type. Generally, the adhesion primer includes diazonium salts which strong reactivity and ensures a robust covalent link between the polymer and the substrate. The reaction of the diazonium salts with a chemical activator having reducing properties allows the reduction of the diazonium and generation of radicals. The activator may be a chemical agent but it may also be a physical condition, such as for example a given temperature or a photoactivation.

The adhesion primer activated under the form of a radical can react either with the surface, forming a primary layer of adhesion, or with a radical polymerizable monomer allowing polymerization initiation. The growing polymer chain in solution then reacts with the radical building layer anchored on the surface.

The Graftfast® method had never been used before to graft polymers on porous substrates.

The Graftfast® method may be implemented using an adhesion primer, in a solvent, in presence of an activator (enabling the formation of radical entities) and in presence of radical polymerizable monomers. The polymer is simultaneously grafted and synthetized directly at the surface of the substrate.

Adhesion primers and monomers used to synthesize and graft the polymer on porous substrates were indeed expected clogging the pores.

Contrary to what was expected, the Applicant surprisingly evidences herein that the grafting of a polymer on a porous surface by Graftfast® method under certain conditions enables retaining porosity.

Thus, this invention relates to the outer surface modification of a porous solid, preferably a MOF solid, by the implementation of specific conditions of the Graftfast® method.

Advantages

The Graftfast® procedure is the method of choice for selectively grafting polymer on the outer surface of a porous solid while avoiding intrusion into the cavities. Without willing to be bound by a theory, two main features seems to hamper polymer intrusion: (i) the radical interaction of the polymer with the MOF surface (i.e. strong interaction); and (ii) the increase in size of the final polymer with respect to the accessible windows of the nanoMOF as a result of the radical polymerization process, which avoids intrusion.

Another advantage of the Graftfast® method is that it may allow the synthesis of star-like or branched polymer. This kind of polymer structure may provide interesting stealth properties (Okhil K. Nag and Vibhudutta Awasthi, Pharmaceutics. 2013, 5(4), 542-569, Hrkach et al., Biomaterials, 1997, 18(1), 27-30).

Moreover, the Graftfast® method may be conducted in aqueous medium. This is very valuable for resulting products having applications in cosmetic, pharmaceutical or medical fields. Thus, the Graftfast® method appears as a green process very easy to implement and leading to functionalized particles with a good colloidal stability, that enhance the bioavailability in a subject of such entities when used as pharmaceutical compounds.

Furthermore, the activator, in the Graftfast® method, is often iron. This is very interesting since MOFs used for medical application are often based on iron ions. Therefore, in embodiments wherein iron is used as activator, alteration of the structure of the MOF is prevented and no toxicological problem is observed with such materials.

Another advantage of the Graftfast® method is the simple purification of the modified porous solids of the invention. As diazonium salts are preferably used as adhesion primer, a release of $N_2$ occurs along the copolymerization-like reaction. Without willing to be bound by a theory, it is the Applicant's understanding that this gas comes housed in the pores of the porous solid, enabling the solids to float, and facilitating purification.

SUMMARY

This invention thus relates to a process for preparing a porous solid with an outer surface modified by at least one polymer; said polymer being simultaneously synthesized in solution and grafted on the outer surface of said solid, comprising contacting:
    a porous solid, wherein the porous solid is a particular solid, preferably selected from the group comprising alumina, hydroxyapatite, B-TCP, silica, zirconia, titania and/or a MOF solid; and a polymer-precursor solution comprising an adhesion primer, and at least one polymerizable monomer;

under conditions enabling the formation of radical entities.

According to one embodiment, said porous solid is a MOF solid comprising a three-dimensional succession of units of formula (I)

$$M_mO_kX_lL_p$$

wherein

M is a metal ion selected from the group comprising $Fe^{2+}$, $Fe^{3+}$, $Zn^{2+}$, $Zn^{4+}$, $Ti^{4+}$, $Zr^{4+}$, $Ca^{2+}$, $Cu^{2+}$, $Gd^{3+}$, $Mn^{2+}$, $Mn^{3+}$, $Mg^{2+}$, $Ag^+$, $Si^{4+}$ and $Al^{3+}$;

m, k, l and p are numbers $\geq 0$ chosen so as to respect the charge neutrality of the unit; preferably, m, k, l and p are independently 0 to 4, for example m and p are independently 1, 2 or 3 and/or k and l are independently 0 or 1;

X is a ligand selected from the group comprising $OH^-$, $Cl^-$, $F^-$, $I^-$, $Br^-$, $SO_4^{2-}$, $NO_3^-$, $ClO_4^-$, $R^1$—$(COO)_n^-$, $R^1$—$(SO_3)_n^-$, $R^1$—$(PO_3)_n^-$, in which $R^1$ is a hydrogen atom, a linear or branched C1 to C8 alkyl, n=1 to 6; and L is a polyfunctionnalized spacer ligand comprising a radical $R^0$ bearing q groups A, wherein q is a integer ranging from 2 to 6;

each occurrence of A is independently:

(i) a carboxylate

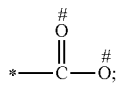

(ii) a phosphonate

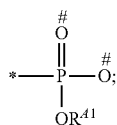

(iii) an imidazolate

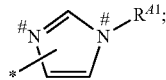

wherein $R^{41}$ is a hydrogen atom or a C1-C6 alkyl group;

wherein * denotes the point of attachment of the group A to the radical $R^0$;

wherein # denotes the possible points of attachment of the group A to the metal ion M;

$R^0$ represents (i) a C1-12 alkyl, C2-12 alkene or C2-12 alkyne radical;

(ii) a fused or non-fused monocyclic or polycyclic aryl radical, comprising 6 to 50 carbon atoms;

(iii) a fused or non-fused monocyclic or polycyclic heteroaryl, comprising 4 to 50 carbon atoms;

the $R^0$ radical being optionally substituted by one or more groups independently chosen in the group comprising $OH$, $NH_2$, $NO_2$ or a C1-C6 alkyl radical.

with a polymer-precursor solution comprising an adhesion primer, and at least one polymerizable monomer;

under conditions enabling the formation of radical entities.

According to one embodiment, the conditions enabling the formation of radical entities comprise the use of a reducing agent, preferably iron powder.

According to one embodiment, said solvent of the polymer-precursor solution is water, deionized water, distilled water, acidified or not, acetic acids, hydroxylated solvents such as ethanol, low-molecular-weight liquid glycols such as ethyleneglycol and mixtures thereof.

According to one embodiment, said adhesion primer is selected from cleavable aryl diazonium salts, aryl ammonium salts, aryl phosphonium salts and aryl sulfonium salts, preferably the adhesion primer is a 4-nitrobenzene diazonium salt.

According to one preferred embodiment, said adhesion primer is a cleavable diazonium salts of Formula (II)

$$R-N_2^+\cdot A^-$$

wherein, $A^-$ represents a monovalent anion,

R represents an aryl group, preferably, the adhesion primer is a 4-nitrobenzene diazonium salt.

According to one embodiment, said polymerizable monomer is selected from any radical polymerizable alkene comprising (meth)acrylate, styrenic, acrylamide or diene and derivatives thereof; preferably the radical polymerizable monomer is (meth)acrylate based monomer; more preferably is poly(ethyleneglycol)methyl ether acrylate or hydroxyethylmethacrylate.

According to one embodiment, said polymer-precursor solution comprises a precursor of adhesion primer, said precursor of adhesion primer allowing in situ synthesis of adhesion primer before contacting with a porous solid.

The invention also relates to a porous solid with an outer surface modified by a polymer, wherein the size of the pores is modified by at most 20%, as measured preferably by BET.

In one embodiment, the invention relates to a MOF solid with an outer surface modified by a polymer, wherein the size of the pores is modified by at most 20%, as measured preferably by BET.

Especially, the invention relates to a porous solid with an outer surface grafted with a polymer, where the polymer was simultaneously synthesized and grafted onto said outer surface, through contact of:

a porous solid; and a polymer-precursor solution comprising an adhesion primer, and at least one polymerizable monomer;

under conditions enabling the formation of radical entities.

According to one embodiment, the invention relates to a MOF solid with an outer surface grafted with a polymer, where the polymer was simultaneously synthesized and grafted onto said outer surface, through contact of:

a MOF solid; and a polymer-precursor solution comprising an adhesion primer, and at least one polymerizable monomer;

under conditions enabling the formation of radical entities.

According to one embodiment, said polymer was simultaneously synthesized and grafted onto said outer surface, through contact of a porous solid comprising a three-dimensional succession of units of formula (I)

$$M_mO_kX_lL_p$$

wherein

M is a metal ion selected from the group comprising $Fe^{2+}$, $Fe^{3+}$, $Zn^{2+}$, $Zn^{4+}$, $Ti^{4+}$, $Zr^{4+}$, $Ca^{2+}$, $Cu^{2+}$, $Gd^{3+}$, $Mn^{2+}$, $Mn^{3+}$, $Mg^{2+}$, $Ag^+$, $Si^{4+}$ and $Al^{3+}$;

m, k, l and p are numbers ≥0 chosen so as to respect the charge neutrality of the unit; preferably, m, k, l and p are independently 0 to 4, for example m and p are independently 1, 2 or 3 and/or k and l are independently 0 or 1;

X is a ligand selected from the group comprising $OH^-$, $Cl^-$, $F^-$, $I^-$, $Br^-$, $SO_4^{2-}$, $NO_3^-$, $ClO_4^-$, $R^1—(COO)_n^-$, $R^1—(SO_3)_n^-$, $R^1—(PO_3)_n^{31}$, in which $R^1$ is a hydrogen atom, a linear or branched C1 to C8 alkyl, n=1 to 6; and L is a polyfunctionalized spacer ligand comprising a radical $R^0$ bearing q groups A, wherein
q is a integer ranging from 2 to 6;
each occurrence of A is independently:
  (i) a carboxylate

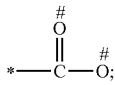

(ii) a phosphonate

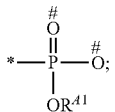

(iii) an imidazolate

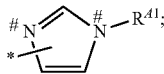

wherein $R^{41}$ is a hydrogen atom or a C1-C6 alkyl group;
wherein * denotes the point of attachment of the group A to the radical $R^0$;
wherein # denotes the possible points of attachment of the group A to the metal ion M;
$R^0$ represents
  a C1-12 alkyl, C2-12 alkene or C2-12 alkyne radical;
  a fused or non-fused monocyclic or polycyclic aryl radical, comprising 6 to 50 carbon atoms;
  a fused or non-fused monocyclic or polycyclic heteroaryl, comprising 4 to 50 carbon atoms;
  the $R^0$ radical being optionally substituted by one or more groups independently chosen in the group comprising OH, $NH_2$, $NO_2$ or a C1-C6 alkyl radical;
with a polymer-precursor solution comprising an adhesion primer, and at least one polymerizable monomer;
under conditions enabling the formation of radical entities.

The invention also concerns a device comprising a porous solid as described above, such as, for example, a medical device or a patch, wherein said porous solid preferably comprises an active principle in its pores.

The invention relates to a medicament comprising a porous solid as described above, wherein said porous solid preferably comprises a pharmaceutically active principle in its pores.

The invention relates to a pharmaceutical composition comprising a porous solid as described above and at least one pharmaceutically acceptable excipient, wherein the porous solid preferably comprises a pharmaceutically active principle in its pores.

The invention relates to a marker for use in medical imaging comprising a porous solid as described above.

The invention relates to a cosmetic composition comprising a porous solid as described above and at least one cosmetically acceptable excipient, wherein the porous solid preferably comprises a pharmaceutically active principle in its pores.

DEFINITIONS

In the present invention, the following terms have the following meanings:

"about" preceding a figure means plus or less 10% of the value of said figure.

"grafted" refers to chemically anchored by a covalent bound. A "surface grafted with a polymer" means that the polymer is linked to the surface by a covalent bound. In the present invention, a grafted surface should be understood in contrast with a coated surface, wherein the coating is adsorbed onto the surface. By "grafted", it is not referred to "adsorbed" or "complexed".

"copolymerization-like reaction" refers to a method by which a polymer is formed by the successive addition of free radical building blocks. In one embodiment, the copolymerization-like reaction is performed in presence of an adhesion primer and of an activator. In another embodiment, the copolymerization-like reaction is performed in presence of at least one adhesion primer, at least one polymerizable monomer and an activator.

"adhesion primer" refers to an organic molecule capable, under certain conditions, of being chemisorbed at the surface of a porous material, especially a MOF material, by a radical chemical grafting, and comprising a reactive function with respect to another radical after chemisorption. An adhesion primer is thus chemisorbable and polymerizable. In a preferred embodiment of the invention, adhesion primers comprise a diazonium salts moiety enabling their chemisorption at the surface of a porous solid, especially a MOF material, material by radical reaction.

"pharmaceutically acceptable" is meant that the ingredients of a pharmaceutical composition are compatible with each other and not deleterious to the subject to which it is administered. Accordingly, a "pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by Regulatory Agencies such as for example, FDA Office of Biologics standards.

"polymerizable" refers to a monomer for capable, under certain conditions, to be used for the synthesis of a polymer or an oligomer.

"polymerizable monomer" or "radical polymerizable monomer" refers to an organic molecule comprising a functional moiety, capable, under certain conditions, to be used as a monomer for the synthesis of a polymer by radical polymerization techniques. In one embodiment of the present invention, the polymerizable monomer is a polymerizable vinylic monomer, which refers to an organic molecule comprising a vinyl moiety, capable, under certain conditions, to be used as a monomer for the synthesis of a polymer.

"activator" refers to a chemical compound, such as a compound with reducing properties, or a physical condition, such as temperature or photoactivation, that allows the initiation of copolymerization-like reaction.

"conditions enabling the formation of radical entities" comprise the use of an activator according to the present invention.

"protic solvent" refers to a solvent that comprises at least one hydrogen atom capable of being released in proton form.

"solid" refers to any type of crystalline or amorphous material. In one embodiment, the solid is a crystalline material. In another embodiment, the solid is an amorphous material. Said solid may be, for example, in the form of crystals, powder or particles of varied forms, for example of spherical, cubic, parallelepipedic, rhomboedric, lamellar, etc. form. The particles may be in the form of nanoparticles, porous or not.

"nanoparticle" refers to a particle smaller than 1 µm in size. Especially, the solid MOF nanoparticles according to the invention may have a diameter of less than 1000 nanometers, preferably less than 500 nm, more preferably less than 250 nm and most particularly less than 100 nm.

In a general manner, the term "substituted" preceded or not by the term "optionally", and the substituents described in the formula of the present invention, denotes the replacement of a hydrogen radical in a given structure with the radical of a specified substituent. When more than one position may be substituted, the substituents may be the same or different in each position.

"spacer ligand" or "ligand" refers to a compound (including, for example, neutral species and ions) coordinated to at least two metals, which participates in providing distance between these metals and in forming empty spaces or pores. The spacer ligand may comprise various complexing functions comprising carboxylates, phosphonates, imidazolates, preferably from 2 to 6 functional groups being mono, bi, tri or tetradentates, i.e. possibly comprising 1, 2, 3 or 4 points of attachment to the metal.

"Surface agent" refers to a ligand used for functionalizing particles, especially the outer surface of MOF particles according to the invention.

"external surface", or "outer surface", represents the outside surface of the porous solid, i.e. excluding the surface of the pores (micropores and/or mesopores) of the porous solid.

"polyfunctionalized" is meant that a same compound is bearing more than one functional group.

"functional group" refers to a sub-molecular structure including an assembly of atoms conferring a reactivity specific to the molecule that contains it, for example an oxy, carbonyl, carboxy, sulfonyl group, and so on. In one embodiment of the present invention, "functional group" refers to at least one of the group selected from carboxylate, phosphonate or imidazolate.

"alkyl" refers to compound of formula $C_nH_{2n+1}$, wherein n is a number greater than or equal to 1. Generally, alkyl groups of this invention comprise from 1 to 12 carbon atoms. Alkyl groups may be linear or branched and may be substituted. Examples of alkyl groups are methyl, ethyl, n-propyl, i-propyl, butyl and its isomers (e.g. n-butyl, i-butyl and t-butyl); pentyl and its isomers, hexyl and its isomers.

"alkene" refers to any linear or branched hydrocarbon chain having at least one double bond, preferably 2 to 12 carbon atoms.

"alkyne" refers to any linear or branched hydrocarbon chain having at least one triple carbon bond; preferably 2 to 12 carbon atoms.

"aryl" refers to any polyunsaturated, aromatic hydrocarbyl group having a single ring (i.e. phenyl) or multiple aromatic rings fused together (e.g. naphtyl) or linked covalently, typically containing 6 to 50 atoms; preferably 6 to 10, wherein at least one ring is aromatic.

"heretoaryl" refers to aryl group having at least one atom that is not carbon or hydrogen; preferably, said atom is selected from N, S or O.

"Cosmetically acceptable" relates to a compound for use in contact with the skin and which does not provoke any side effects such as toxicity, irritation, inflammation or allergic response.

DETAILED DESCRIPTION

Modified Porous Solid

The present invention relates to a porous solid with a modified outer surface by a polymer, wherein the modification of the outer surface was carried out without any modifications of the size of the pores or wherein the size pore variation is less than 20%, 10%, 9%, 8%, 7%, 6%, 5%, 4%, 3% or 2%.

According to the invention, the measure of pore size variation is implemented by the Brunauer-Emmett-Teller method, also called BET, such as, for example, with the apparatus BELsorp mini (Bel, Japan).

According to one embodiment, no modification of the surface area was measured by BET before and after modification of the surface with the polymer.

The present invention relates to a porous solid with a modified outer surface, wherein the outer surface is modified by the grafting of a polymer, where the polymer was simultaneously synthetized and grafted onto said outer surface through contact of:
a porous solid; and
a polymer-precursor solution comprising an adhesion primer, and at least one polymerizable monomer;
under conditions enabling the formation of radical entities.

The present invention also relates to a porous solid (such as, for example, a MOF solid) with an outer surface modified by a polymer, obtainable by a process comprising contacting:
a porous solid (such as, for example, a MOF solid); and
a polymer-precursor solution comprising an adhesion primer and at least one radical polymerizable monomer;
under conditions enabling the formation of radical entities.

Especially, the invention relates to a porous solid (such as, for example, a MOF solid) with an outer surface modified by a polymer, obtainable by a process comprising contacting:
a porous solid (such as, for example, a MOF solid); and
a polymer-precursor solution comprising an adhesion primer and at least one radical polymerizable monomer;
under conditions enabling the formation of radical entities;
said porous solid (such as, for example, said MOF solid) having a size of the pores which is modified by at most 20%, as measured by BET.

In one embodiment, the polymer is synthetized under conditions enabling the formation of radical entities in absence of L-ascorbic acid.

According to one embodiment, the porous solid is a mesoporous (i.e. the pore size ranges from about 2 to about 50 nm) and/or microporous solid (i.e. the pore size is less than about 2 nm).

According to one preferred embodiment, the porous, mesoporous and/or microporous solid of the invention is a particular solid selected from the group comprising alumina, silica, hydroxyapatite, tricalcium phosphate (B-TCP), zirconia, titania and/or a MOF solid.

According to a preferred embodiment, the porous, mesoporous and/or microporous solid of the invention is a MOF solid comprising a three-dimensional succession of units of formula (I)

$$M_mO_kX_lL_p$$

wherein

M is a metal ion selected from the group comprising $Fe^{2+}$, $Fe^{3+}$, $Zn^{2+}$, $Zn^{4+}$, $Ti^{4+}$, $Zr^{4+}$, $Ca^{2+}$, $Cu^{2+}$, $Gd^{3+}$, $Mn^{2+}$, $Mn^{3+}$, $Mg^{2+}$, $Ag^+$, $Si^{4+}$ and $Al^{3+}$;

m, k, l and p are numbers $\geq 0$ selected so as to respect the charge neutrality of the unit; preferably, m, k, l and p are independently 0 to 4, for example m and p are independently 1, 2 or 3 and/or k and l are independently 0 or 1;

X is a ligand selected from the group comprising $OH^-$, $Cl^-$, $F^-$, $I^-$, $Br^-$, $SO_4^{2-}$, $NO_3^-$, $ClO_4^-$, $R^1$—$(COO)_n^-$, $R^1$—$(SO_3)_n^-$, $R^1$—$(PO_3)_n^-$, in which $R^1$ is a hydrogen atom, a linear or branched C1 to C8 alkyl, n=1 to 6; and L is a polyfunctionnalized spacer ligand comprising a radical $R^0$ bearing q groups A, wherein q is a integer ranging from 2 to 6;

each occurrence of A is independently:

(i) a carboxylate $$*-\overset{\overset{\#}{\overset{\|}{O}}}{C}-\overset{\#}{O};$$

(ii) a phosphonate $$*-\overset{\overset{\#}{\overset{\|}{O}}}{\underset{OR^{41}}{P}}-\overset{\#}{O};$$

(iii) an imidazolate $$*-\underset{N}{\overset{\#}{\underset{\|}{N}}}\diagdown\overset{\#}{\underset{N}{\diagup}}-R^{A1};$$

wherein $R^{41}$ is a hydrogen atom or a C1-C6 alkyl group;

wherein * denotes the point of attachment of the group A to the radical $R^0$;

wherein # denotes the possible points of attachment of the group A to the metal ion M;

$R^0$ represents a C1-12 alkyl, C2-12 alkene or C2-12 alkyne radical;

a fused or non-fused monocyclic or polycyclic aryl radical, comprising 6 to 50 carbon atoms;

a fused or non-fused monocyclic or polycyclic heteroaryl, comprising 4 to 50 carbon atoms;

the $R^0$ radical being optionally substituted by one or more groups independently chosen in the group comprising OH, $NH_2$, $NO_2$ or a C1-C6 alkyl radical.

In one embodiment, the first adhesion layer is grafted directly on the outer surface of the MOF solid by radical chemisorption and polymerization of an adhesion primer of Formula (II):

$$R-N_2^{+,}A^-$$

wherein $A^-$ is a monovalent anion,

R is an aryl group.

According to one preferred embodiment, the adhesion primer is selected from cleavable diazonium salts, aryl ammonium salts, aryl phosphonium salts and aryl sulfonium salts; preferably the adhesion primer is a 4-nitrobenzene diazonium salt.

According to one embodiment, the diazonium salt function in compound of Formula (II) may be obtained by reacting the corresponding compound, substituted by a primary amine, with sodium nitrite.

According to another embodiment, the polymer is simultaneously synthetized in solution and grafted directly on the outer surface of the porous solid, preferably a MOF solid, by radical chemisorption of an adhesion primer, preferably of formula (II) as defined above; said adhesion primer both reacts by radical chemisorption forming the first adhesion layer, and initiates in solution the polymerization of at least one polymerizable monomer selected from any radical polymerizable alkene comprising (meth)acrylate, styrenic, acrylamide or diene and derivatives thereof; preferably the polymerizable monomer is (meth)acrylate monomer; more preferably, poly(ethyleneglycol)methyl ether acrylate or hydroxyethylmethacrylate (HEMA).

According to one embodiment, the adhesion primer used in combination with the polymerizable monomer is preferably 4-nitrobenzenediazonium.

According to one embodiment, the polymerizable monomer is preferably a poly(ethyleneglycol)methyl ether acrylate (referred to as "acryl-PEG"). In one embodiment, the molecular weight of the acryl-PEG monomer is ranging from 100 Da to 10 kDa, preferably from 400 Da to 6 kDa, more preferably is equal to 480 Da, 2 kDa or 5 kDa.

According to one embodiment, the modified porous solid of the invention is in the form of crystals, powders, particles or nanoparticles.

According to one embodiment, the modified porous solid of the invention is functionalized by a molecule of interest, preferably selected from the group of biologically active molecules and/or contrast agents. In one embodiment, the molecule of interest is caffeine.

Advantageously, the outer surface of the MOF solid is not modified in that it comprises surface agents specifically described in international patent applications WO2009/0077671 and WO2013/178954.

According to one embodiment, the modified MOF solid of the invention comprises a MOF solid comprising a three-dimensional succession of units having formula (I) below:

$$M_mO_kX_lL_p$$

in which:
M is a metal ion selected from the group comprising $Fe^{2+}$, $Fe^{3+}$, $Zn^{2+}$, $Zn^{4+}$, $Ti^{4+}$, $Zr^{4+}$, $Ca^{2+}$, $Cu^{2+}$, $Gd^{3+}$, $Mn^{2+}$, $Mn^{3+}$, $Mg^{2+}$, $Ag^+$, $Si^{4+}$ and $Al^{3+}$;
m, k, l and p are numbers ≥0 chosen so as to respect the charge neutrality of the unit; preferably, m, k, l and p are independently 0 to 4, for example m and p are independently 1, 2 or 3 and/or k and l are independently 0 or 1;
X is a ligand selected from the group comprising $OH^-$, $Cl^-$, $F^-$, $I^-$, $Br^-$, $SO_4^{2-}$, $NO_3^-$, $ClO_4^-$, $R^1-(COO)_n^-$, $R^1-(SO_3)_n^-$, $R^1-(PO_3)_n^-$, in which $R^1$ is a hydrogen atom, a linear or branched C1 to C8 alkyl, n=1 to 6; and
L is a polyfunctionnalized spacer ligand comprising a radical $R^0$ bearing q groups A, in which
q is a integer ranging from 2 to 6;
each occurrence of A is independently:
(i) a carboxylate

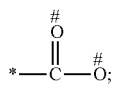

(ii) a phosphonate

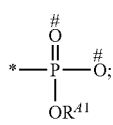

(iii) an imidazolate

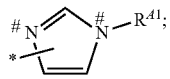

wherein $R^{41}$ is a hydrogen atom or a C1-C6 alkyl group;
wherein * denotes the point of attachment of the group A to the radical $R^0$;
wherein # denotes the possible points of attachment of the group A to the metal ion M;
$R^0$ represents
a C1-12 alkyl, C2-12 alkene or C2-12 alkyne radical;
a fused or non-fused monocyclic or polycyclic aryl radical, comprising 6 to 50 carbon atoms;
a fused or non-fused monocyclic or polycyclic heteroaryl, comprising 4 to 50 carbon atoms;
the $R^0$ radical being optionally substituted by one or more groups independently chosen in the group comprising OH, $NH_2$, $NO_2$ or a C1-C6 alkyl radical.
In the context of the present invention, the various occurrences of M in the units of formula (I) may be identical or different. Preferably, each occurrence of M is independently a metallic ion $Fe^{2+}$, $Fe^{3+}$, $Zn^{2+}$, $Zn^{4+}$, $Ti^{4+}$, $Zr^{4+}$, $Ca^{2+}$, $Cu^{2+}$, $Gd^{3+}$, $Mn^{2+}$, $Mn^{3+}$, $Mg^{2+}$, $Ag^+$, $Si^{4+}$ and $Al^{3+}$.
The MOF solid according to the invention may comprise divalent, trivalent or tetravalent metal atoms. The metal atoms may have an octahedral, pentahedral or tetrahedral geometry, or may even be of higher coordinance in the structure of the material.
The terms "coordinance" and "coordination number" refer to the number of bonds for which the two electrons shared in the bond originate from the same atom. The electron-donating atom acquires a positive charge, while the electron-accepting atom acquires a negative charge.

In addition, the metal atoms may be isolated or grouped into metal "clusters". The MOF solid according to the invention may be constructed, for example, from polyhedral chains, from dimers, trimers, tetramers, pentamers or hexamers of polyhedra, or from a combination thereof. For example, the MOF solid according to the invention may be constructed from octahedral chains, from dimers, trimers or tetramers of octahedra. For example, the iron carboxylate MOF materials according to the invention may be constructed from octahedral chains linked via apices or edges or octahedral trimers connected via a central oxygen atom.

For the purpose of the present invention, the term "metal cluster" refers to a group of atoms containing at least two metals linked via ionocovalent bonds, either directly via anions, such as for example O, OH, Cl or F; or via the organic ligand.

Furthermore, the MOF solid according to the invention may be in various forms or "phases", given the various possibilities for organization and connection of the ligands to the metal or to the metal group.

For the purpose of the present invention, the term "phase" refers to a hybrid composition comprising at least one metal and at least one organic ligand having a defined crystal structure.

The crystalline spatial organization of the solid of the present invention is the basis of the particular characteristics and properties of this material, and especially governs the pore size, which has an influence on the specific surface area of the material and on the adsorption characteristics, but also the density of the material, this density being relatively low, the proportion of metal in this material, the stability of the material, the rigidity and flexibility of its structure.

In addition, the MOF solid of the present invention may comprise units that contain either only one type of cation, or several types of cations.

According to a preferred embodiment, the L polyfunctionnalized spacer ligand is a ligand di-, tri-, tetra-, or hexa-carboxylate.

In addition, the pore size may be adjusted by choosing appropriate spacer ligands.

In one embodiment, the ligand L of the unit of the formula (I) of the MOF solids of the present invention may be a ligand bearing various complexing functions selected in a group comprising carboxylate, phosphonates, imidazolates, preferably the carboxylate group is a di-, tri-, tetra- or hexacarboxylate ligand selected from the group comprising:

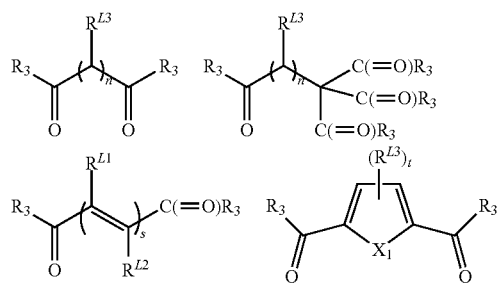

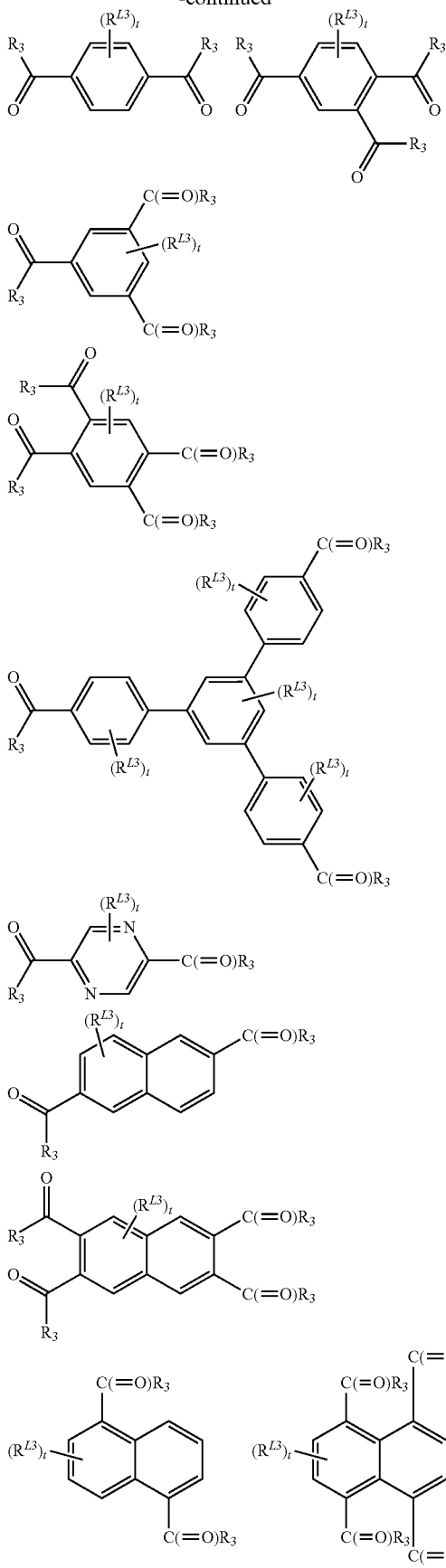
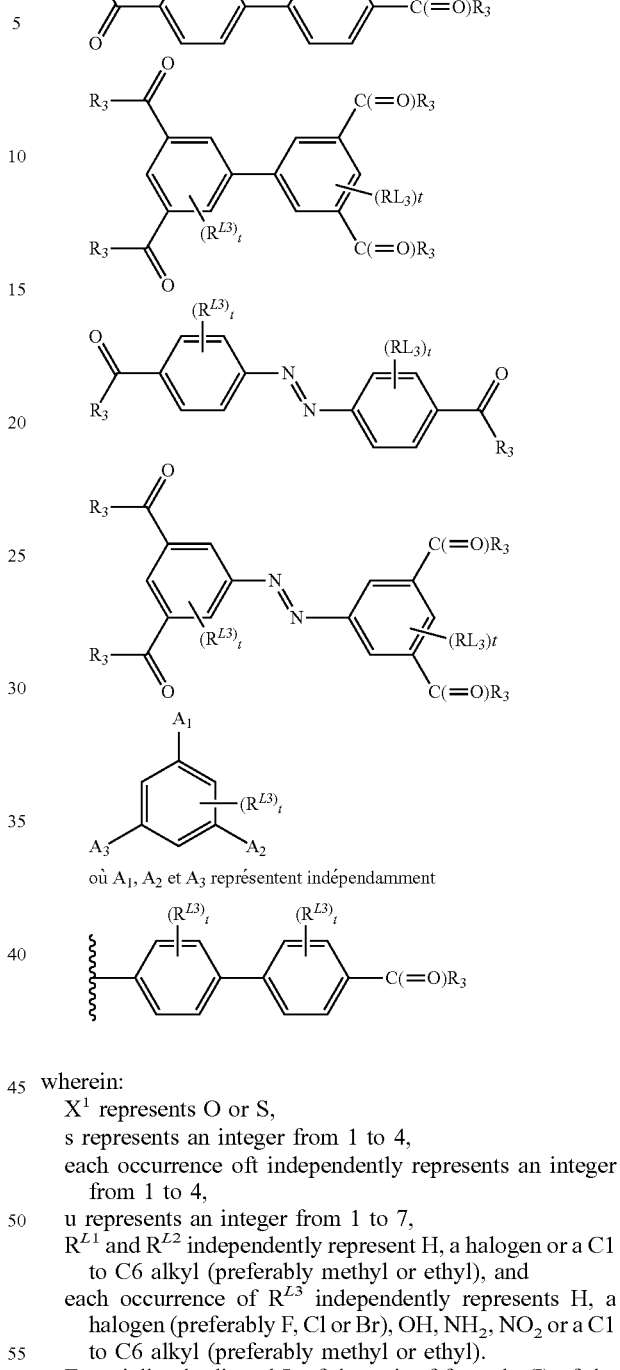

où $A_1$, $A_2$ et $A_3$ représentent indépendamment wherein:
$X^1$ represents O or S,
s represents an integer from 1 to 4,
each occurrence of t independently represents an integer from 1 to 4,
u represents an integer from 1 to 7,
$R^{L1}$ and $R^{L2}$ independently represent H, a halogen or a C1 to C6 alkyl (preferably methyl or ethyl), and
each occurrence of $R^{L3}$ independently represents H, a halogen (preferably F, Cl or Br), OH, $NH_2$, $NO_2$ or a C1 to C6 alkyl (preferably methyl or ethyl).

Especially, the ligand L of the unit of formula (I) of the present invention may be a di-, tri- or tetracarboxylate ligand selected from the group comprising: $C_2H_2(CO_2^-)_2$ (fumarate), $C_2H_4(CO_2^-)_2$ (succinate), $C_3H_6(CO_2^-)_2$ (glutarate), $C_4H_4(CO_2^-)_2$ (muconate), $C_4H_8(CO_2^-)_2$ (adipate), $C_2H_{14}(CO_2^-)_2$ (azelate), $C_5H_3S(CO_2^-)_2$ (2,5-thiophenedicarboxylate), $C_6H_4(CO_2^-)_2$ (terephthalate), $C_6H_2N_2(CO_2^-)_2$ (2,5-pyrazinedicarboxylate), $C_{10}H_6(CO_2^-)_2$ (naphthalene-2,6-dicarboxylate), $C_{12}H_8(CO_2^-)_2$ (biphenyl-4,4'-dicarboxylate), $C_{12}H_8N_2(CO_2^-)_2$ (azobenzenedicarboxylate), $C_6H_3(CO_2^-)_3$ (benzene-1,2,4-tricarboxylate), $C_6H_3(CO_2^-)_3$ (benzene-1,3,5-tricarboxylate), $C_{24}H_{15}(CO_2-)_3$ (benzene-1,3,5-tribenzoate), $C_6H_2(CO_2^-)_4$ (benzene-1,2,4,5-tetracarboxylate), $C_{10}H_4(CO_2^-)_4$ (naphthalene-2,3,6,7-tetracarboxylate), $C_{10}H_4(CO_2^-)_4$ (naphthalene-1,4,5,8-tetracarboxylate), $C_{12}H_6(CO_2^-)_4$ (biphenyl-3,5,3',5'-tetracarboxylate), and modified analogs selected from the group comprising 2-aminoterephthalate, 2-nitro-terephthalate, 2-methylterephthalate, 2-chloroterephthalate, 2-bromoterephthalate, 2,5-dihydroxoterephthalate, tetrafluoroterephthalate, tetramethylterephthalate, dimethyl-4,4'-biphenyldicarboxylate, tetramethyl-4,4'-biphenyldicarboxylate, dicarboxy-4,4'-biphenyldicarboxylate, 2,5-pyrazinedicarboxylate. The ligand L of the unit of formula (I) of the present invention may also represent 2,5-diperfluoro-terephthalate, azobenzene-4,4'-dicarboxylate, 3,3'-dichloroazobenzene-4,4'-dicarboxylate, 3,3'-dihydroxo-azobenzene-4,4'-dicarboxylate, 3,3'-diperfluoroazo-benzene-4,4'-dicarboxylate, 3,5,3',5'-azobenzene-tetracarboxylate, 2,5-dimethylterephthalate, perfluorosuccinate, perfluoromuconate, perfluoro-glutarate, 3,5,3',5'-perfluoro-4,4'-azobenzenedicarboxylate, 3,3'-diperfluoroazobenzene-4,4'-dicarboxylate.

Advantageously, the L ligand of the unit of formula (I) of the present invention may also be a ligand imidazolate, tetrazolate, phosphate or phosphonate such as imidazole, 2-methylimidazolate, 2-ethylimidazole, 4-imidazolecarboxylic acid, imidazole 4,5-dicarboxylic acid, 1,4-(butanediyl)bis(imidazole), purine, pyrimidine, benzimidazolate, piperazinediphosphonate, tetrazolylbenzoate.

Most of the ligands listed above are commercially available. The reader may refer to the Examples section of international patent applications WO2009/077670 and WO2009/077671 for the preparation of the non-commercial ligands.

In one embodiment, the ligand L has biological activity. The MOF solids according to the invention have a mineral part, the metal (preferably iron), and an organic part, a ligand with two or more complexing functions (such as carboxylate, phosphate, phosphonate, heterocyclic nitrogen, amide). The incorporation of organic ligands that have biological activity has the advantage of allowing controlled release of active molecules as a function of the rate of degradation of the material (it relates to above mentioned biologically active ligands that are released during the degradation of the MOF material). Thus, the MOF material itself may be "bioactive", i.e. it is capable of releasing components with biological activity.

In addition, the release of these active molecules that form part of the MOF framework may be combined with the release of other active principles encapsulated in the MOF solids according to the invention. This aspect of encapsulation of active principles is described herein below in the present document.

Thus, the present invention also relates to MOF solids comprising biologically active ligands and/or encapsulating one or more active principles, with potentially complementary or different activity, and to their use for combined therapies. The combined therapy is performed by releasing (i) the active principle encapsulated in the pores of the MOF material and (ii) biologically active ligands incorporated in the framework of the crystalline MOF material.

Many biologically active organic molecules exist comprising complexing functions, which are capable of forming porous hybrid MOF solids according to the present invention.

For example, it may be azelaic acid ($HO_2C(CH_2)_7CO_2H$, a dermatological agent with antineoplastic activity), meprobamate (anticonvulsive, sedative, muscle relaxant, antianxiety agent), aminosalicylic acid (antituberculosis), chlodronate, pamidronate, zoladronate, alendronate and etidronate (curative treatment of post-menopause osteoporosis), azobenzenes (antimicrobial activity, COX inhibitors), porphyrins, polyols, amino acids (such as Lys, Arg, Asp, Cys, Glu, Gln), 4-aminosalycique acid, pyrazinamide (antituberculosis), dibenzofuran-4,6-dicarboxylic acid (transtryretin inhibitor), dipicolinic acid (dihydrodipicolinate reductase inhibitor), glutamic acid, fumaric acid, succinic acid, suberic acid, adipic acid, nicotinic acid, nicotinamide, purines, pyrimidines.

Mention is made, for example, of the antimicrobial or anti-inflammatory activity (NSAIDs, COX inhibitors) of azobenzenes. In this respect, the reader may refer to the following references: G. Oros, T. Cserhati, E. Forgacs, *Chemosphere*, 52, 2003, 185, A. M. Badawi, E. M. S. Azzam, S. M. I. Morsy, *Bioorg. Med. Chem.*, 14, 2006, 8661, W-J. Tsai, Y-J Shiao, S-J Lin, W-F Chiou, L-C Lin, T-H Yang, C-M Teng, T-S Wu, L-M Yang, *Bioorg. Med. Chem. Letters* 16, 2006, 4440 and S. R. Miller et al., *Chem. Commun.*, 2013, 49, 7773.

Thus, the ligand L may be a biologically active ligand selected from the group comprising $C_7H_{14}(CO_2^-)_2$ (azelate); aminosalicylate (carboxylic, amino and hydroxy groups); chlodronate, pamidrontate, alendronate and etidronate (comprising phosphonate groups); meprobamate (comprising carbamate groups); porphyrins comprising carboxylate, phosphonate and/or amino groups; amino acids (such as Lys, Arg, Asp, Cys, Glu, Gln) which comprise amino, carboxylate, amide and/or imine groups; azobenzenes comprising carboxylate, phosphonate and/or amino groups; dibenzofuran-4,6-dicarboxylate, dipicolinate (mixed ligand of pyridine type with carboxylic groups); glutamate, fumarate, succinate, suberate, adipate, nicotinate, nicotinamide, purines, pyrimidines. In this respect, the reader may refer to the following reference: E. Alvarez et al., *Cryst. Eng. Comm.*, 2013, 15, 9899.

The anion X of the unit of formula (I) of the present invention may be selected from the group comprising $OH^-$, $Cl^-$, $Br^-$, $F^-$, $R-(COO)_n^-$, $PF_6^-$, $NO_3^-$, $SO_4^{2-}$ and $ClO_4^-$, with R and n as defined previously.

According to one embodiment, the anion X of the unit of formula (I) of the present invention is selected from the group comprising $OH^-$, $Cl^-$, $F^-$, $CH_3-(COO)_n^-$, $PF_6^-$, $ClO_4$, or ligand selected from the above list.

In one particular embodiment, the anion X may be selected from the group comprising $OH^-$, $Cl^-$, $F^-$ and $R-(COO)_n^-$ in which R represents $-CH_3$, $-C_6H_3$, $-C_6H_4$, $-C_{10}H_4$ or $-C_6(CH_3)_4$.

In one embodiment, the anion X may be in an isotopic form suitable for imaging techniques such as positron emission tomography (PET). For example, X may represent $^{18}F^-$, which is a positron emitter and thus allows the use of the porous solids of the invention for applications involving PET imaging. Thus, in one embodiment, in the unit of formula (I), at least one occurrence of the ligand X is $^{18}F$.

In an embodiment, the MOF solid according to the invention may comprise a percentage of metal in the dry phase ranging from 5% to 40% and preferably from 18% to 31%.

The mass percentage (m %) is a unit of measurement used in chemistry and metallurgy for denoting the composition of a mixture or an alloy, i.e. the proportions of each component in the mixture.

1 m % of a component=1 g of the component per 100 g of mixture, or 1 kg of said component per 100 kg of mixture.

The MOF solids of the present invention especially have the advantage of being thermostable up to a temperature of 400° C. According to one embodiment, the MOF solid of the present invention especially has the advantage of having heat stability from 120° C. to 400° C.

According to one embodiment, the MOF solid according to the invention is in particulate form with a particle diameter of less than 4 μm, preferably less than 1000 nanometers.

According to one embodiment, the MOF solid according to the invention has a pore size of from 0.4 to 6 nm, preferably from 0.5 to 5.2 nm and more preferably from 0.5 to 3.4 nm.

According to one embodiment, the MOF solid according to the invention has a specific surface area (BET) of from 5 to 6000 m$^2$/g, preferably from 5 to 4500 m$^2$/g. In one embodiment, the MOF solid according to the invention has a specific surface area (BET) ranging from 1000 to 2000 m$^2 \cdot$g$^{-1}$. In one embodiment, the MOF solid according to the invention has a specific surface area (BET) of about 1350 m$^2 \cdot$g$^{-1}$. In one embodiment, the MOF solid according to the invention has a specific surface area (BET) of about 1470 m$^2 \cdot$g$^{-1}$. In one embodiment, the MOF solid according to the invention has a specific surface area (BET) of about 1650 m$^2 \cdot$g$^{-1}$. In one embodiment, the MOF solid according to the invention has a specific surface area (BET) of about 1700 m$^2 \cdot$g$^{-1}$.

According to one embodiment, the specific surface area (BET) of the solid MOF is unchanged after the implementation of the Graftfast method.

According to one embodiment, the MOF solid according to the invention has a pore volume ranging from 0.05 to 4 cm$^3$/g and preferably from 0.07 to 2 cm$^3$/g. In the context of the invention, the pore volume refers to the volume accessible to gas and/or liquid molecules.

The Applicant has demonstrated that MOF materials comprising a three-dimensional structure of units of formula (I) may be in the form of a rigid or flexible structure. The MOF solid of the present invention may be in the form of a robust structure, which has a rigid framework and contracts very little when the pores empty, or in the form of a flexible structure, which may swell and shrink, causing the reversible opening/closing of the pores as a function of an external stimuli (pressure, temperature, the nature of the adsorbed molecules). These adsorbed molecules may be, for example, solvents and/or gases.

For the purpose of the present invention, the term "rigid structure" refers to structures that swell or contract very sparingly, i.e. with an amplitude of up to 10%. In one embodiment, the MOF solid according to the invention may have a rigid structure.

For the purpose of the present invention, the term "flexible structure" refers to structures that swell or contract with large amplitude, especially with an amplitude of greater than 10%, for example greater than 50%. In one embodiment, the MOF material of flexible structure may swell or contract with an amplitude ranging from 10% to 300%, preferably from 50% to 300%. According to one embodiment, the MOF solid according to the invention may have a flexible structure that swells or contracts with an amplitude of greater than 10%, for example from 50% to 300%.

The present invention may be implemented with MOF materials of rigid or flexible structure.

Various MOF materials were developed by the inventors at the Institut Lavoisier, Versailles with varied phases, known as "MIL" (for "Materiau Institut Lavoisier"). The name "MIL" for these structures is followed by an arbitrary number n given by the inventors to identify the various phases.

In the present document, the initials "ZIF" are the abbreviation of the term "Zeolite Imidazole Framework".

In the present document, the initials "UiO" are the abbreviation of the term "University of Oslo".

In the present document, the initials "AEPF" are the abbreviation of the term "Alkaline-Earth Polymer Framework".

The inventors also demonstrated that certain solids according to the invention may have a higher number of possible phases relative to the MOF materials conventionally encountered in the literature. For example, various phases were obtained for the iron(III) carboxylate solids according to the invention, for example MIL-53, MIL-69, MIL-88A, MIL-88B, MIL-88Bt, MIL-88C, MIL-88D, MIL-89, MIL-100, MIL-101, MIL-102. These various phases are presented in international patent applications WO2009/77670 and WO2009/77761.

The crystallographic characteristics of these structures are known, and have been the subject of numerous reports. So did the description and calculation of windows of access to the pores of higher size of the MOF materials of the present document (the reader will find all information in the publications cited in the present document for each type of specific MOF cited). Moreover, the abovementioned names "MIL" are well known to those skilled in the art. Mention will be made, for example, of:

MIL-53: Whitfield, T. R.; Wang, X.; Liu, L.; Jacobson, A. J. *Solid State Sci.* 2005, 7, 1096.

MIL-68: For this structural type, the reader may refer to the following publications: A. Fateeva et al., Synthesis, structure, characterization and redox properties of the porous MIL-68(Fe) solid, *Eur. J. Inorg. Chem.*, 2010, 3789.

MIL-69: T. Loiseau et al., *C. R. Chimie*, 8 765 (2005).

MIL-88A: (a) Serre et al., "Role of solvent-host interactions that lead to very large swelling of hybrid frameworks", *Science*, 2007, 315, 1828-1831; (b) Surblé et al., "A new isoreticular class of metal-organic frameworks with the MIL-88 topology", *Chem. Commun.*, 2006, 284-286; (c) Mellot-Draznieks et al., "Very large swelling in hybrid frameworks: a combined computational and power diffraction study", *J. Am. Chem. Soc.*, 2005, 127, 16273-16278, (d) Chalati et al., "Optimization of the synthesis of MOF nanoparticles made of flexible porous iron fumarate MIL-88A", *J. Mater. Chem.*, 2011, 21, 2220.

MIL-88B, MIL-88C and MIL-88D: For these structural types, the reader may refer to the publications concerning the MIL-88A type above, namely (a) Serre et al., "Role of solvent-host interactions that lead to very large swelling of hybrid frameworks", *Science*, 2007, 315, 1828-1831; (b) Surblé et al., "A new isoreticular class of metal-organic frameworks with the MIL-88 topology", *Chem. Commun.*, 2006, 284-286.

MIL-89: C. Serre, F. Millange, S. Surblé, G. Férey *Angew. Chem. Int. Ed.* 2004, 43, 6286: A new route to the synthesis of trivalent transition metals porous carboxylates with trimeric SBU.

MIL-100: Horcajada et al., "Synthesis and catalytic properties of MIL-100(Fe), an iron(III) carboxylate with large pores", *Chem. Commun.*, 2007, 2820-2822 and Volkringer et al., *Chem. Mater,* 2009, 21, 5695.

MIL-101: Férey et al., "A chromium terephthalate-based solid with unusually large pore volumes and surface area", *Science*, 2005, 309, 2040-2042.

MIL-102: S. Surblé, F. Millange, C. Serre, T. Duren, M. Latroche, S. Bourrelly, P. L. Llewellyn and G. Férey "MIL-102: A Chromium Carboxylate Metal Organic Framework with Gas Sorption Analysis" *J. Am. Chem. Soc.* 2006, 128, 46, 14890.

UiO-66: For this structural type, the reader may refer to the following publications: (a) J. Cavka, S. Jakobsen, U. Olsbye, N. Guillou, C. Lamberti, S. Bordiga, K. Lillerud *J Am. Chem. Soc.* 2008, 130, 13850; (b) M. Kandiah, M. H. Nilsen, S. Usseglio, S. Jakobsen, U. Olsbye, M. Tilset, C. Larabi, E. A. Quadreli, F. Bonino, K. P. Lillerud Chem. Mater., 2010, 22, 24, 6632; (c) M. Kim, S. M. Cohen *Cryst. Eng. Commun.*, 2012, 14, 4096.

ZIF-8: For this structural type, the reader may refer to Park et al., "Exceptional chemical and thermal stability of zeolitic imidazolate frameworks.", *Proc. Natl. Acad. Sci. U.S.A.*, 2006, 103, 10186.

MIL-125(Ti) and MIL-125(Ti)_$NH_2$: For this structural type, the reader may refer to the following publications: (a) M. Dan-Hardi, C; Serre, T. Frot, L. Rozes, G. Maurin, C. Sanchez and G. Férey "A new photoactive crystalline highly porous titanium (IV) dicarboxylate" *J. Am. Chem. Soc.*, 2009, 131, 10857-10859; (b) C. Zlotea, D. Phanon, M. Mazaj, D. Heurtaux, V. Guillerm, C. Serre, P. Horcajada, T. Devic, E. Magnier, F. Cuevas, G. Férey, P. L. Llewellyn and M. Latroche, "Effect of $NH_2$ and $CF_3$ functionalization on the hydrogen sorption poperties of MOFS" *Dalton Trans.*, 2011, 40, 4879-4881.

AEPF-1(Ca) and other calcium-based MOFs: For this structural type, the reader may refer to the following publications (a) A. E. Platero-Prats, V. A. de la Pena-O'Shea, N. Snejko, A. Monge, E. Gutierrez-Puebla, "Dynamic calcium metal-framework acts as a selective organic solvent sponge", *Chemistry*, 2010, 16, 38, 11632; (b) C. Volkringer, J. Marrot, G. Férey, T. Loiseau, "Hydrothermal crystallization of three calcium-based hybrid solids with 2,6-naphtalene or 4,4'-biphenyl-dicarboxylates.", *Crystal Growth Design*, 2008, 8, 685.

MIL-88B_$4CH_3$, MIL-88B_$CH_3$, MIL-88B_$2CF_3$, MIL-88B_$2OH$, MIL-88B_$NO_2$, MIL-88B_$NH_2$ MIL-88B_Cl, MIL-88B_Br, MIL-88B_4F: For this structural type, the reader may refer to the publications concerning the above MIL-88 type, namely (a) Serre et al., "Role of solvent-host interactions that lead to very large swelling of hybrid frameworks", *Science*, 2007, 315, 1828-1831; (b) Surblé et al., "A new isoreticular class of metal-organic frameworks with the MIL-88 topology", *Chem. Commun.*, 2006, 284-286; (c) Mellot-Draznieks et al., "Very large swelling in hybrid frameworks: a combined computational and power diffraction study", *J. Am. Chem. Soc.*, 2005, 127, 16273-16278; (d) Horcajada et al., "How linker's modification controls swelling properties of highly flexible iron(III) dicarboxylate MIL-88", *J. Am. Chem. Soc.*, 2011, 133, 17839.

MIL-127: For this structural type, the reader may refer to the following publication: A. Dhakshinamoorthy et al., Iron (III) metal-organic frameworks as solid Lewis acids for the isomerization of α-pinene oxide, Catal. Sci. Techn., 2012, 2, 324.

MIL-140: For this structural type, the reader may refer to the following publications: V. Guillerm et al., A series of isoreticular, highly stable, porous zirconium oxide based metal-organic frameworks, Angew. Chem. Int. Ed., 2012, 51, 9267.

MIL-142 and MIL-143: For these structural types, the reader may refer to the following publication: H. Chevreau, et al., Mixed linker hybrid superpolyhedra for the production of a series of large-pore iron(III) carboxylate metal-organic frameworks, Angew Chem Int Ed, 2013, 52, 5056.

BioMIL-1: For this structural type, the reader may refer to the following publication: S. R. Miller et al., Biodegradable therapeutic MOFs for the delivery of bioactive molecules, Chem Commun, 2010, 46, 4526.

BioMIL-2: S. R. Miller, Small chemical causes drastic structural effects: the case of calcium glutarate, CrystEngComm, 2011, 13, 1894.

BioMIL-3: S. R. Miller et al., A rare example of a porous Ca-MOF for the controlled release of biologically active NO, Chem Commun, 2013, 49, 7773.

BioMIL-4: E. Alvarez et al. A biocompatible calcium bis-phosphonate coordination polymer: towards a metal-linker synergistic therapeutic effect? Cryst. Eng. Comm, 2013, 15, 9899.

According to one embodiment, the MOF solid according to the invention has a unit of formula selected from the group comprising:

$Fe(OH)[C_6H_4(CO_2)_2]$ of flexible structure, for example MIL-53 and its functionalized from MIL-53(Fe)_X (X=Cl, Br, $CH_3$, $2CF_3$, ... ), see reference Devic et al., "Functionnalization in flexible porous solids: effect on the pore opening and the host-guest interactions", *J. Am. Chem. Soc.* 2010, 132, 1127;

$Fe_3OX[C_2H_2(CO_2)_2]_3$ of flexible structure, for example MIL-88A;

$Fe_3OX[C_4H_4(CO_2)_2]_3$ of flexible structure, for example MIL-89 (see reference: C. Serre, S. Surblé, C. Mellot-Draznieks, Y. Filinchuk, G. Férey, "Evidence of flexibility in the nanoporous iron(III) carboxylate MIL-89", *Dalton Trans.*, 2008, 5462-5464;

$Fe_3OX[C_6H_4(CO_2)_2]_3$ of flexible structure, for example MIL-88B;

$Fe_3OX[O_2C-C_6(CH_3)_4-CO_2]_3 \cdot nH_2O$ of flexible structure, for example MIL-88Bt;

$Fe_3OX[C_6H_4(CO_2)_2]_3$ of rigid structure, for example MIL-101;

$Fe_3OX[C_6H_3(CO_2)_3]_3$ of rigid structure, for example MIL-100;

$Fe_3OX[C_{10}H_6(CO_2)_2]_3$ of flexible structure, for example MIL-88C;

$Fe_3OX[C_{12}H_8(CO_2)_2]_3$ of flexible structure, for example MIL-88D;

$Zn_6N_{24}C_{48}H_{60}$ of rigid structure, for example ZIF-8;

$Zr_6O_4(OH)_4[|(CO_2)_2C_6H_4]_6$ of rigid structure, for example UiO-66;

$Ti_8O_8(OH)_4[(CO_2)_2C_6H_4]_6$ of rigid structure, for example MIL-125;

in which X is as defined previously.

Most particularly, the MOF solid according to the invention may have a unit of formula selected from the group comprising:

MIL-101 (Fe) or $Fe_3O[C_6H_4-(CO_2)_2]_3 \cdot X \cdot nH_2O$ (X=F, Cl, OH) of rigid structure;

MIL-101-Cl (Fe) or $Fe_3O[Cl-C_6H_3-(CO_2)_2]_3 \cdot X\ nH_2O$ (X=F, Cl, OH) of rigid structure;

MIL-101-$NH_2$ (Fe) or $Fe_3O[NH_2-C_6H_3-(CO_2)_2]_3 \cdot X \cdot nH_2O$ (X=F, Cl, OH) of rigid structure;

MIL-101-$2CF_3$ (Fe) or $Fe_3O[(CF_3)_2-C_6H_2-(CO_2)_2]_3 \cdot X \cdot nH_2O$(X=F, Cl, OH) of rigid structure;

MIL-88B-$NO_2$ (Fe) or $Fe_3O[C_6H_3NO_2-(CO_2)_2]_3 \cdot X \cdot nH_2O$ (X=F, Cl, OH) of flexible structure;

MIL-88B-2OH (Fe) or $Fe_3O[C_6H_2(OH)_2-(CO_2)_2]_3 \cdot X \cdot nH_2O$ (X=F, Cl, OH) of flexible structure;

MIL-883-NH$_2$ (Fe) or Fe$_3$O[C$_6$H$_3$NH$_2$—(CO$_2$)$_2$]$_3$.X.nH$_2$O (X=F, Cl, OH) of flexible structure;

MIL-88B-CH$_3$ (Fe) or Fe$_3$O[C$_6$H$_3$CH$_3$—(CO$_2$)$_2$]$_3$.X.nH$_2$O (X=F, Cl, OH) of flexible structure;

MIL-88B-2CH$_3$ (Fe) or Fe$_3$O[C$_6$H$_2$(CH$_3$)$_2$—(CO$_2$)$_2$]$_3$.X.nH$_2$O (X=F, Cl, OH) of flexible structure;

MIL-88B-Cl (Fe) or Fe$_3$O[C$_6$H$_3$Cl—(CO$_2$)$_2$]$_3$.X.nH$_2$O (X=F, Cl, OH) of flexible structure;

MIL-88B-4CH$_3$ (Fe) or Fe$_3$O[C$_6$(CH$_3$)$_4$—(CO$_2$)$_2$]$_3$.X.nH$_2$O (X=F, Cl, OH) of flexible structure;

MIL-88B-4F (Fe) or Fe$_3$O[C$_6$F$_4$—(CO$_2$)$_2$]$_3$.X.nH$_2$O(X=F, Cl, OH) of flexible structure;

MIL-88B-Br (Fe) or Fe$_3$O[C$_6$H$_3$Br—(CO$_2$)$_2$]$_3$.X.nH$_2$O (X=F, Cl, OH) of flexible structure;

MIL-88B-2CF$_3$ (Fe) or Fe$_3$O[(CF$_3$)$_2$]—C$_6$H$_2$—(CO$_2$)$_2$]$_3$.X.nH$_2$O(X=F, Cl, OH) of flexible structure;

MIL-88D 4CH$_3$ (Fe) or Fe$_3$O[C$_{12}$H$_4$(CH$_3$)$_4$—(CO$_2$)$_2$]$_3$.X.nH$_2$O(X=F, Cl, OH) of flexible structure;

MIL-88D 2CH$_3$ (Fe) or Fe$_3$O[C$_{12}$H$_6$(CH$_3$)$_2$—(CO$_2$)$_2$]$_3$.X.nH$_2$O (X=F, Cl, OH) of flexible structure;

MIL-88E (Pyr) (Fe) or Fe$_3$O[C$_4$H$_3$N$_2$—(CO$_2$)$_2$]$_3$.X.nH$_2$O (X=F, Cl, OH) of flexible structure;

MIL-88F (Thio) (Fe) or Fe$_3$O[C$_4$H$_2$S—(CO$_2$)$_2$]$_3$.X.nH$_2$O (X=F, Cl, OH) of flexible structure;

MIL-53-2OH (Fe) or FeO(OH)[C$_6$H$_2$(OH)$_2$—(CO$_2$)$_2$].X.nH$_2$O(X=F, Cl, OH) of flexible structure;

MIL-53-NH$_2$ (Fe) or FeO(OH)[C$_6$H$_2$—NH$_2$—(CO$_2$)$_2$].X.nH$_2$O (X=F, Cl, OH) of flexible structure;

MIL-53-Cl (Fe) or FeO(OH)[C$_6$H$_2$—Cl—(CO$_2$)$_2$].X.nH$_2$O (X=F, Cl, OH) of flexible structure;

MIL-53-Br (Fe) or FeO(OH)[C$_6$H$_2$—Br—(CO$_2$)$_2$].X.nH$_2$O (X=F, Cl, OH) of flexible structure;

MIL-53-2CF$_3$ (Fe) or FeO(OH)[C$_6$H$_2$(CF$_3$)$_2$—(CO$_2$)$_2$].X.nH$_2$O(X=F, Cl, OH) of flexible structure;

MIL-53-CH$_3$ (Fe) or FeO(OH)[C$_6$H$_3$CH$_3$—(CO$_2$)$_2$].X.nH$_2$O (X=F, Cl, OH) of flexible structure;

MIL-53-2COOH (Fe) or FeO(OH)[C$_6$H$_3$—(CO$_2$)$_4$].X.nH$_2$O (X=F, Cl, OH) of flexible structure;

MIL-88G (AzBz) (Fe) or Fe$_3$O[C$_{12}$H$_8$N$_2$—(CO$_2$)$_2$]$_3$.X.nH$_2$O (X=F, Cl, OH) of flexible structure;

MIL-88G 2Cl (AzBz-2Cl) (Fe) or Fe$_3$O[C$_{12}$H$_6$N$_2$Cl$_2$—(CO$_2$)$_2$]$_3$.X.nH$_2$O (X=F, Cl, OH) of flexible structure.

In addition, from the same carboxylic acid ligand L and the same iron bases (chains or trimers), the inventors were able to obtain MOF materials of the same general formula (I) but of different structures. This is the case, for example, for the solids MIL-88B and MIL-101. Specifically, the difference between the solids MIL-88B and MIL-101 lies in the mode of connection of the ligands to the octahedral trimers: in the solid MIL-101, the ligands L assemble in the form of rigid tetrahedra, whereas in the solid MIL-88B, they form trigonal bipyramids, enabling spacing between the trimers.

These various materials are presented in international patent applications WO2009/77670 and WO2009/77671. The mode of assembly of these ligands may be controlled during the synthesis, for example by adjusting the pH. For example, the solid MIL-88 is obtained in a less acidic medium than the solid MIL-101, as described in international patent application WO2009/77671.

According to one embodiment, the MOF solid of the present invention may have a phase selected from the group comprising: MIL-53, MIL-88, MIL-100, MIL-101, MIL-102 described in the international patent application WO2009/77671, ZIF-8, MIL-127, MIL-140, MIL-125 and UiO-66.

According to a specific embodiment of the invention, the MOF solid which outer surface is modified, is selected from MIL-100 and ZIF-8, preferably from MIL-100(Fe), MIL-100(Al) or ZIF-8.

According to one embodiment, the MOF solid according to the invention may comprise at least one metal with paramagnetic or diamagnetic properties. Preferably, the MOF solid according to the invention may comprise one or more identical or different paramagnetic metals, which may be iron. According to one embodiment, the MOF solid according to the invention may comprise one or more identical or different paramagnetic metal ions, which may be selected from the group comprising $Fe^{2+}$ and $Fe^{3+}$.

Specifically, contrast agents are characterized by their relaxivity. The greater this relaxivity, the larger the effect of the contrast agents. The relaxivity corresponds to the capacity of contrast agents to modify the relaxation times of protons of the water of the medium following the application of a magnetic field. It depends on the paramagnetic properties of the metals used, but also on the amount and mobility of the water molecules that coordinate to the metal in the first inner sphere, bringing the largest contribution, and also in the outer sphere. These "coordination spheres" represent the atoms immediately attached to the metallic center in the case of the $1^{st}$ sphere; for the outer sphere, this represents the atoms immediately located beyond the $1^{st}$ sphere.

In the case of the solid of the invention, besides the magnetic susceptibility of the metal, in this example iron (III), the structural characteristics of the solid of the present invention allow water to be coordinated around the $1^{st}$ coordination sphere and to circulate in the pores, which induces an effect on the longitudinal T1 and transverse T2 relaxation times of the protons of water. Especially, the relaxivity r2 of the solid is sufficient for in vivo use during gradient echo experiments.

Modified Outer Surface of the Porous Solid

The polymer grafted onto the outer surface of the porous solid of the invention is simultaneously synthetized and grafted onto said outer surface through contact of:
a porous solid; and
a polymer-precursor solution comprising an adhesion primer, and at least one radical polymerizable monomer;
under conditions enabling the formation of radical entities.

In one embodiment, the polymer is simultaneously synthetized and grafted onto said outer surface under conditions enabling the formation of radical entities in the absence of L-ascorbic acid.

According to one embodiment, the polymer grafted at the outer surface of the porous solid has a molecular weight (Mw) ranging from 10 to 100 000 g/mole, preferably from 100 to 50 000 g/mole, more preferably below 20 000 g/mole. According to one embodiment, the polymer grafted at the outer surface of the porous solid has a molecular weight (Mw) equal to about 480 Da, 2 kDa or 5 kDa.

According to one embodiment, the polymer grafted at the outer surface of the porous solid has any structure and/or chain conformation comprising linear, block, random, gradient, star, graft or "comb", hyperbranched or dendritic (co)polymer. According to one preferred embodiment, the polymer has no linear chain conformation.

According to one embodiment, the amount of polymer grafted at the outer surface of the porous solid is ranging from 0.5 to 100 wt % (wherein wt % stands for the percentage in weight to the weight of the porous solid), preferably from 1 to 50 wt %, more preferably from 5 to 40 wt % with respect to dry porous solid weight. In one embodiment, the amount of polymer grafted at the outer surface of the porous solid is about 30 wt % with respect to dry porous solid weight. In one embodiment, the amount of polymer grafted at the outer surface of the porous solid is about 10 wt % with respect to dry porous solid weight.

According to one embodiment, the density of polymer grafted at the outer surface of the MOF solid is ranging from 1 to 30 entities per $nm^2$, preferably from 5 to 20 entities per $nm^2$. In one embodiment, the density of polymer grafted at the outer surface of the MOF solid is about 10 entities per $nm^2$.

In one embodiment, the porous solid with modified outer surface of the invention remain stable in physiological conditions for a period of time ranging from 0.5 to 200 hours, preferably from 2 to 72 h, more preferably from 4 to 24 hours. By "remain stable" it is understood the polymer remains associated to the outer surface of the particle (not released to the media).

According to one preferred embodiment, the crystallinity of the porous solid and of the modified porous solid of the invention may be determined by X-ray diffraction (XRD), preferably X ray powder diffraction (XRPD). Measurements may be performed using a D8 Advance Bruker diffractometer, preferably with Cu K$\alpha$1 radiation (lambda=1.54056 angstroms) from 3 to 30° (2θ) using a step size of 0.02° and 4 s per step in continuous mode.

According to an embodiment, the presence of the polymer on the modified porous solid of the invention may be detected using Fourier transform infrared (FTIR) spectroscopy. Measurement may be performed a Nicolet 6700 instrument (Thermo scientific, USA) from 4000 to 400 $cm^{-1}$.

According to one embodiment, the particle size of the porous solid and of the modified porous solid of the invention may be determined using Dynamic Light Scattering (DLS). Measurements may be performed on a Zetasizer Nano (Malvern Instruments). In one embodiment, the particle size of the porous solid and of the modified porous solid of the invention are less than 1 µm. In one embodiment, the particle size of the porous solid of the invention is about 148 nm. In one embodiment, the particle size of the porous solid of the invention is about 171 nm. In one embodiment, the particle size of the modified porous solid of the invention is about 134 nm. In one embodiment, the particle size of the modified porous solid of the invention is about 176 nm.

According to one embodiment, the porosity of the porous solid and of the modified porous solid of the invention and the localization of the polymer at the surface of the modified porous solid may be determined by recording $N_2$ adsorption isotherms. Measurements may be performed at 77 K using a BELsorp Mini (Bel, Japan). In one embodiment, prior to the analysis, approximately 30 mg of sample are evacuated at 140° C. under primary vacuum for 3 h.

According to one embodiment, the quantification of the amount of polymer on the modified porous solid of the invention may be performed by thermogravimetric analyses (TGA). Preferably the room temperature (RT) samples (5-10 mg) are analyzed on a Perkin Elmer Diamond TGA/DTA STA 6000 under $O_2$ atmosphere (20 mL·$min^{-1}$), at heating speed of 3° C./min for the temperature range between RT and 600° C. Results are expressed in percentage by weight with respect to dry MOF solid weight.

According to one embodiment, the ζ-potential of the modified porous solid of the invention is determined by Electrophoretic Light Scattering (ELS). Measurements may be performed on a Zetasizer Nano (Malvern Instruments).

According to one embodiment, the nature of the grafting mechanism is determined by X-ray photoelectron spectroscopy (XPS). Measurement may be performed using Kratos XPS apparatus (Kratos Axis Ultra DLD AlKα monochromatic source).

Process of Manufacturing

The present invention further relates to a process for manufacturing a porous solid with modified outer surface.

According to one embodiment, the process of the invention is a process for preparing a porous solid with an outer surface modified by at least one polymer; said at least one polymer being simultaneously synthesized in solution and grafted on the outer surface of said porous solid, comprising contacting:
  a porous solid; and
  a polymer-precursor solution comprising an adhesion primer and at least one radical polymerizable monomer;
under conditions enabling the formation of radical entities.

In one embodiment, the process is carried out in absence of L-ascorbic acid.

According to one embodiment, the porous solid is a particular solid selected from the group comprising alumina, hydroxyapatite, B-TCP, zirconia, titania, silica and/or a MOF solid.

According to one preferred embodiment, the porous solid is a MOF solid as hereinabove described. The manufacturing of the modified MOF solid used in the process of the invention may be performed as described international patent application WO2009/077670.

According to one embodiment, the polymerizable monomer is selected from any radical polymerizable alkene comprising (meth)acrylate, styrenic, acrylamide or diene and/or derivatives thereof; preferably the polymerizable monomer is (meth)acrylate monomer; more preferably, poly (ethyleneglycol)methyl ether acrylate or hydroxyethylmethacrylate (HEMA). In one embodiment, the polymerizable monomer is acryl-PEG.

According to one embodiment, the process of the invention further comprises at least one step for preparing at least one further polymer shell on the modified porous solid, comprising contacting:
  the modified porous solid functionalized with a first polymer layer; and
  a polymer-precursor solution comprising an adhesion primer and at least one radical polymerizable monomer (said monomer being the same or different from the monomer used for the synthesis of the first polymer layer);
under conditions enabling the formation of radical entities.

According to one embodiment, the process of the invention further comprises more than one step for functionalizing the polymer anchored at the outer surface of the modified porous solid, comprising contacting:
  the porous solid with modified outer surface; and
  a solution comprising a molecule of interest.

According to one embodiment, the molecule of interest is a compound selected from the group of biologically active compounds (such as, for example, drugs, cosmetics, small molecules for targeting tumors such as folic acid or biotin and the like), or contrast agent (such as, for example, iron oxides, gold, fluorophores, etc).

As explained above the grafting reaction first comprises the formation of radicals from the adhesion primer. The radicals' formation may be initiated in presence of a chemical activator and/or chemical or physical conditions. According to one embodiment, the conditions enabling the formation of radical entities in the process of the invention may be obtained by using an activator, for example by varying the temperature and/or by adding a chemical activator and/or by using a photochemical and/or radiochemical environment.

According to a first embodiment, the conditions enabling the formation of radical entities may be obtained by adding in the solution used in the process of the present invention a reducing agent as chemical activator. The reducing agent may be for example a metal, generally in finely divided form (metallic wool or metal filings), such as iron, zinc, nickel; a metallic salt or metallocene; an organic reducing agent such as orthophosphoric acid, glucose, galactose, hydrogen.

According to one preferred embodiment, the conditions enabling the formation of radical entities comprise the use of a reducing agent; preferably, iron powder.

According to a specific embodiment, the reducing agent is not orthophosphoric acid. According to a specific embodiment, the reducing agent is not ascorbic acid.

According to a specific embodiment, the reducing agent is a metallic ion which does not modify the integrity of the porous solid after the modification of its outer surface by polymer; especially the reducing agent is only involved in the implementation of the modification surface by polymer.

Preferably, the reducing agent is pharmaceutically acceptable.

In the present invention, the adhesion primer preferably comprises a diazonium salt function which enables its chemisorption on the MOF material. When the diazonium salt is reduced to form an aryl radical, there is at the same time a nitrogen release.

According to second embodiment, the radicals formation is initiated by a physical conditions, for example by using a specific temperature or by illumination at a given wave length. Examples of conditions of initiation have previously been described in WO2008/070852, which is incorporated herein by reference.

According to one embodiment, the solution used in the process of the invention is an acidic solution; preferably in HCl solution. In this embodiment, the pH of the solution is ranging from 1 to 7, preferably from 2 to 4, more preferably less than or equal to 3. Preferably, in this embodiment, the process of the invention is conducted using a 50 mM HCl solution. According to an alternative embodiment, the solution used in the process of the invention has a pH ranging from 1 to 7, preferably from 3 to 7, more preferably the solution is a neutral solution, preferably water.

According to one embodiment, the solvent of the solution used in the process of the invention is a protic solvent. In an embodiment, the protic solvent is selected from the group comprising water, deionized water, distilled water, acidified or not, acetic acids, hydroxylated solvents such as methanol and ethanol, low-molecular-weight liquid glycols such as ethyleneglycol and mixtures thereof. In a preferred embodiment, the protic solvent is water, deionised water or distilled water, acidified or not. According to another embodiment, the solvent of the solution used in the process of the invention is an aprotic solvent, preferably dimethylsulfoxide. Alternatively, the solvent of the solution used in the process of the invention is a mixture of a protic solvent or a mixture of protic solvents together with an aprotic solvent or a mixture of aprotic solvents.

Preferably, the solvent is pharmaceutically acceptable.

According to one embodiment, the solvent of the solution used in the process of the invention solution comprises an adhesion primer or its precursor. In one specific embodiment, the precursor of adhesion primer allows in situ synthesis of adhesion primer before contacting with a porous solid.

According to one embodiment, the adhesion primer used in the process of the invention is a cleavable diazonium salts of Formula (II):

$R-N_2^+,A^-$ wherein, $A^-$ represents a monovalent anion,

R represents an aryl group.

According to a very preferred embodiment, the adhesion primer is selected from cleavable aryl diazonium salts, aryl ammonium salts, aryl phosphonium salts and aryl sulfonium salts. According to a specific embodiment, the adhesion primer is a 4-nitrobenzene diazonium salt (NBD).

According to a first embodiment, the adhesion primer under the form of a diazonium salt is directly introduced in the solution used in the process of the present invention. In one embodiment, the diazonium salt may have been separately obtained by reacting an aniline derivative (i.e. an aromatic primary amine) with boron trifluoride diethyl etherate in presence of tert-butyl nitrite and isolating the resulting diazonium salt. The skilled artisan may also refer to other known methods to synthesize and isolate diazonium salts in order to obtain the adhesion primers.

According to a second embodiment, the adhesion primer under the form of a diazonium salt is prepared in situ in the solution used in the process of the invention before contacting with a porous solid. The diazonium salt may be obtained by reacting an aniline derivative (i.e. an aromatic primary amine) with $NaNO_2$ in an acidic medium. For detailed experimental method that may be used for such an in situ preparation, one skilled artisan can refer to Lyskawa and Belanger, Chem. Mater. 18, 2006, 4755-4763. The grafting will then be performed directly in the solution used for the preparation of the diazonium salt.

According to one embodiment, the amount of adhesion primer, in the solution used in the process of the present invention may vary as desired by the experimenter. Variations of this amount may participate to the control of the molecular weight of the grafted polymer and to its repartition onto the surface. In order to obtain a polymer grafted on the quite entire outer surface of the porous solid, it is necessary to use a minimum amount of adhesion primer which may be estimated by molecular size calculation together with the size of the surface to be grafted.

Preferably, the adhesion primer is pharmaceutically acceptable.

According to an embodiment the polymerizable monomer is selected from any radical polymerizable alkene; preferably, the polymerizable monomer is selected from the group of vinyl acetate, acrylonitrile, methacrylonitrile, methylmethacrylate, ethylmethacrylate, butylmethacrylate, propylmethacrylate, hydroxyethylmethacrylate (HEMA), hydroxypropylmethacrylate, glycidylmethacrylate and its derivatives; acrylamids and/or alkylaminomethacrylamid and its derivatives; cyanoacrylate, di(meth)acrylate, tri(meth)acrylate, terta(meth)acrylate, poly(ethyleneglycol)methyl ether acrylate and its derivatives; styrene and its derivatives; parachlorostyrene, pentafluorostyrene, N-vinylpyrrolidone, 4-vinylpyridin, 2-vinylpyridin, vinyl halide, (meth)acryloyl halide, di-vinylbenzene, and vinylic cross-linker based on (meth)acrylate or styrene or its derivatives.

According to a very preferred embodiment, the radical polymerizable monomer is selected from any radical polymerizable alkene comprising (meth)acrylate, styrenic, acrylamide or diène and derivatives thereof; preferably the radical polymerizable monomer is (meth)acrylate based monomer; more preferably is poly(ethyleneglycol)methyl ether acrylate or hydroxyethylmethacrylate.

According to one embodiment, the radical polymerizable monomer provides any structure and/or chain conformation comprising linear, block, random, gradient, star, graft or "comb", hyperbranched or dendritic (co)polymer. According to one preferred embodiment, the polymer has no linear chain conformation.

According to one embodiment, the molar molecular weight of the polymerizable monomer is ranging from 100 Da to 10 kDa, preferably from 400 Da to 6 kDa, more preferably is equal to 480 Da, 2 kDa or 5 kDa.

The amount of polymerizable monomer in the solution used in the process of the present invention may vary as desired by the experimenter. Variations of this amount may participate to the control of the molecular weight of the grafted polymer. According to one embodiment, the concentration of polymerizable monomer in the solution used in the process of the present invention is preferably from below 0.1 mol/L, more preferably from $5.10^{-2}$ mol/L to $10^{-6}$ mol/L.

Preferably, the monomer is pharmaceutically acceptable.

The process of the present invention is carried out under gentle and non-destructive conditions, preferably under normal conditions of temperature and pressure.

According to one embodiment, the porous solid to be grafted is immersed the solution used in the process of the invention. According to another embodiment, the solution is sprayed onto the outer surface of the porous solid.

According to one embodiment, the reaction is performed during a period of time ranging from 5 min to 90 min, preferably from 10 min to 30 min.

According to an embodiment, the reaction time may be adjusted. This adjustment of the time of exposure of the surface of the material to the polymer-precursor solution makes it possible to control the size of the polymeric chain that is obtained and thus the molecular weight of the polymer.

According to one embodiment, the efficiency of the grafting may be determined by any suitable means of analysis, especially by X photoelectron spectroscopy (XPS) measurements. According to one embodiment, XPS analysis may be performed using a Kratos XPS apparatus.

According to another embodiment, the outer surface of the porous solid may be pre-treated by an acidic treatment, or an oxido-reductive treatment. According to a specific embodiment, the outer surface of the porous solid may be activated by KF-treatment, for example by dispersing the porous solid in a KF solution.

According to one preferred embodiment, the process of the present invention is carried out under normal conditions of temperature and pressure; in water, and comprises:
  iron powder as reducing agent,
  4-nitrobenzene diazonium salt as adhesion primer,
  Poly(ethyleneglycol)methyl ether acrylate or hydroxyethylmethacrylate as monomer.

Use of the Modified Porous Solid

The invention further relates to the use of the modified porous solids of the invention; preferably the use of the modified MOF solids.

According to one embodiment, the modified porous solid may be used to for gas storage, liquid adsorption, fluid separation, catalysis.

According one embodiment, the modified porous solid of the invention may be used as a contrast agent and/or for carrying pharmaceutical compounds. Moreover, it may be used for applications in the cosmetic field. It may also be used for vectorizing and/or monitoring pharmaceutical compounds in a body.

According to one embodiment, the modified porous solid of the invention comprises in its pores or at its surface at least one pharmaceutically active principle and/or an active substance suitable for its formulation in a cosmetic product and/or a marker.

The Applicant has demonstrated that the particular structural characteristics of the solid of the present invention, especially in terms of flexibility or pore size, give it particularly advantageous properties, especially in terms of adsorption capacity, selective adsorption and purity. These materials thus enable the selective adsorption of molecules, for instance pharmaceutical molecules, with a favorable energy cost and a longer release time. Thus, the research studies conducted by the Applicant have enabled them to demonstrate the advantage of MOF materials for adsorbing and carrying active principles.

Thus, the invention also relates to the use of the porous solid, preferably MOF solid, according to the invention, which comprises in its pores or at its surface at least one pharmaceutically active principle.

Especially, the invention relates to the use of the porous solid, preferably MOF solid, according to the invention loaded with pharmaceutically active principle as a medicament. The pharmaceutically active principle may be contained either in the pores or at the surface of the solid according to the invention. This is what is understood in the rest of this document by the expression "porous or MOF solid loaded with pharmaceutically active principle".

More generally, the term "porous or MOF solid loaded with component Y" refers to a porous or MOF solid according to the invention containing in its pores or at its surface the component Y. The component Y may be adsorbed or bound by covalent bonding, by hydrogen bonding, by Van der Waals bonding, by electrostatic interaction at the surface or in the pores of the porous or MOF solid. This component Y may be, as indicated above, a pharmaceutically active principle.

In the present invention, the term "active principle" refers to a molecule possessing a therapeutic effect. For example, the active principle can be any molecules having therapeutic properties used in a medicament. The active principle can be, for example, non-steroidal antiinflammatories (NSAIDs), abortive agents, alpha blockers, alpha2-agonists, aminosides, analgesics, anesthetic, local anesthetic, anorectics, 5HT3 antagonists, calcium antagonists, antianginals, antiarrythmics, antibiotics, anticholinergics, anticholinesterase agents, antidiabetics, antidiarrhoeals, antidepressants, antihistamines, antihypertensive agents, antimycotics, antimalarials, antiparasitics, antipsychotics, antipyretics, antiretrovirals, antiseptics, antispasmodics, antivirals, antiemetics, antiepileptics, anxiolytics, barbiturates, benzodiazepines, bronchodilatators, beta-blockers, chemotherapeutics, corticosteroids, diuretics, loop diuretics, osmotic diuretics, depressants, glucocorticoids, hallucinogenics, hypnotics, immunosuppressants, anhydrase carbonic inhibitors, neuraminidase inhibitors, proton pomps inhibitors, TNF inhibitors, serotonin reuptake selective inhibitors, HMG-CoA reductase (or statins) inhibitors, keratolytics, laxatives, mineralocorticoids, myorelaxants, neuroleptics, psychotropics, spasmolytics, stimulating agents, sedatives, tocolytics or vasodilating agents. This list is non-exhaustive and can be extended to any therapeutic active principle known by the skilled artisan.

Indeed, the modified porous solid, in particular MOF solid, according to the invention presents the advantage of possessing high capacities of adsorption or load. Indeed, the solid of the present invention possesses an internal microenvironment hydrophobic/hydrophilic favorable.

In addition, it can efficiently adsorb pharmaceutical molecules that have particular encapsulation difficulties, for example on account of their instability, their high reactivity, their poor solubility, their strong tendency to crystallize, their hydrophilic or amphiphilic nature.

For example, the solid according to the invention may be loaded with at least one pharmaceutically active principle that has one or more of the following characteristics: hydrophilic, amphiphilic, lipophilic, unstable, toxic, strong tendency to crystallize or substantially insoluble.

The term "toxic" refers to a pharmaceutically active principle that has noxious effects liable to hinder its use in medical or veterinary applications. They may be, for example, alkylating agents such as busulfan, cisplatin or nitrosoureas such as lomustine. After metabolization, alkylating agents form covalent bonds with nucleic acids. The formation of these bonds may result in:
 DNA transcription and replication disorders,
 base substitutions in DNA,
 base excisions and DNA chain splitting.

Their main pharmacological activity is manifested during the synthesis phase of DNA. Their toxic effects include: myelosuppression, sterility and non-lymphocytic leukemia.

Cisplatin causes intra-catenary DNA bridging, has low myelotoxicity, but is a powerful emetic and may be nephrotoxic.

The term "strong tendency to crystallize" refers to a pharmaceutically active principle that has a tendency to self-associate in a crystal lattice instead of being included in other structures. Thus, such a compound tends to form crystals during the encapsulation process used, rather than being included in particles. This thus gives at the end of the process a mixture of particles that are poorly loaded with pharmaceutically active principles and crystals thereof. It may be, for example, busulfan. At high dose, it has a serious side effect, namely veno-occlusive liver disease. This probably results from the very strong tendency of this molecule to crystallize. The crystal stacking is governed by strong dipole-dipole interactions between the methylsulfonate groups of this active principle.

The term "substantially insoluble" refers to a pharmaceutically active principle whose solubility is less than 0.1 mg/ml in water. It may be, for example, busulfan.

The term "unstable" refers to a pharmaceutically active principle that can decompose, crystallize and/or react and in so doing lose its structure and its activity. A possible example of this is busulfan.

In addition, the pharmaceutically active principle may be any molecule that has biological activity, for instance a medicament, especially an anticancer agent, an antiviral agent, a modified or unmodified nucleoside analog, a nucleic acid, an antibody, a protein, a vitamin.

Among the hydrophilic active principles that may be mentioned, for example, are azidothymidine phosphate or not (AZTP or AZT), CDV (cidofovir), 5-fluorouracil and citarabine.

Among the amphiphilic active principles that may be mentioned, for example, are busulfan, doxorubicin chloride and imipramine chloride.

Among the lipophilic active principles that may be mentioned, for example, are tamoxifen, docetaxel, paclitaxel, ibuprofen, lidocaine, liposoluble vitamins such as vitamins A (retinol), D (calciferol), E (tocopherol), K1 (phylloquinone) and K2 (menaquinone).

According to one embodiment, the solid according to the invention is loaded with at least one pharmaceutically active principle chosen, for example, from the group comprising taxotere, busulfan, azidothymidine (AZT), azidothymidine phosphate (AZTP), cidofovir, ibuprofen, antibiotics, gemcitabine and tamoxifen, zalcitabine (ddC) and didanosine (ddI).

Advantageously, the solid of the invention may be loaded with at least one pharmaceutically active principle chosen, for example, from the group comprising busulfan, azidothymidine (AZT), azidothymidine phosphate (AZTP), cidofovir, gemcitabine and ibuprofen.

In addition, the solid according to the invention may be loaded with at least one compound of cosmetic interest.

The term "compound of cosmetic interest" refers to any active substance included in the formulation of a cosmetic preparation, i.e. a preparation intended to be placed in contact with various surface parts of the human body, especially the epidermis, the pilous and hair systems, the external organs, the teeth and mucous membranes, for the purpose, exclusively or mainly, of cleaning, protecting or fragrancing them, maintaining the human body in good condition, modifying its appearance or correcting its odor. The term "active substance" refers to a substance that ensures the efficacy of the cosmetic preparation.

The compound of cosmetic interest may be an active substance included in the preparation of any cosmetic preparation known to those skilled in the art, for example hygiene products (e.g. makeup remover, toothpaste, deodorant, shower gel, soap or shampoo), care products (e.g. anti-wrinkle cream, day cream, night cream, moisturizing cream, floral water, scrub, milk, beauty mask, lip balm or tonic), haircare products (e.g. hair conditioner, relaxer, gel, oil, lacquer, mask or dye), makeup products (e.g. concealer, self-tanning product, eyeliner, makeup powder, foundation, kohl, mascara, powder, skin bleaching product, lipstick or nail varnish), fragrances (e.g. eau de Cologne, eau de toilette or fragrance), antisun products (e.g. after-sun and antisun creams, oils and lotions), shaving products and hair-removing products (e.g. aftershave, hair-removing cream or shaving foam) or bath and shower preparations (e.g. bubble bath, bath oil or bath salts).

According to the invention, the compound of cosmetic interest may be chosen, for example, from the group comprising:
 an antioxidant (for example citric acid, beta-carotene, vitamin E, glycolic acid, glutathione, vitamin C, polyphenols, lycopene, flavonoids, tannins, anthocyans, N-acetylcysteine (free-radical scavenger)),
 a vitamin (for example vitamin A, B3, B5, B6, B2, B1, B9, B8, B12, C, E, D, K, K1, K2),
 a liporegulator (for example caffeine or theophylline),
 a photoprotective agent (for example benzophenone-3(2-hydroxy-4-methoxybenzophenone), benzophenone-4-(2-hydroxy-4-methoxybenzophenone-5-sulfonic acid), 2-phenylbenzimidazole-5-sulfonic acid),
 a moisturizer (for example urea, hyaluronic acid or sorbitol).

For example, the solid according to the invention may be loaded with at least one compound of cosmetic interest selected from the group comprising benzophenone, visnadine, salicylic acid, ascorbic acid, benzophenone and derivatives thereof, caffeine, urea, hyaluronic acid, etc.

According to the invention, the grafted polymer may be functionalized by a fluorescent molecule. For example it may be rhodamine (for example rhodamine B), fluorescein, luciferase, pyrene and derivatives thereof, aminopyrrolidino-7-nitrobenzo-furazan or quantum dots.

For example, quantum dots may be chosen form a group comprising cadmium selenide, cadmium sulfide, indium arsenide, indium phosphide, and cadmium selenide sulfide.

In one embodiment, the active principle may be a fluoro molecule, i.e. a molecule comprising at least one substituent F. It may be, for example, one of the fluoro molecules mentioned previously. These fluoro molecules are suitable for use in imaging, particularly fluorescence imaging such as the abovementioned PET technique. In this case, the $^{18}$F isotope may be used.

Thus, the invention also relates to the use of porous solids, preferably MOF nanoparticles, encapsulating one or more fluoro molecules according to the invention, as marker that may be used in medical imaging, such as PET imaging.

According to one embodiment, the solid according to the invention may be loaded with pharmaceutically active principle with a loading capacity from 1% to 200% by weight of dry solid, for example from 1% to 70% by weight of dry solid, i.e. close to 10 to 700 mg per gram of dry solid.

In the context of the present invention, the loading capacity refers to the capacity for storing molecules or the amount of molecules adsorbed into the material. The loading capacity may be expressed as a mass capacity (gram/gram) or as a molar capacity (mol/mol) or in other terms (mol/gram, gram/mol).

Indeed, the grafting with polymers having a size higher than the size of the access window to the pores of porous materials, allows obtaining stable coating while avoiding to disturb encapsulated molecules.

In addition, another problem of the prior art relates to the rapid and uncontrolled release of the carried molecules in the absence of affinity. The modified MOF solid according to the invention has the advantage of allowing longer release times, especially by virtue of the internal microenvironment, but also by virtue of the structure of the compounds.

The solid according to the invention may further comprise, for example on the spacer ligands, functional groups that can modify the interactions between the porous solid according to the invention and the molecule of interest. This may make it possible to control the encapsulation and release of the molecules of interest. The porous materials of the invention may thus be adapted and formulated ("designed") as a function of the molecules of interest to be carried so as to modify the degree of encapsulation, the release of the molecules and/or the degradability of the solid.

The porous solid of the present invention used for carrying active principles makes it possible to overcome the prior art problems mentioned previously, especially the problems associated with the instability of the coating of the porous vehicle, notably in biological medium, and to its interference with the release of molecules encapsulated into the pores of MOFs having modified external surface.

Thus, the present invention also relates to a medicament, a pharmaceutical composition or a medical device comprising a modified porous solid with an outer surface modified by a polymer; preferably, comprising a modified MOF solid with an outer surface modified by a polymer.

In addition, the porous solid according to the invention makes it possible to incorporate markers into this material, which is also an advantage.

Thus, according to one particular embodiment, the solid according to the invention may be loaded with at least one molecule of interest, which may be a pharmaceutically active principle and/or a compound of cosmetic interest and/or a marker. The molecule of interest may be contained either in the pores or at the surface of the solid according to the invention.

Thus, the modified porous solids according to the invention may be used for the manufacture of medicaments, pharmaceutical or cosmetic compositions, medical device and/or markers that may be used in medical imaging.

Thus, a process is provided for treating an individual suffering from a disease, said process comprising the administration to said individual of a modified porous solid according to the invention comprising in its pores or at its surface at least one active principle known for treating said disease.

According to one embodiment, the modified porous solid according to the invention may be loaded with at least one marker selected from the group comprising a medical imaging marker, a contrast agent, a tracer, a radioactive marker, a fluorescent marker and a phosphorescent marker.

Surface modification using a fluorescent compound may be performed, especially with a monomer, an oligomer or a polymer, preferably cyclodextrin or polycyclodextrin, marked with rhodamin or fluorescein.

The modified MOF solids of the invention marked with fluorescents compounds may be used in fluorescence imaging.

According to one embodiment, the solid according to the invention may be loaded with at least one marker selected from the group comprising: a fluorescent compound, an iron oxide, a gadolinium complex, gadolinium ions directly present in the structure, for example in the form of a complex with the organic ligand. The protocols for loading with marker are those known to a person skilled in the art. Non-limiting examples that may be used are described, for example, in A. K. Gupta, et al., Nanomed. 2007 2(1), 23-39; in P Caravan, Chem. Soc. Rev., 2006, 35, 512-523; or in Yan-Ping Ren, et al., Angew, Chem. Int. Ed. 2003, 42, 5, 532.

Thus, the modified MOF solid according to the invention may be used for manufacturing, carrying and/or vectorizing markers.

In addition, the modified MOF solid of the invention may be used for vectorizing medicaments when it is loaded with pharmaceutically active principle and/or for detecting and monitoring diseases involving biological targets (such as cancer) when it is used as a marker.

In addition, by cumulating these two uses, the solid of the present invention advantageously makes it possible to visualize the biodistribution of a medicament. This is of great interest, especially for monitoring a therapeutic treatment and for studying the biodistribution of a medicament.

The modified porous solids of the present invention thus constitute improved compounds capable of featuring different properties depending on the specific uses of said compounds. Advantageously, said properties may be escaping the immune system (i.e. stealth) taken up by the targeted organs, avoiding to accumulate in the reticuloendothelial system, increasing their blood circulation half-life, improving bioadhesion, imaging and/or vectorizing active principle to specific targets.

The improved method of modification of the porous solid surface disclosed in the present application allows:
   to guarantee a better stability of the coating in biological medium,
   to not interfere with the encapsulation and release of active molecules intended to be vectorized by said MOF material, thanks to porosity retaining.

The modified porous solids of the invention are capable of carrying active principle, for example active principle difficult to encapsulate due to their instability, their strong tendency to crystallize, their poor solubility, their hydrophilic or amphiphilic nature.

Moreover, these compounds allow the controlled release of active principle.

EXAMPLES

Figure 1:
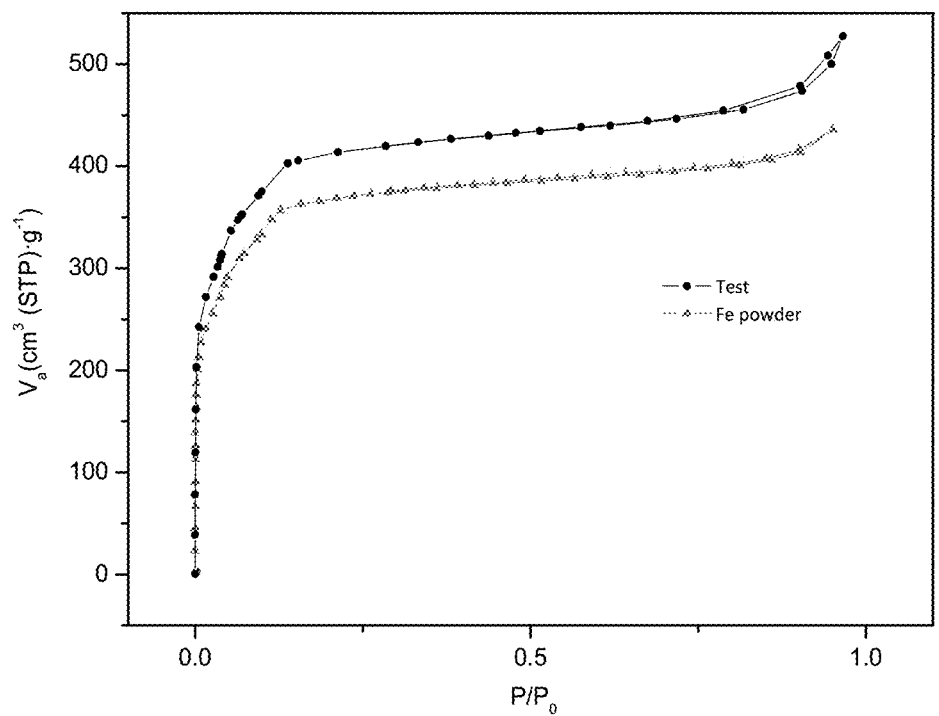
FIG. 1 is a $N_2$ adsorption isotherm at 77 K of MIL-100 (Fe) nanoparticles incubated in: HCl 50 mM (black circles); $Fe^0$ powder and HCl 50 mM (light-gray triangles); and HCl 50 mM (dark-gray stars). Activation of the pores was performed by outgassing at 180° C. for 3 h.

The present invention is further illustrated by the following examples.

Material

Iron (III) chloride hexahydrate (97%), trimesic acid (95%), Aluminum nitrate nonahydrate, 4-nitrobenzenediazonium tetrafluoroborate, iron powder (≥99%), zinc nitrate hexahydrate, phosphate buffered saline (PBS) solution (0.01 M, pH=7.4) and poly(ethylene glycol) methyl ether acrylate, abbreviated as acryl-PEG, with a Mw of 450 Da (acryl-$PEG_{450\,Da}$), 2 kDa (acryl-$PEG_{2\,KDa}$) and 5 kDa (acryl-$PEG_{5\,KDa}$) were purchased from Sigma-Aldrich. 2-methylimidazole was purchased from Alfa Aesar. All materials were used as received without further purification.

Synthesis of MIL-100(Fe) Nanoparticles and MIL-100 (A1) Nanoparticles. The synthesis was performed by microwave-assisted hydrothermal synthesis according to a previously reported procedure (Garcia-Marquez et col. in *Eur. J. Inorg. Chem.* 2012, 5165).

Synthesis of MIL-100(Fe) Nanoparticles. Iron(III) chloride hexahydrate (2.43 g) and trimesic acid (0.84 g) were dissolved in 20 mL of MilliQ water into a Teflon lined autoclave. After vigorous stirring for 10 min, the mixture was sealed and heated at 130° C. for 5 min in a microwave oven (at 400 W; Mars-5, CEM) with a heating temperature of 1 min. The nanoparticles were recovered by centrifugation (10,500 rpm, 20 min).

Activation 1: Activation or purification of 2.5 g of MIL-100(Fe) consisted of the redispersion and centrifugation (10500 rpm, 20 min) of the nanoparticles in 20 mL of MilliQ water. This procedure was repeated twice in MilliQ water and five successive times in 20 mL of ethanol.

Activation 2: Activation or purification of 2.5 g of MIL-100(Fe) consisted of the re-dispersion and centrifugation (10500 rpm, 20 min) of the nanoparticles in 20 mL of MilliQ water. This procedure was repeated twice in MilliQ water and five successive times in 20 mL of ethanol. Further activation was carried out by re-dispersing the solid in 20 mL of a 0.1 M KF solution. The mixture was kept under magnetic stirring for 1 h 40 min under ambient conditions Immediately after, nanoparticles were collected by centrifugation (10500 rpm, 20 min) and washed twice with 20 mL of distilled water and once with 20 mL of ethanol following the process described above. Activated MIL-100(Fe) nanoparticles were isolated by centrifugation (10500 rpm, 20 min) and stored wet with few droplets of fresh ethanol to avoid complete drying of the product.

Synthesis of MIL-100(Al) Nanoparticles. Aluminum nitrate nonahydrate (1.43 g) and trimethyl trimesate (1.21 g) were dissolved in 20 mL of MilliQ water under vigorous stirring, followed by the addition of 4 mL of nitric acid. The reaction mixture was stirred for 5 min at room temperature and then introduced into the microwave oven. After hydrothermal treatment at 210° C. (1600 W), the resulting mixture was cooled down in an ice bath and the yellow-coloured solid recovered by centrifugation (10500 rpm, 20 min)

Activation of the nanoparticles was performed by redispersion in 50 mL of methanol and vigorous stirring overnight. Nanoparticles were isolated by centrifugation (10500 rpm, 20 min) and stored wet with few droplets of fresh methanol to avoid complete drying of the product.

Synthesis of ZIF-8 Nanoparticles. A solution of zinc nitrate hexahydrate of $Zn(NO_3)_2 \cdot 6H_2O$ (1.467 g) in 100 mL of methanol was rapidly poured into a solution of 2-methylimidazole (3,245 g) in 100 mL of methanol under vigorous stirring at room temperature. The mixture slowly turns turbid and after 1 h the nanoparticles were separated from the milky dispersion by centrifugation (10,500 rpm, 20 min)

The activation was performed readily redispersing the material in absolute ethanol and recovering by centrifugation. Three washing cycles of the redispersion in absolute ethanol and centrifugation were carried out to activate the material. Nanoparticles were isolated by centrifugation (10500 rpm, 20 min) and stored wet with few droplets of fresh ethanol to avoid complete drying of the product.

Physico-Chemical Characterization. X ray powder diffraction (XRPD) were collected in a D8 Advance Bruker diffractometer with Cu Kα1 radiation (lambda=1.54056 angstroms) from 3 to 30° (2θ) using a step size of 0.02° and 4 s per step in continuous mode. Fourier transform infrared (FTIR) spectra were collected using a Nicolet 6700 instrument (Thermo scientific, USA) from 4000 to 400 cm$^{-1}$. $N_2$ adsorption isotherms were obtained at 77K using a BELsorp Mini (Bel, Japan). Prior to the analysis, approximately 30 mg of sample were evacuated at 140° C. under primary vacuum for 3 h. Thermogravimetric analyses (TGA) of the RT samples (5-10 mg) were analyzed on a Perkin Elmer Diamond TGA/DTA STA 6000 under $O_2$ atmosphere (20 mL·min$^{-1}$), at heating speed of 3° C./min for the temperature range between RT and 600° C. (note: acryl-PEG wt % is given with respect to dryMIL-100(Fe) weight). Particle size and ζ-potential was monitored by Dynamic Light Scattering (DLS) Electrophoretic Light Scattering (ELS), respectively, on a Zetasizer Nano (Malvern Instruments). Samples were prepared by dispersing the room temperature nanoparticles at 0.1 mg·mL$^{-1}$ in the desired media by the use of an ultrasound tip (10% amplitude for 1 min; Digital Sonifer 450, Branson). XPS: X-ray photoelectron spectroscopy (Kratos Axis Ultra DLD AlKα monochromatic source.

Methods

Calculations Regarding the Amount of Acryl-PEG$_{480}$ on the MIL-100(Fe) Nanoparticle. As discussed in the main text, TGA characterization of MIL-100(Fe) nanoparticles coated with acryl-PEG$_{480}$ determined a presence of 30±1 wt % of the polymer in the sample. That is, in 100 g of nanoparticles there are 30 g of PEG.

Volume of the uncoated nanoparticle: The average size of the nanoparticles is 147.9 nm, as determined by DLS. Then, the volume of a single nanoparticle is 1693960 nm$^3$.

Number of nanoparticles in 100 g sample: The unit cell of MIL-100(Fe) contains 1152 Fe atoms and has a lattice parameter of 7.234 nm. The volume of the unit cell is 377 nm$^3$. Then, if the volume of one nanoparticle (above) is divided by the volume of the cell, it is obtained 4499 u.c./nanoparticle.

The Mw of $Fe_3O(H_2O)_2F(BTC)_2$ is 653 g/mol, and considering the number of Fe atoms in a unit cell, it can be deduced that the mass of a single unit cell is: 1152 Fe atoms·(1 mol MIL-100(Fe): 3 Fe atoms)·(653 g MIL-100 (Fe): 1 mol MIL-100(Fe))=250752 g/mol u.c.

In 100 g of nanoparticles there are 3.988 10$^{-4}$ mol u.c., while considering the Avogadro number, it can be expressed as: 2.40197 10$^{20}$ unit cells in 100 g of MIL-100(Fe). Considering the volume of single cell is 377 nm$^3$ and the volume of a single nanoparticle is 1693960 nm$^3$, it is deduced that 2. 40197 10$^{20}$ unit cells (377 nm$^3$: 1 unit cell) (1 nanoparticle: 1693960 nm$^3$)=5.3457 10$^{16}$ nanoparticles in 100 g of MIL-100(Fe).

Number of acryl-PEG$_{480}$ entities in 30 g: The Mw of the polymer is 480 Da. Therefore, in 30 g there are 3.7644 10$^{22}$ polymer chains.

Number of acryl-PEG$_{480}$ entities per nanoparticle: From the values obtained above, it is determined that there are 704188 acryl-PEG480 entities per nanoparticle.

Density of acryl-PEG$_{480}$ entities on the nanoparticle: The external surface of a single nanoparticle is 68751 nm$^2$. Therefore, 704188:68751=10 acryl-PEG480 entities/nm$^2$.

Example 1

Determination of Graftfast Experimental Conditions for MOF Outer Surface Modification in the Absence of Monomer First studies were devoted to the initial evaluation of MOF nanoparticles (nanoMOFs) stability against GraftFast experimental conditions.

According to an embodiment, GraftFast method involves the impregnation of the material to be modified with a reducing agent in acidic medium—conditions enabling the formation of radical entities to start with the radical polymerization process—and the reaction mixture is left to react over a given time under environmental conditions followed by rinsing steps to remove the excess of unreacted species. These are well-established conditions already described for other types of nanomaterials, including carbon nanotubes (*J. Mater. Chem.* 2011, 21, 4615) and titanium oxide nanoparticles (*J. Mater. Sci.* 2011, 46, 6332).

NanoMOF stability tests were performed against two different reducing agents (orthophosphoric acid and iron powder) in a hydrochloric acid 1-50 mM medium over a period of 30 minutes. Afterwards, nanoparticles were collected by centrifugation and subsequently characterized by complementary techniques for comparison with the as-synthesized nanoparticle equivalents. For the present study, two different nanoMOFs were studied: the iron(III) carboxylate of the MIL-100(Fe) structure (MIL standing for Material from Institute Lavoisier) and the zinc imidazolate of the structure ZIF-8 (ZIF stands for zeolitic imidiazole framework). Both types of nanoMOFs were synthetized according to previously reported procedures (Eur. *J. Inorg. Chem.* 2012, 5165; and *J. Mater. Chem.,* 2010, 20, 7676).

X-ray diffraction (XRD) and FT-IR data indicated good stability for both nanoMOF species under the tested conditions against iron metal powder reducing agent.

The stability of nanoMOFs was evaluated more in detail to detect possible changes in size, ζ-potential, specific surface area and composition by performing dynamic light scattering (DLS), $N_2$ adsorption desorption isotherms and thermogravimetric analyses (TGA). As-synthetized MIL-100(Fe) nanoparticles presented an average size of 171.4±14.7 nm and ζ-potential of +12.4 mV. Incubation of nanoparticles in a solution of HCl 50 mM for 30 minutes in absence of reducing agent gave to virtually identical in-size nanoparticles with but ζ-potential shifted towards negative values, assigned to the presence of chloride anions on the nanoparticle external surface (Table 1). The presence of iron powder during incubation do not altered the nanoparticles and changes in the values are within the experimental error. Table 2 shows the equivalent study for the ZIF-8 nanoparticles. In this case, nanoparticles were unaltered after incubation with iron metal powder. This observation together with the almost neutral value of ζ-potential suggested a possible aggregation of the nanoparticles.

TABLE 1

Size and ζ-potential data for MIL-100(Fe) nanoparticles incubated in different media during 30 min under stirring.

| Incubation media | Avg size (nm)* | ζ-potential (mV)* |
|---|---|---|
| none | 171.4 ± 14.7 | +12.4** |
| 50 mM HCl | 182.8 ± 21.6 | −28.6 |
| Fe⁰ powder and 50 mM HCl | 134.2 ± 18.4 | −23.1 |

*Size and ζ-potential are determined by dispersing the nanoMOFs at 0.1 mg · mL$^{-1}$ in water by the use of ultrasounds.
**Note that uncoated nanoparticles (activation 1) displayed a positive surface charge.

TABLE 2

Size and ζ-potential data for ZIF-8 nanoparticles incubated in different media during 30 min under stirring.

| Incubation media | Avg size (nm)* | ζ-potential (mV)* |
|---|---|---|
| none | 66.2 ± 9.8 | +25.2** |
| Fe⁰ powder and 50 mM HCl | 76.0 ± 7.4 | +31.7 |

*Size and ζ-potential are determined by dispersing the nanoMOFs at 0.1 mg · mL$^{-1}$ in water by the use of ultrasounds.
**Note that uncoated nanoparticles (activation 1) displayed a positive surface charge.

Figure 2:
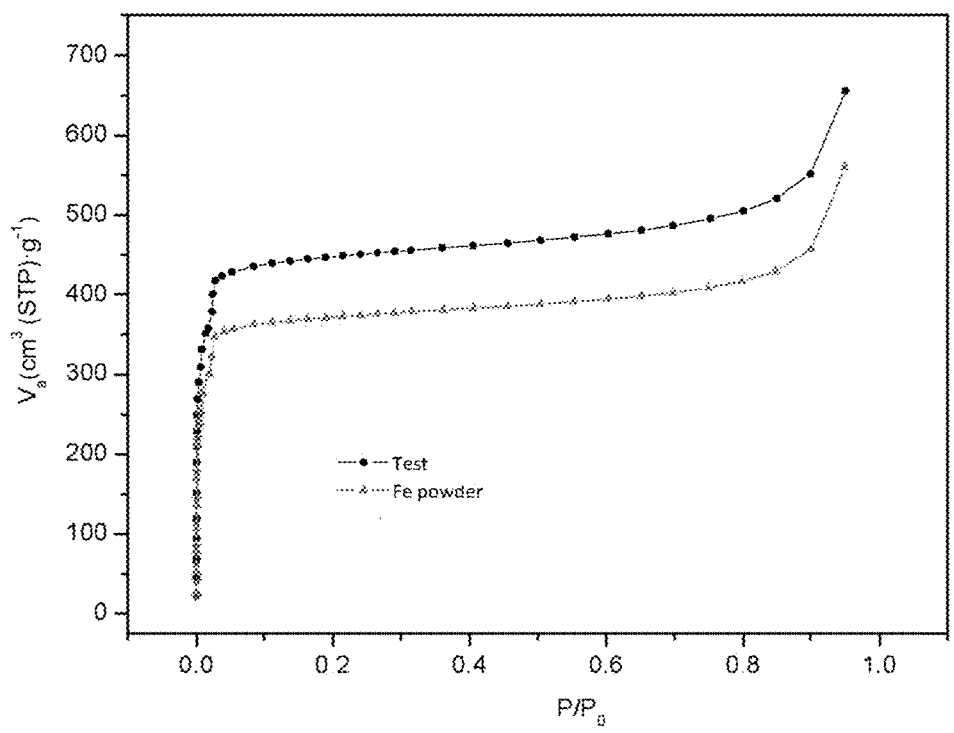
FIG. 2 is a $N_2$ adsorption isotherm at 77 K of ZIF-8 nanoparticles incubated in: HCl 50 mM (black circles); $Fe^0$ powder and HCl 50 mM (light-gray triangles); and HCl 50 mM (dark-gray stars). Activation of the pores was performed by outgassing at 160° C. for 3 h.

Due to the porous nature of the nanoMOFs under study, the presence of the reducing agents during incubation step might have an impact on the porosity of the nanoparticles, either by intrusion of the reducing agents inside the porous system or the blockage of the windows that give access to the internal cavities due to the localization of the reducing agents on the external surface of the nanoparticle. To address this issue, $N_2$ adsorption desorption isotherms were carried after incubation in the presence and absence of the reducing agents. As shown in FIG. 1, MIL-100(Fe) nanoparticles exhibited similar BET surface area values after incubation in HCl 50 mM medium alone (1300 m$^2$·g$^{-1}$) and in the presence of iron powder (1125 m$^2$·g$^{-1}$). Alternatively, ZIF-8 nanoparticles presented a BET surface area of 1700 m$^2$·g$^{-1}$ after incubation in HCl 50 mM and in the presence of iron powder, of 1475 m$^2$·g$^{-1}$ (FIG. 2). The slight decrease in BET surface area might be minimized by additional washings after GratFast process to remove the excess of reducing agent in the medium. Overall, the results obtained so far suggested the iron metal powder as one of the most favorable candidates to be used as reducing agent for GraftFast with nanoMOFs.

TABLE 3

Overview of the TGA of MIL-100(Fe) nanoparticles after incubation in HCl 50 mM alone or in the presence of iron powder as reducing agent.

| Sample MIL-100(Fe) | w/w % Fe$_2$O$_3$ |
|---|---|
| theoretical value | 37.8 |
| as-synthesized | 37.3 |
| in HCl 50 mM | 36.9 |
| in 50 mM HCl plus Fe⁰ powder | 36.9 |

Comparative Example

Interaction of MIL-100(Fe) nanoparticles with PEG (without Graft Fast) MIL-100 nanoMOFs were incubated 3 h with alpha monomethoxy-omega-amino poly(ethylenglycol) (CH$_3$—O-PEG-NH$_2$ 5000 Da, Iris Biotech), named PEG-amine. Aqueous solutions of PEG-amine were used containing various amounts of polymer. At the end of the incubation the nanoparticles were recovered by centrifugation, washed in water, in order to remove the excess of coating molecules not associated to the matrix and analyzed by XPS. The results are gathered in Table 4.

Traces of N, an atom exclusively belonging to PEG chains, were found on the nanoparticles surface and the C/Fe atomic ratio dramatically increased (7.4 and 12.8 in uncoated and Meo-PEG-NH$_2$ modified MIL-100 nanoMOFs, respectively). The results show the effective presence of PEG chains at the nanoparticles surface.

TABLE 4

Elemental composition of the MIL-100 nanoMOFs surface before and after incubation with PEG-amino aqueous solution as determined by XPS (At % = atomic %).

| | At % | | | | | |
|---|---|---|---|---|---|---|
| Sample | Cl | C | N | O | Fe | Na |
| MOF | 0.88 | 56.88 | 0 | 34.6 | 7.64 | 0 |
| MOF(PEG) | 0.3 | 60.3 | 0.4 | 34.28 | 4.71 | 0 |
| PEG | 0 | 68.92 | 2.7 | 28.38 | 0 | 0 |

Following this incubation method, PEG-amine was associated up to 17 wt % to the nanoMOFs (ref Nature Materials).

However, the surface area of the nanoMOFs was decreased from 1350±100 m$^2$·g$^{-1}$ (Langmuir) before PEG-amine interaction to only 350 m$^2$·g$^{-1}$.

This dramatic decrease of the surface area is in agreement with a partial filling and/or blocking of the pores by PEG chains. PEG chains penetrate into the pores by reptation, their section (~3.1Å$^2$) being smaller compared to the size of the MIL-100 windows.

These studies clearly demonstrate that without the Graftfast Method®, PEG chains contacted with the porous solid, load the pores of MOF. Thus, the Graftfast Method®, is an adapted coating procedure which does not alter the high MOF surface area, necessary for loading molecules of interest.

Example 2

Implementing of the Graftfast Method® with Monomer (Acryl-PEG$_{480}$) on a MOF Solid (MIL-100(Fe)) in Acidic Conditions 2.1. PEG-coating Experimental The process of the invention was initially studied for the coating of MIL-100(Fe) nanoparticles with poly(ethyleneglycol)methyl ether acrylate (Mw 480 Da), referred to as acryl-PEG$_{480}$, and was as follows.

In a first vial, 1 mL of a 10 mg·mL$^{-1}$ dispersion of MIL-100(Fe) nanoparticles in HCl 50 mM solution was prepared by the use of ultrasound probe (note: nanoparticles were initially stored in wet with few droplets of ethanol to avoid complete drying of the product, and weighted wet based on the wet: dry ratio previously determined from nanoparticles dry at 100° C. overnight). The dispersion was kept under magnetic stirring until used. In a second vial, 12 mg of the diazonium salt (4-nitrobenzenediazonium, NBD) in 1 mL of HCl 50 mM was prepared by using ultrasounds. Then, 60 μl of acryl-PEG$_{480}$ was added under stirring. The content of both vials were mixed and stirred for 1 min Immediately after, the magnetic bar was removed and the vial placed on top of a magnetic plate. A tip of a spatula of iron powder was then added to the mixture and the reaction mixture was left to react for 20 min while keeping the vial on its initial position on the magnetic plate to avoid excessive mixing of the iron powder. It should be noted that even though no agitation was applied, any precipitation of the nanoparticles was observed during reaction. Indeed, the formation of $N_2$ bubbles due to GraftFast reaction ensured a smooth agitation overall the process. Nanoparticles were recovered by collecting the liquid with a pipette while avoiding the iron powder that remained on the bottom of the vial. Nanoparticles were centrifuged (10500 rpm, 20 min) and washed four times with 2 mL of distilled water and 1-2 times with absolute ethanol. Nanoparticles were stored either dry or wet with a few droplets of fresh absolute ethanol. Dry nanoparticles were easily re-dispersed in water by using ultrasounds (note that uncoated nanoparticles cannot be re-dispersed after drying).

In parallel, a similar reaction was performed without adding the diazonium salt (4-nitrobenzenediazonium, NBD) and the iron powder in order to compare with the graft-fast conditions.

2.2. Physico-chemical Characterization

Figure 3:
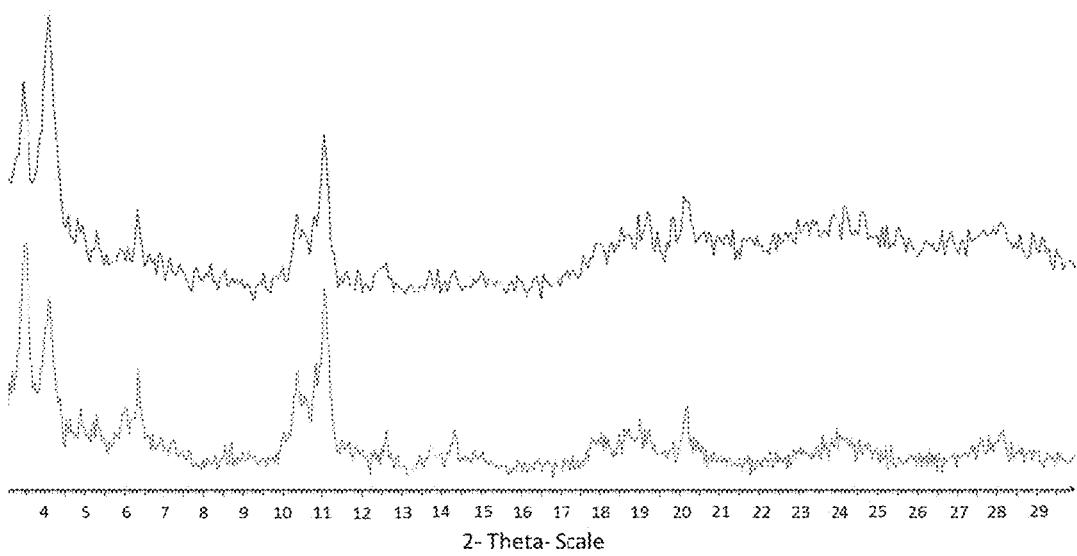
FIG. 3 is XRPD patterns of uncoated (on the bottom) and acryl-$PEG_{480}$-coated (on the top) MIL-100(Fe) nanoparticles by GraftFast.

Preservation of the crystalline MIL-100(Fe) after the Graft-fast reaction was confirmed by X-ray powder diffraction (FIG. 3).

The size of the nanoparticles, before and after surface modification was examined by dynamic light scattering (DLS) in water (Table 5). Interestingly, an increase in size of 30 nm after GraftFast was detected, in agreement with the presence of a coating 15 nm-thick around the nanoparticle. However, no changes in size were observed when nanoparticles were incubated with acryl-$PEG_{480}$ without using GraftFast mechanism (i.e. absence of reducing agent and diazonium salt). The results included in Table 4 also indicates the preservation of the size of uncoated nanoparticles after washing using the cycles with water and ethanol used to remove the free-polymer and non-reacted species during GraftFast. Additionally, the ζ-potential indicated a shift of the surface charge towards negative values. However, the change in the value was already observed during incubation of the nanoparticles in HCl (see above).

TABLE 5

Size and ζ-potential data for MIL-100(Fe) nanoparticles uncoated and treated under GraftFast conditions.

| Sample | Avg size (nm)* | ζ-potential (mV)* |
|---|---|---|
| uncoated | 147.9 ± 14.5 | +29.3** |
| uncoated washed as GraftFast conditions (water and ethanol) | 138.1 ± 28.7 | +29.8 |
| incubated with acryl-$PEG_{480}$ in HCl 50 mM (without the $Fe^0$ and diazonium salt) | 146.8 ± 10.3 | −29.1 |
| after GraftFast | 176.2 ± 3.1 | −29.1 |

*Size and ζ-potential are determined by dispersing the nanoMOFs at 0.1 mg · $mL^{-1}$ in water by the use of ultrasounds.
**Note that uncoated nanoparticles (activation 1) displayed a positive surface charge.

Further evidences on the presence of the polymer were obtained by Fourier transform infrared spectroscopy (FT-IR) before and after acryl-$PEG_{480}$ coating, and after incubation of the uncoated nanoparticles in HCl 50 mM in the presence of the diazonium salt. In addition to the characteristic bands assigned to MIL-100(Fe) structure (υ(C=O) carboxylate at 1577 $cm^{-1}$ and 1450 $cm^{-1}$), the acryl-$PEG_{480}$-coated nanoparticles exhibited additional bands assigned to the presence of the polymer (υ(C—H) alkane 3000-2840 $cm^{-1}$; υ(—O—$CH_3$) 2850-2815 $cm^{-1}$; υ(C=O) aliphatic ester 1750-1735 $cm^{-1}$; υ(—C—O—C—) ether 1150-1085 $cm^{-1}$).

Figure 4:
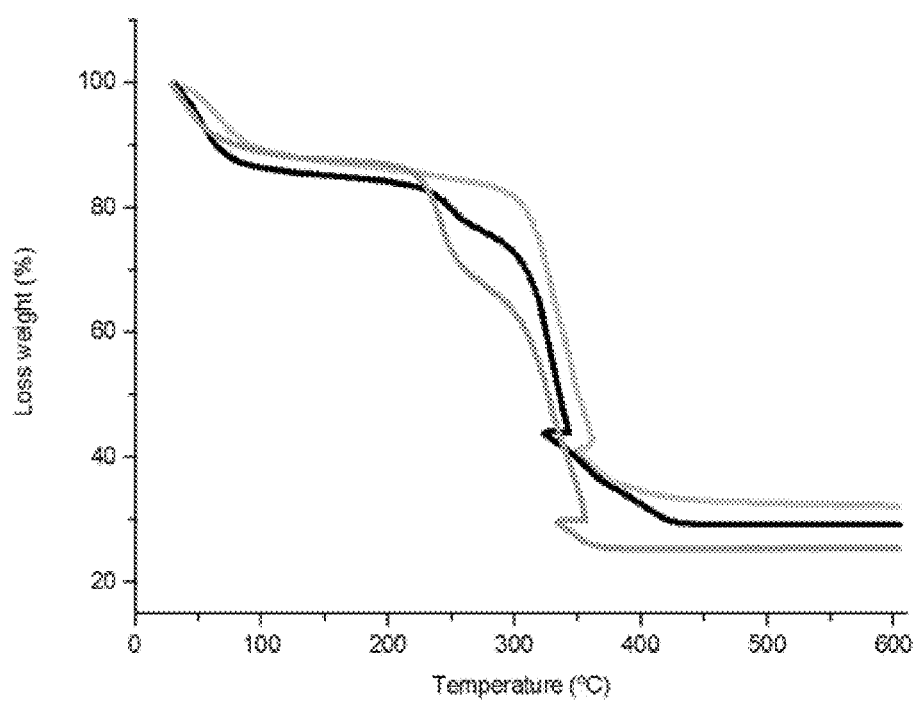
FIG. 4 is TGA of MIL-100(Fe) nanoparticles uncoated (clear gray); acryl-$PEG_{480}$-coated by GraftFast (dark gray); and acryl-$PEG_{480}$-coated by simple incubation of the nanoparticles (black) in a 50 mM HCl solution containing the polymer (without the $Fe^0$ and diazonium salt).

The amount of polymer associated with the nanoparticle was determined by thermogravimetric analyses (TGA, FIG. 4). The presence of an additional weight loss step at ~210° C. was in agreement with the presence of acryl-$PEG_{480}$, which typically degrades at 165° C. when isolated. The estimated percentage was 30±1 wt % of polymer in the sample (note: polymer wt % is given with respect to dry MIL-100(Fe) weight). Alternatively, TGA of nanoparticles incubated with the same initial amount of acryl-$PEG_{480}$ in HCl 50 mM but without GraftFast conditions (i.e. absence of diazonium salt and reducing agent) indicated the association of only 9±1 wt % of the polymer in the sample. This result further highlights the efficiency of the GraftFast mechanism.

Once evidenced the presence of acryl-$PEG_{480}$ in the sample after GraftFast mechanism, the localization of the polymer either on the nanoparticle surface and/or partially incorporated inside the porous nanoparticle was examined Presumably, GraftFast is expected to promote the selective grafting of the polymer on the surface while avoiding intrusion into the nanoparticle cavities. Basically, two main features of GraftFast that hamper polymer intrusion can be identified, namely: (i) the radical interaction of the polymer with the MOF surface (strong interaction); and (ii) the increase in size of the final polymer with respect to the accessible windows of the nanoMOF as a result of the radical polymerization process (avoid intrusion).

Figure 5:
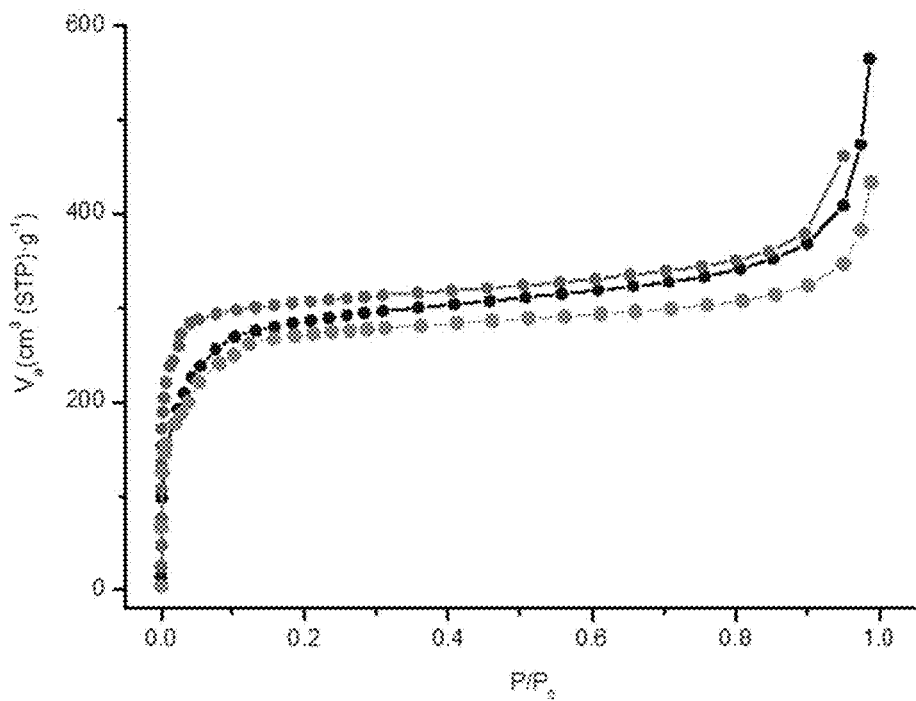
FIG. 5 is $N_2$ adsorption isotherm of MIL-100(Fe) nanoparticles uncoated (black); acryl-$PEG_{480}$-coated by GraftFast without (clear gray) and with weight correction (dark gray). Samples were subjected to outgassing conditions at 140° C. for 3 h.

To address this issue, $N_2$ adsorption isotherms were carried out at 77 K before and after coating (FIG. 5), showing the complete preservation of nanoMOF porosity after GraftFast and confirm the capability of this grafting mechanism to efficiently modify the external surface of this type of porous nanoparticles while restricting the localization of the polymer on the surface and thus preserving intact their initial porosity.

Additionally, considering that the totality of the amount of polymer in the sample was located on the outer surface of the nanoparticle, one can estimate that around ~70400 acryl-$PEG_{480}$ entities were coating each nanoparticle, which means that the corresponding surface density was 10 acryl-$PEG_{480}$ entities per $nm^2$ (see "METHODS" part above for details in the calculations). The high-dense assembly of the polymer agrees with the radical polymerization process by GraftFast mechanism that might result into several layers of the polymer on top of the nanoparticle surface.

Example 3

Implementing of the Graftfast Method® with Monomer (Acryl-$PEG_{480}$) on a MOF Solid (ZIF-8 Nanoparticles) in Acidic Conditions 3.1. PEG-coating Experimental The external modification of nanoMOF nanoparticles with acryl-$PEG_{480}$ by GraftFast mechanism was also investigated with ZIF-8 nanoparticles. It should be noted that the experimental conditions were similar to the ones used for MIL-100(Fe) nanoparticles, and the procedure was as follows.

In a first vial, 1 mL of a 10 mg·$mL^{-1}$ dispersion of ZIF-8 nanoparticles in HCl 50 mM solution was prepared by the use of ultrasound probe (note: nanoparticles were initially stored in wet with few droplets of absolute ethanol to avoid complete drying of the product, and weighted wet based on the wet: dry ratio previously determined from nanoparticles dry at 100° C. overnight). The dispersion was kept under magnetic stirring until used. In a second vial, 12 mg of the diazonium salt (4-nitrobenzenediazonium, NBD) in 1 mL of HCl 50 mM was prepared by using ultrasounds. Then, 60 µl of acryl-PEG$_{480}$ was added under stirring. The content of both vials were mixed and stirred for 1 min Immediately after, the magnetic bar was removed and the vial placed on top of a magnetic plate. A tip of a spatula of iron powder was then added to the mixture and the reaction mixture was left to react for 20 min while keeping the vial on its initial position on the magnetic plate to avoid excessive mixing of the iron powder. As already observed for MIL-100(Fe) nanoparticles, the colloidal solution during reaction was stable without any precipitation. Indeed, nanoparticles appeared pushed up by the N$_2$ bubbles created by GraftFast reaction [note that ZIF-8 nanoparticles were smaller in-size compared with MIL-100(Fe)]. Interestingly, the color of the reaction changed from pale-yellow (from the diazonium salt) to dark-red during reaction. This observation could indicate the reaction of diazonium salts with heterocyclic nitrogens of the ligand of the MOF solid via azo linkage (diazonium salts easily react with nucleophilic groups), as depicted below:

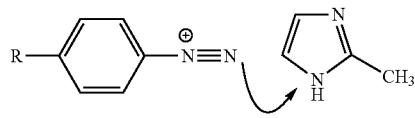

Nanoparticles were recovered by collecting the liquid with a pipette while avoiding the iron powder that remained on the bottom of the vial. Nanoparticles were centrifuged (14500 rpm, 20 min) and washed four times with 2 mL of distilled water and 1-2 times with absolute ethanol. Nanoparticles were stored either dry or wet with few droplets of fresh absolute ethanol. Dry nanoparticles were easily re-dispersed in water by using ultrasounds.

3.2. Physico-chemical Characterization

The crystalline structure of ZIF-8 was maintained after GraftFast reaction, as confirmed by XRPD. The nanoparticles were characterized by DLS to determine the size evolution before and after coating. As shown in Table 6, the size of the particles was slightly increased ~5 nm, however the increase was likely to be within the error of the measurement. In contrast, the ζ-potential experimented a remarkable evolution towards negative values (from +20.6 mV to −36.8 mV). Indeed, this change was not observable when nanoparticles were incubated in HCl 50 mM alone with the reducing agent (Table 2) and could be related with the presence of additional species on the nanoparticle surface. The presence of acryl-PEG$_{480}$ in the sample was suggested by the observation of additional bands in the FTIR spectrum after GraftFast that could be assigned to the polymer, including υ(C—H) alkane 3000-2840 cm$^{-1}$; υ(-O—CH$_3$) 2850-2815 cm$^{-1}$ and υ(-C—O—C—) ether 1150-1085 cm$^{-1}$.

TABLE 6

Size and ζ-potential data for ZIF-8 nanoparticles uncoated and treated under GraftFast conditions.

| Sample | Avg size (nm)* | ζ-potential (mV)* |
|---|---|---|
| uncoated | 60.2 ± 2.6 | +20.6 |
| after GraftFast | 65.2 ± 2.3 | −36.8 |

*Size and ζ-potential are determined by dispersing the nanoMOFs at 0.1 mg · mL$^{-1}$ in water by the use of ultrasounds.

Quantification of the amount of polymer in the sample was performed by TGA. An additional weight loss step was distinguishable after GraftFast at ~240° C. in agreement with the presence of 10±1 wt % of acryl-PEG$_{480}$ (note: polymer wt % is given with respect to dry ZIF-8 weight). Therefore, ~2 wt % of the initial amount of the polymer was grafted on the nanoparticle surface. It should be noted that in this case the step assigned to acryl-PEG$_{480}$ appeared displaced to higher temperatures values with respect to the degradation temperature of the polymer when grafted on MIL-100(Fe) nanoparticles. The displacement of up to 30° C. can be tentatively attributed to the formation of azo linkages between the diazonium salt and imidazole linkers in the ZIF-8 nanoparticles.

Finally, N$_2$ adsorption isotherms were carried out at 77 K before and after GraftFast to determine the effect of the grafting in the intrinsic porosity of the nanoparticles as well as to reveal the localization of the polymer. In this sense, acryl-PEG$_{480}$-coated nanoparticles reached virtually the same capacity than the uncoated counterpart to accumulate N$_2$ inside the internal cavities of the ZIF-8 structure (BET surface area of 1470 m$^2$·g$^{-1}$ and 1340 m$^2$·g$^{-1}$, before and after Graftfast respectively-note that weight correction was applied based on TGA quantification). Therefore, GraftFast succeeded on selectively grafting the polymer on the external surface of the nanoparticles as a coating while ensuring the access to their porosity. On the contrary, the direct incubation of the nanoparticles in a HCl 50 mM solution containing the acryl-PEG$_{480}$ without following GraftFast reaction resulted in a considerable decrease in the porosity of the ZIF-8 nanoparticles (BET surface area was 970 m$^2$·g$^{-1}$).

Example 4

Additional Types of MOF Nanoparticles: The Case of MIL-100(Al)

The efficiency of GraftFast mechanism to selectively functionalize the external surface of nanoMOFs was examined for an additional type of structure, named MIL-100 (Al). The nanoMOF was selected with the aim to compare the results with the MIL-100(Fe) samples and thus evaluate the effect of a different cation on the grafting process. Additionally, aluminium as metallic node opens the way towards the characterization of samples by additional complementary techniques such as NMR.

4.1. PEG-coating Experimental

The experimental procedure was exactly the same as the one used for MIL-100(Fe).

4.2. Physico-chemical Characterization

As already observed with the previous nanoMOFs, the crystalline structure of MIL-100(Al) nanoparticles was preserved after GraftFast reaction, as confirmed by XRDP. However, a completely different behaviour of the nanoparticles was observed in terms of colloidal stability for the particular case of MIL-100(A1). In this sense, nanoparticles appeared aggregated in water but not in HCl 50 mM, in which displayed a size of 95.3±12.7 nm (Table 7). The stability in this medium allowed performing the GrafFast reaction with a well-dispersed colloidal solution and thus ensuring the individual coating of the nanoparticles. It appeared that just when nanoparticles were modified with the polymer by GraftFast reaction they reached enough stability to do not precipitate in water. Both, the enhanced colloidal stability and the observed increase in size of ~35 nm were in line with a successful coating of the nanoparticles.

TABLE 7

Size and ζ-potential data for MIL-100(A1) nanoparticles uncoated and treated under different conditions.

| Sample | Medium during measurement | Avg size (nm)* | ζ-potential (mV)* |
|---|---|---|---|
| uncoated | water | aggregation (up to 650 nm) | −17.0 |
| uncoated | HCl 50 mM | 95.3 ± 12.7 | +25.2 |
| uncoated and washed as GraftFast | water | aggregate (up to 1 μm) | −10.4 |
| incubated with acryl-PEG$_{480}$ in HCl 50 mM | water | aggregate (up to 800 nm) | −10.5 |
| after GraftFast | water | 131.7 ± 2.8 | −22.8 |

*Size and ζ-potential are determined by dispersing the nanoMOFs at 0.1 mg · mL$^{-1}$ by the use of ultrasounds in water or HCl 50 mM (detailed in the table).

TGA presented an additional weight loss at ~245° C. in accordance with the presence of 8±1 wt % of acryl-PEG$_{480}$ in the sample. It should be noted that the step was observed after GraftFast reaction but not when nanoparticles were incubated alone with the polymer in HCl 50 mM. $N_2$ adsorption isotherms carried out at 77 K before and after GraftFast, indicated that even though the presence of the polymeric shell over the nanoparticle, the intrinsic porosity of the MIL-100(A1) was preserved (BET surface area of 1700 m$^2$·g$^{-1}$ and 1650 m$^2$·g$^{-1}$, before and after Graftfast respectively-note that weight correction was applied based on TGA quantification-). Moreover, the porosity was also maintained when nanoparticles were incubated alone with the polymer in acidic conditions (BET surface area 1700 m$^2$·g$^{-1}$).

Example 5

Graftfast Reaction in Non-acidic Aqueous Conditions

In general, GraftFast reaction was optimized for other types of nanomaterials and substrates in acidic conditions. To maintain this condition, the above mentioned approaches were performed in HCl 50 mM. However, MIL-100(Fe) nanoparticles spontaneously acidify the aqueous medium in which are dispersed to a pH in the range of 3.0-3.5 due to the partial deprotonation of the carboxylic acids from the partially coordinated organic linkers of the MOF structure (trimesic acid pKas 3.16, 3.98 and 4.85). This fact suggested the possibility to examine the performance of GraftFast reaction in water without additional acidification of the medium.
5.1. PEG-coating Experimental
The experimental conditions were the same as the ones described in Example 2.1. for PEG-coating of MIL-100(Fe) nanoparticles by GraftFast in acidic conditions but using distilled water instead of HCl 50 mM. It should be noted that MIL-100(Fe) nanoparticles this time were additionally activated by KF-treatment. Details on the synthesis and subsequent activation are included in the "MATERIAL" part above.
5.2. Physico-chemical Characterization
Examination of the size evolution of the nanoparticles before and after coating by GraftFast in distilled water indicated an increase of ~20 nm in-size, in agreement with the presence of the polymeric coating in the sample (Table 8). XRPD indicated the preservation of the crystalline structure of the nanoparticle. TGA was performed for nanoparticles before and after GraftFast as well as after simple incubation in the presence of the polymer in distilled water. An additional weight loss was observed at ~210° C. Interestingly, the degradation temperature matched with the value found for the polymer when associated to the MIL-100(Fe) nanoparticles by GraftFast in acidic conditions (see Example 2.2). The obtained data indicated a presence of 32±1 wt % of acryl-PEG$_{480}$ in the sample. Alternative experiments were performed to quantify the amount of polymer in the sample by additional techniques. In this sense, uncoated and coated nanoparticles were examined by elemental analyses (Table 9).

TABLE 8

Size and ζ-potential data for MIL-100(Fe) nanoparticles uncoated and treated under GraftFast conditions.

| | in HCl 50 mM | | in distilled water | |
|---|---|---|---|---|
| Sample | Avg size (nm)* | ζ-potential (mV)* | Avg size (nm)* | ζ-potential (mV)* |
| uncoated | 147.9 ± 14.5 | +29.3 | 125.9 ± 4.3 | −19.1** |
| uncoated washed as GraftFast conditions | 138.1 ± 28.7 | +29.8 | 128.8 ± 7.3 | −20.5 |
| after GraftFast | 176.2 ± 3.1 | −29.1 | 146.3 ± 2.0 | −29.9 |

*Size and ζ-potential are determined by dispersing the nanoMOFs at 0.1 mg · mL$^{-1}$ in water by the use of ultrasounds.
**Note that uncoated KF-treated nanoparticles (Activation 2) displayed a negative surface charge.

Example 6

Graftfast with PEG Polymers Displaying Different Lengths

The effects of the polymeric grafting are highly dependent on the polymer molecular weight (Mw), chain conformation and density on the nanoparticle surface. GraftFast mechanism can be applied to graft polymers of different lengths in a controlled manner and thus systematically identify the features that each type of coating endows to the nanoparticles. Additionally, the use of other lengths of polymer allows validating the grafting method and demonstrating the generality the process of the invention. To this aim, the following acryl-PEGmonomers displaying different $M_w$ were tested on MIL-100(Fe) nanoparticles: acryl-PEG$_{2kDa}$ (Mw 2000 Da, monomer units ~45), acryl-PEG$_{5kDa}$ (Mw 5000 Da, monomer units ~110) and acryl-PEG$_{480Da}$ for comparison purposes (Mw 480 Da, monomer units ~10).
6.1. PEG-coating Experimental
The experimental procedure followed for the coating with the different PEG chains was the same as the one used for the coating of MIL-100(Fe) nanoparticles with acryl-PEG$_{480Da}$ by GraftFast reaction in distilled water. However, the amount of polymer was adjusted, so the ratio MOF: polymer was reduced for both cases. Acryl-PEG$_{480Da}$ coating was performed with a molar ratio of 1:10, in contrast the amount of acryl-PEG$_{2kDa}$ and acryl-PEG$_{5kDa}$ in the reaction mixture was reduced two factors of magnitude, that is, the molar ratio was set at 10:1. Therefore, the amount of PEG for each polymer length added to 10 mg of MIL-100(Fe) nanoparticles: 60 μl acryl-PEG$_{480\ Da}$, 2.9 mg of acryl-PEG$_{2\ KDa}$ and 7.1 mg of acryl-PEG$_{5\ KDa}$. It should be noted that the solution became lumpy but without precipitation.

6.2. Physico-chemical Characterization

An increase in the size of the nanoparticles was observed by DLS after coating with acryl-PEG of different lengths. Especially, the increment was of ~30 nm and ~40 nm for the acryl-PEG$_{2kDa}$ and acryl-PEG$_{5kDa}$, respectively (Table 9). Both values were in agreement with the presence of the polymeric coating around the nanoparticles. Moreover, the value of the ζ-potential was close to the one obtained with the shorter polymer acryl-PEG$_{480\ Da}$. N$_2$ adsorption isotherms confirmed the preservation of the porosity of the nanoparticles after coating (Table 9).

Quantification of the amount of polymer associated to the nanoparticles was determined by TGA and elemental analyses. An additional weight loss at ~215° C. attributed to the polymer. The presence of acryl-PEG$_{2kDa}$ and acryl-PEG$_{5kDa}$ at 16±1 wt % and 23±1 wt %, respectively, was determined Interestingly, if the number of PEG chains directly grafted to the nanoparticle surface were the same for the three acryl-PEG under study, there should be a proportional relation between the Mw and the amount of polymer in the sample. However, no relationship existed between the two factors (Table 10). This observation might be related to the fact that larger polymeric chains already grafted could hamper the accessibility of other chains to get attached on the nanoparticle surface. In alternative experiments, the samples were examined by elemental analysis to further quantify the amount of polymer. Table 11 shows the data obtained for each case. The calculated amount of polymer from the increase in carbon percentage indicated a presence of 9 wt % and 5 wt % of the acryl-PEG$_{2kDa}$ and acryl-PEG$_{5kDa}$, respectively. The calculated values are below the data obtained by TGA.

TABLE 9

Size and ζ-potential data for MIL-100(Fe) nanoparticles uncoated and treated under GraftFast conditions with acryl-PEG polymers of different lengths.

| Sample | Avg size (nm)* | ζ-potential (mV)* | Amount of polymer (wt %) | BET surface area (m$^2$·g$^{-1}$) |
|---|---|---|---|---|
| uncoated | 125.9 ± 4.3 | −19.1** | — | |
| acryl-PEG$_{480\ Da}$ | 146.3 ± 2.0 | −29.9 | 32 ± 1 | |
| uncoated | 136.8 ± 1.4 | −25.7** | — | 1250 |
| acryl-PEG$_{2\ kDa}$ | 166.2 ± 4.6 | −23.5 | 16 ± 1 | 1230 |
| acryl-PEG$_{5\ kDa}$ | 173.9 ± 8.6 | −23.4 | 23 ± 1 | 1230 |

*Size and ζ-potential are determined by dispersing the nanoMOFs at 0.1 mg·mL$^{-1}$ in water by the use of ultrasounds.
**Note that uncoated KF-treated nanoparticles displayed a negative surface charge.

TABLE 10

Elemental analysis of uncoated, acryl-PEG$_{2\ kDa}$-coated and acryl-PEG$_{5\ kDa}$-coated MIL-100(Fe) nanoparticles.

| | Content (wt %) | | | |
|---|---|---|---|---|
| | C | Fe | F | N |
| Uncoated MIL-100(Fe) | 30.79 | 22.22 | 2.63 | — |
| Acryl-PEG$_{2\ kDa}$ | 54.74 | — | — | — |

TABLE 10-continued

Elemental analysis of uncoated, acryl-PEG$_{2\ kDa}$-coated and acryl-PEG$_{5\ kDa}$-coated MIL-100(Fe) nanoparticles.

| | Content (wt %) | | | |
|---|---|---|---|---|
| | C | Fe | F | N |
| Acryl-PEG$_{5\ kDa}$ | 54.49 | — | — | — |
| Acryl-PEG$_{2\ kDa}$-coated MIL-100(Fe) | 35.48 | 20.12 | 1.43 | <0.30 |
| Acryl-PEG$_{5\ kDa}$-coated MIL-100(Fe) | 33.41 | 21.94 | 2.11 | — |

Example 7

X-ray Photoelectron Spectroscopy (XPS) Characterization

Figure 6:
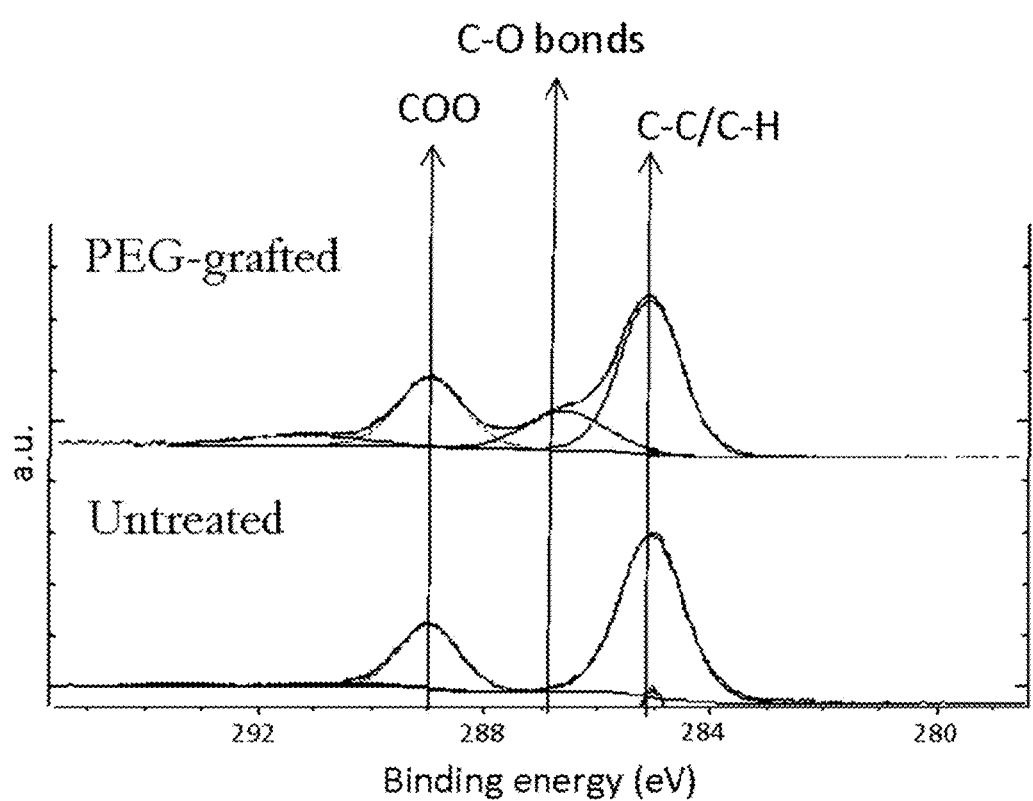
FIG. 6 is a C1s core level XPS spectra of acryl-$PEG_{480}$-coated (top) and uncoated (bottom) MIL-100(Fe) nanoparticles.
Figure 7:
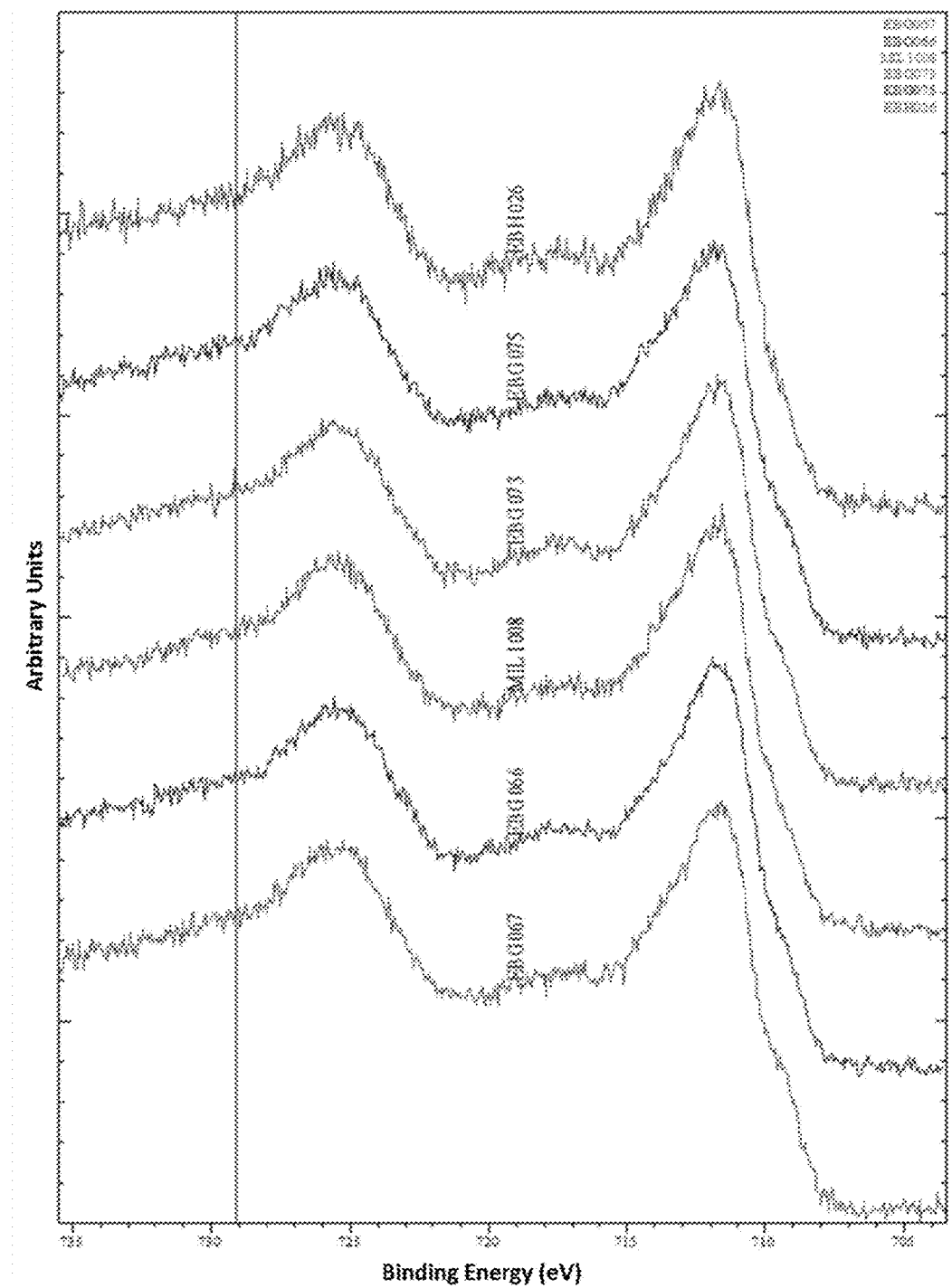
FIG. 7 is a Fe2p/3 core level XPS spectra of acryl-$PEG_{480}$-coated (EBG067, EBG066, EBG073, EBG075 and EBH026) and uncoated MIL-100(Fe) (MIL1008) nanoparticles.

To get more evidences into the nature of the grafting mechanism, nanoparticles coated with the three different PEG lengths were examined by XPS. FIG. 6 displays the data obtained on uncoated and PEG-coated nanoparticles (showing as a representative example the acryl-PEG$_{480Da}$). For uncoated nanoparticles, the C$_{1s}$ core level exhibited two main peak centred at 284.9 eV and 288.9 eV, which are attributed to the C—C/C—H and the COO bonds contained in the organic linker of the MOF structure. For coated nanoparticles, a novel peak centered at 186.5 eV, corresponding to C—O bonds, was observed. The presence of this additional peak was clearly attributed to the presence of the acryl-PEG polymer in the sample. On the other side, the Fe2p/3 core level showed that the chemical environment of the iron was unaltered after GraftFast reaction (FIG. 7).

This result might suggest that the grafting reaction takes place on the organic part of the MOF structure while leaving intact the metallic centers.

Example 8

Degradation Profiles of PEG-coated MIL-100(Fe) Nanoparticles in Simulated Physiological Conditions The influence of the coating on the kinetics of degradation upon immersion in simulated physiological conditions, i.e. water pH 6.3 and serum conditions using phosphate buffered saline (PBS) solution pH 7.4 at 37° C., was assessed by monitoring the release of the organic linker by HPLC. Release of the trimesic acid was monitored in a reversed phased HPLC system Waters Alliance E2695 separations module from Waters with a Sunfire-C18 reverse-phase column (5 μm, 4.6×150 μm from Waters) and equipped with a variable-wavelength photodiode array detector Waters 2998 and controlled by Empower software. The mobile phase used for the measurements consisted of a mixture of 45% v/v methanol in PBS solution (0.04 M, pH 2.5). Injection volume was set at 10 μL, flow rate at 1 mL·min$^{-1}$ and temperature of the column at 25° C. The standards used for the calibration curve consisted of trimesic acid solutions at concentrations of: 25, 12.5, 6.25, 3.13, 1.56, 0.78 and 0.39 μg·mL$^{-1}$. The calibration curve presented a good correlation coefficient ≥0.99. Chromatogram of standards showed a retention time for the organic linker of 4.6 with an absorption maximum at 215 nm. Degradation kinetics of the nanoparticle were obtained in water and PBS at 37° C. according to a previously reported procedure (Chem. Mater. 2013, 25, 2767-2776; J. Mater. Chem. B, 2013, 1, 1101-

1108). The data was represented as the wt % of the linker released, considering the maximum of degradation of 100% when the total amount of the linker was released in the medium.

Figure 8:
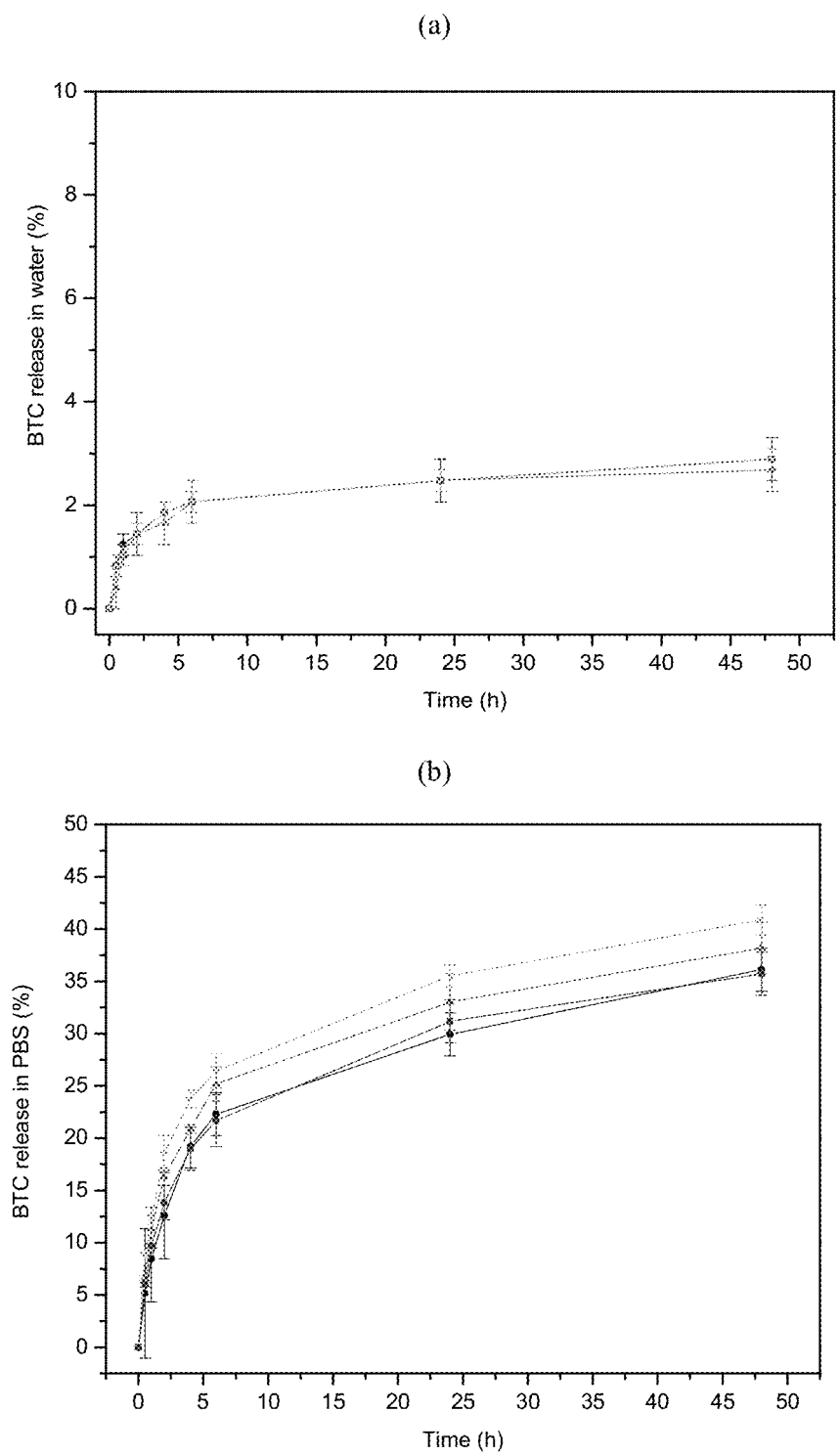
FIG. 8 represents the degradation kinetics of uncoated (black circles); acryl-$PEG_{480Da}$-coated (gray triangles); acryl-$PEG_{2kDa}$-coated (light-gray stars); and acryl-$PEG_{5kDa}$-coated (dark-gray squares) MIL-100(Fe) nanoparticles in (a) water and (b) PBS at 37° C. as a function of time. Degradation is represented as the wt % of the linker released in the medium, considering the maximum of degradation of 100% when the total amount of linker in the nanoparticle was released in the medium.

Similar degradation profiles were observed regardless the presence of the coating for uncoated and acryl-PEG coated nanoparticles, as shown in FIG. 8. Therefore, the presence of the coating does not modify the chemical stability of the nanoparticles.

Example 9

Drug Loading and Release Capacity of PEG-coated MIL-100(Fe) Nanoparticles

The capacity of MIL-100(Fe) nanoparticles to encapsulate and release biological relevant cargoes through post-impregnation was examined by using the challenging lipore-ductor agent caffeine as a model molecule whose dynamics of loading and release from MIL-100(Fe) were already described in Cunha et col. *J. Mater. Chem. B*, 2013, 1, 1101.

Encapsulation of Caffeine. For the entrapment of caffeine inside the uncoated and acryl-PEG-coated MIL-100(Fe) nanoparticles, 10 mg of the dry nanoparticles were impregnated in 1 mL of a caffeine solution (20 mg·mL$^{-1}$) during 24 h under magnetic stirring at room temperature (note: nanoparticles are weighted wet based on the wet: dry ratio previously determined from nanoparticles dry at 100° C. overnight). Thereafter, caffeine-containing nanoparticles were collected by centrifugation (10500 rpm, 20 min) and washed once with 1 mL of fresh water.

Quantification of Caffeine and Trimesic Acid by High Performance Liquid Chromatography (HPLC). Release of the trimesic acid was monitored in a reversed phased HPLC system Waters Alliance E2695 separations module from Waters with a Sunfire-C18 reverse-phase column (5 μm, 4.6×150 mm from Waters) and equipped with a variable-wavelength photodiode array detector Waters 2998 and controlled by Empower software. The mobile phase used for the measurements consisted of mixture of 45% v/v methanol in PBS solution (0.04 M, pH 2.5). Injection volume was set at 10 μl, flow rate at 1 mL·min$^{-1}$ and temperature of the column at 25° C. The standards used for the calibration curve consisted of trimesic acid solutions at concentrations of: 25, 12.5, 6.25, 3.13, 1.56, 0.78, 0.39 mg·mL$^{-1}$. The calibration curve presented a good correlation coefficient ≥0.99. Chromatogram of standards showed a retention time for the organic linker of 4.6 with an absorption maximum at 215 nm. Degradation kinetics of the nanoparticle were obtained in water and PBS at 37° C. according to a previously reported procedure (Cunha et al.) and represented as the wt % of the linker released, considering the maximum of degradation of 100% when the total amount of the linker was released in the medium. Caffeine loading and release in water and PBS at 37° C. was determined by using the same HPLC system and measurement conditions. The caffeine solutions used as standards for the calibration curve were: 25, 12.5, 6.25, 3.13, 1.56, 0.78 and 0.39 μg·mL$^{-1}$. The calibration curve presented a good correlation coefficient ≥0.99. Chromatogram of standards showed a retention time for caffeine of 2.7 with an absorption maximum at 272 nm. The amount of caffeine entrapped inside the nanoparticles and delivered thereafter during incubation of nanoparticles in distilled water and PBS at 37° C. was determined by HPLC according to a previously reported procedure (Cunha et al). Data is represented as the wt % of the caffeine delivered in the medium, considering the maximum of delivery of 100% when the total amount of the caffeine initially encapsulated in the nanoparticles was released.

Figure 9:
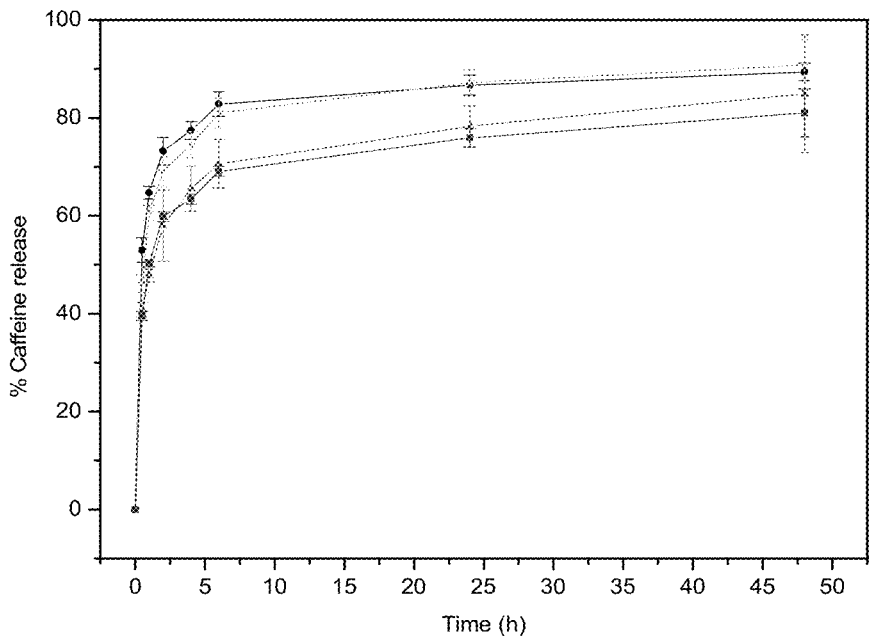
FIG. 9 represents the delivery of caffeine in (a) water and (b) PBS at 37° C. as a function of time for uncoated (red); acryl-$PEG_{480Da}$-coated (dark gray); acryl-$PEG_{2kDa}$-coated (black); and acryl-$PEG_{5kDa}$-coated (clear gray) MIL-100 (Fe) nanoparticles in (a) water and (b) PBS at 37° C. as a function of time. Delivery is represented as the wt % of the caffeine released in the medium, considering the maximum of 100% when the total amount of caffeine initially entrapped in the nanoparticle was released in the medium.
Figure 9:
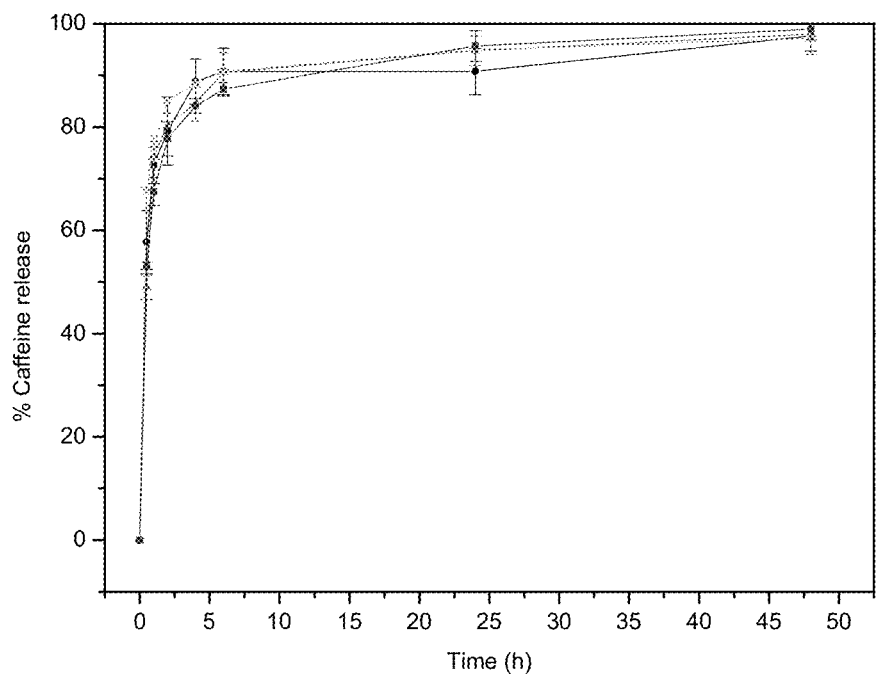

Results. Encapsulation of caffeine in both uncoated and PEG-coated equivalents was carried out by simple impregnation in a caffeine-containing aqueous solution for 24 h and the amount of entrapped caffeine was determined by HPLC and shown in Table 12. The payloads for the uncoated and PEG-coated nanoparticles was significantly the same regardless the surface coating, suggesting that the permeability of the coating allows caffeine moieties to diffuse through and accommodate inside the framework, and thus drug loading capacity of nanoMOFs was preserved. Similarly, no significant differences were observed in the cargo release in the two simulated physiological conditions, i.e. water and PBS at 37° C., suggesting no interaction of the caffeine with the polymeric coating (FIG. 9). For all the cases, the two typical stages of delivery of MIL-100(Fe) nanoparticles were observed, corresponding to: the first hour exhibiting an important caffeine release of 65±1 wt % in water and 73±4 wt % in PBS; and the second stage that covers until the completion of the 48 h that exhibit a more progressive delivery of the remaining caffeine. As previously assigned, the first stage could correspond to the release of the encapsulated entities located at the centre of the cages without interaction with the framework, whereas the second stage could be associated with the entities that intimately interact with the pore walls via van der Waals and $\pi$-$\pi$ stacking.

TABLE 11

Caffeine content in uncoated and PEG-coated MIL-100(Fe) nanoparticles.

| Sample | Caffeine content (% w/w) |
|---|---|
| Uncoated | 43 ± 2 |
| Acryl-PEG$_{480\ Da}$-coated | 48 ± 4 |
| Acryl-PEG$_{2\ kDa}$-coated | 41 ± 2 |
| Acryl-PEG$_{5\ kDa}$-coated | 39 ± 3 |

Example 10

Colloidal Stability of PEG-Coated MIL-100(Fe) Nanoparticles in Different Simulated Biological Media Preparation of Physiological Media. Note that all the media were prepared at double concentration considering a ½ dilution prior to the DLS measurement. Phosphate buffered saline (PBS) solution (pH=7.4, 0.01 M) were purchased from Sigma-Aldrich.

Colloidal stability tests. Particle size was monitored by Dynamic Light Scattering (DLS) on a Zetasizer Nano (Malvern Instruments). Diffusion speed of the aggregates in a solution due to Brownian motion is related to their size. The aggregation kinetics of MIL-100(Fe) nanoparticles was investigated by dispersing 1 mg of nanoparticles in 10 mL of the relevant medium (0.1 mg·mL$^{-1}$) using an ultrasound tip at 10% amplitude for 1 min (Digital Sonifer 450, Branson). This suspension was kept under stirring at 37° C., Nanoparticles were weighted out wet based on the wet: dry ratio previously determined from nanoparticles dried at 100° C. overnight. The stability of the nanoparticles was evaluated over a period of 24 h. In parallel experiments, the evolution of the particle surface charge was monitored by registering the ζ-potential of the colloidal solution at different times on a Zetasizer Nano instrument.

Results: In pure water (FIG. 10A), the colloidal solution of uncoated MIL-100(Fe) nanoparticles is stable up to 4 hours, whereas that of acryl-PEG$_{5kDa}$-coated MIL-100(Fe) nanoparticles is stable more than 24 h. High molecular weight PEG-coated MIL-100(Fe) nanoparticles are however more stable than the low molecular ones.

Figure 10:
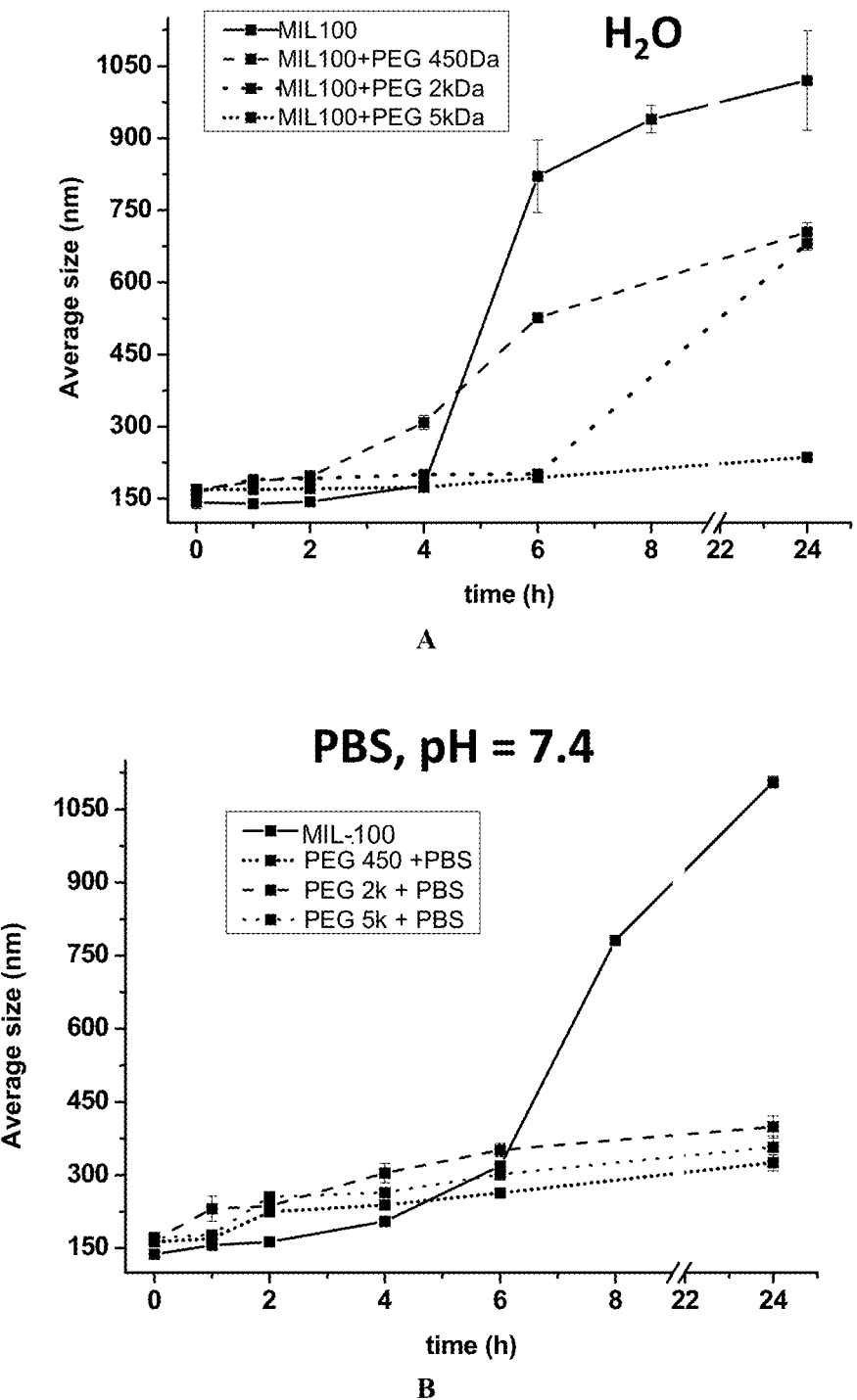
FIG. 10 represents the colloidal stability of acryl-$PEG_{480\,Da}$, acryl-$PEG_{2kDa}$ coated and acryl-$PEG_{5kDa}$-coated MIL-100(Fe) nanoparticles as well as the bare MIL-100(Fe) nanoparticles in pure water (A) and in PBS (B) as a function of time.

Similarly, PEG-coated nanoparticles are more stable in simulated physiological solution such as PBS (FIG. 10B). The colloidal solution of uncoated MIL-100(Fe) nanoparticles is stable under these conditions up to around 6 hours. In contrast, the colloidal solutions of PEG-coated MIL-100 (Fe) nanoparticles are much more stable (more than 24 hours, with small polydispersities index <0.3), regardless the molecular weight of the grafted PEG.

Example 11

Cytotoxicity Test of PEG-coated MIL-100(Fe) Nanoparticles

Cells and Culture: The J774 cell line (ATCC®TIB-67™) was maintained in RPMI 1640 medium supplemented with glutamax-1(Fisher 11554516) with 10% of heat-inactivated fetal bovine serum (FBS, Fisher 1157-3397) and 1% Penicillin/Streptomycin (Fisher 1154-8876), Cytotoxicity Assays: The cytotoxic activity of MIL-100 (Fe), acryl-PEG$_{2kDa}$-coated MIL-100(Fe) and acryl-PEG$_{5kDa}$-coated MIL-100(Fe) nanoparticles was analyzed by the MTT ((3-(4-5-Dimethylthiazol-2-yl)-2,5-diphenyltetrazolium bromide) assay. (T. Mosmann, *J. Immunol. Methods,* 1983, 65, 55; C. Tamames-Tabar, D. Cunha, E. Imbuluzqueta, F. Ragon, C. Serre, M. J. Blanco-Prieto, P. Horcajada, J. Mater. Chem. B, 2014, 2, 262) The cells were seeded 24 h prior to the assay in 96-well plates at a density of 1×10$^4$ cells per well in RPMI supplemented. The treatments were prepared at a 10-fold higher concentration (due to a direct 1/10 direct dilution in the well, as 20 of treatments were added to a final volume of 200 μL per well). They were added to the cells at different concentrations (in a range between 200 μg·mL$^{-1}$ until a final concentration of 1.0 mg·mL$^{-1}$) and kept during different times (1, 4, 8 and 24 h) at 37° C. with a 5% CO$_2$ atmosphere. The cytotoxicity was determined after 24 h by adding the MTT reactant (0.5 mg·mL$^{-1}$ in PBS, incubation at 37° C. during 2 h) followed by 200 μL of PBS washed, ending with 200 μL DMSO to each well. The plates were read the absorbance at λ=539 nm with a previous shaking program by the device.

Figure 11:
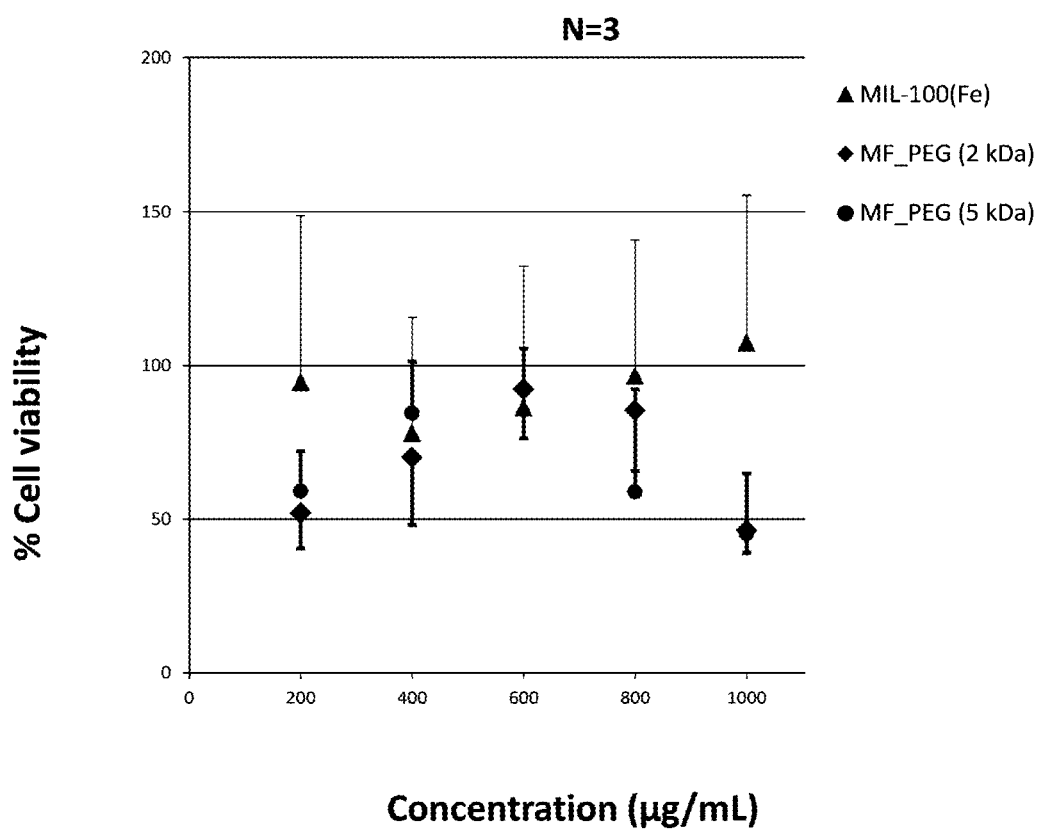
FIG. 11 represents the cell viability of J744A1 after 24 h in contact with uncoated or PEG-coated MIL-100(Fe) nanoparticles (acryl-$PEG_{2kDa}$ coated and acryl-$PEG_{5kDa}$-coated MIL-100(Fe) nanoparticles).

Results: PEG-coated MIL-100(Fe) nanoparticles showed a low cytotoxicity, with very important values of the inhibitory concentration 50 (IC$_{50}$) of around 1 mg·mL$^{-1}$ (FIG. 11). No significant differences were observed between both PEGylated nanoparticles, acryl-PEG$_{2kDa}$-coated MIL-100 (Fe) and acryl-PEG$_{5kDa}$-coated MIL-100(Fe). Similarly, the uncoated and the PEGylated MIL-100(Fe) exhibit a similar low in vitro toxicity.

Example 12

Complement Activation Assays of PEG-coated MIL-100(Fe) Nanoparticles

Complement Activation: Western blot with an anti-C3 antibody was carried out to analyze the degree of degradation of this factor upon Np addition. A pool of human sera from healthy donors was incubated with two different concentrations of MIL-100(Fe) and PEG-coated_MIL-100(Fe) nanoparticles (25 and 250 μg/mL). Zymosan (Zymosan A from *Saccharomyces cerevisiae,* Sigma Aldrich, CAS 58856-93-2), and PBS were used as positive and negative controls, respectively. Equal volumes of plasma, buffer and nanoparticles (50 μL each) were mixed together and incubated at 37° C. for 1 h. The mixture was centrifuged (16,000×g for 30 min) in order to separate the nanoparticles. Supernatants containing complement proteins were loaded (2 μL) onto a 10% SDS-PAGE gel and then transferred to a PVDF membrane (Immun-Blot, Bio-Rad; Hercules, Calif.) using the Transblot Semidry Transfer Equipment (Bio-Rad; Hercules, Calif.), PVDF membranes were blocked overnight at 4° C. with 5% non-fat dry milk in TBST. Then the membrane was washed and incubated for 90 min at RT with a mouse mAb against human C3 diluted 1:2000. After intensive washes, membranes were incubated with secondary polyclonal goat anti-mouse IgG Abs conjugated with alkaline phosphatase diluted 1:2000 at RT for 1 h. The membrane was finally revealed with BCIP (Bio-Rad Laboratories, Hercules, Calif.); facilities of University of Vigo (Moros, M., Hernaez, B., Garet, E., Dias, J. T., Saez, B., Grazu, V., Gonzalez-Fernandez, A., Alonso, C. and de la Fuente, J. M. *ACS Nano,* 2012, 6, 2, 1565-1577).

Results: The complement pathway is a key component of the innate immune system involved in the recognition and removal of foreign nanoparticles from the circulation to the reticule-endothelial system (RES). By avoiding their recognition, the blood circulation times of foreign nanoparticles can be significantly increased, thus modifying their in vivo fate. The ability of uncoated and PEG-coated nanoparticles to activate the complement pathway was evaluated through the quantification of the C3 factor coming from the degradation of complement protein using the western blot technique and detecting it with the anti-C3 antibody. (Lozano, T., Rey M., Rojas E., Moya S., Fleddermann J., Estrela-Lopis I., Donath D., Wang B., Mao Z., Gao C. And Gonzalez-Fernandez A. *J. Physics: Conference Series (JPCS),* 2011, 304, 012046; Dobrovolskaia, M. A. and Mcneil, S. E. *Natur. Nanotech.,* 2007, 2, 469-478).

Figure 12:
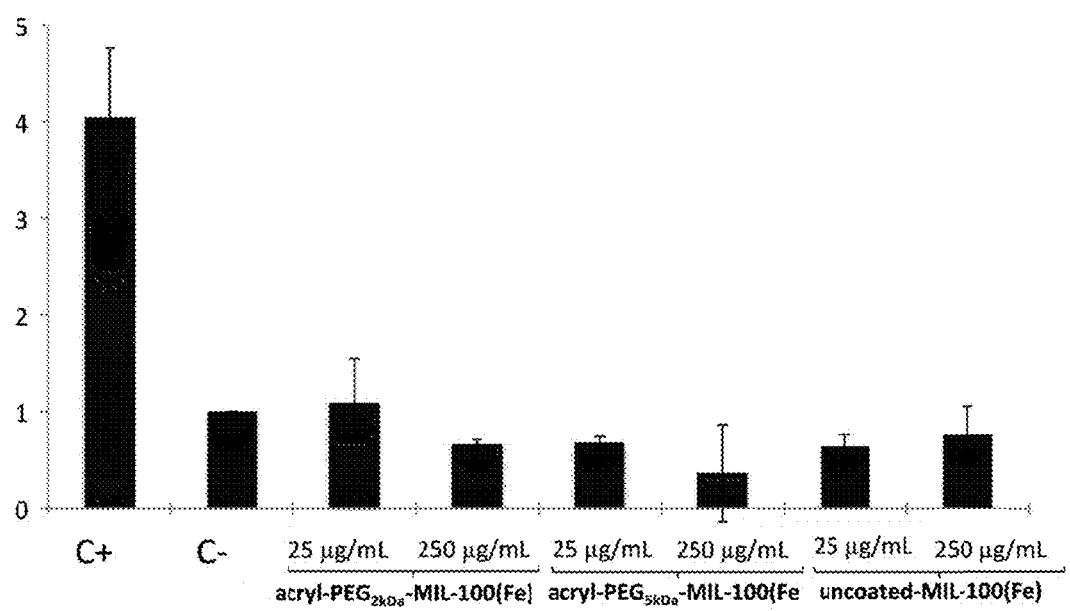
FIG. 12 represents the complement activation data for uncoated and PEG-coated MIL-100(Fe) nanoparticles (acryl-$PEG_{2kDa}$ coated and acryl-$PEG_{5kDa}$-coated MIL-100 (Fe) nanoparticles).

We have observed no induction of the complement activity for both uncoated and PEG coated MIL-100(Fe) nanoparticles (FIG. 12).

Example 13

Evaluation of the Cytokines Profile of PEG-Coated MIL-100(Fe) Nanoparticles

Cytokines profile evaluation: The cytokine production was evaluated with the kit FlowCytomix™ (Human Th1/Th2 11plex Ready-to-Use FlowCytomix Multiplex, eBioscience, Affimetrix), designed for a simultaneous quantification of several cytokines (IFN-δ, IL-1-β, IL-2, IL-4, IL-5, IL-6, IL-8, IL-10, IL-12 p70, TNF-α and TNF-β). The nanoparticle prototypes were tested at two different concentrations after 24 h of incubation with a pool of mononuclear cells (PBMs, obtained by limphoprep process using Ficull-Paque PLUS™ (GE Healthcare)); 25 and 250 μg/mL by flow cytometer (FC500, Beckman-Coulter; Miami, Fla.) at the CACTI facilities of the University of Vigo. PBMs were also incubated with, a lipopolysaccharide (LPS, 1 μg/mL) (InvivoGen; San Diego, Calif.) along with Lectin from *Phaseolus vulgaris* (red kidney bean, Sigma) (PHA, 1 μg/mL) and with PBS, which were used as positive and negative controls, respectively. (Lucarelli, M., Gatti, A. M., Savarino, G., Quattroni, P., Martinelli, L., Monari, E., Boraschi, D. *Eur. Cytokine Netw.*, 2004, 15, 4, 339-46).

Results: In complement to previous studies of the complement activation, the immune response induced by the nanoparticles was evaluated by the extracellular factors production, acting as humoral (Th2) or cellular (Thy1) signaling molecules involved in the immunomodulation.

The production of different humoral (IL-4, IL-5, IL-6, IL-10), cellular (IL-12p17 IFN-γ IL-2 TNF-β) or proinflammatory cytokines (IL-8, IL-1β, TNF-α) were investigated after the contact of either 25 or 250 µg/mL of uncoated MIL-100(Fe), acryl-PEG$_{2kDa}$ coated and acryl-PEG$_{5kDa}$-coated MIL-100(Fe) nanoparticles with a pool of mononuclear cells (PBMs).

While some cytokines, such as IL-4 and IL-5, are not produced neither by the uncoated nanoparticles nor the PEG-coated ones, the production of other extracellular factors such as TNF-α, IL-2 and IL-8 is significantly higher when the cells are in contact with both uncoated and coated-PEG MIL-100(Fe) nanoparticles. The production of the production of some interleukins (IL-1β, IL-10, IL-12p17, IL-1β, INF-γ and TNF-β) is significantly reduced when PEG-coated MIL-100(Fe) nanoparticles in comparison with the uncoated MIL-100(Fe) nanoparticles. One could then rationally expect a lower immune response of PEG-coated MIL-100(Fe) nanoparticles, making these nanoparticles more suitable for their use as drug nanocarriers.

TABLE 12

Human cytokines production (Th1/Th2 immune response) after 24 h in contact with MIL-100(Fe), acryl-PEG$_{2\ kDa}$ coated and acryl-PEG$_{5\ kDa}$-coated MIL-100(Fe) nanoparticles.

| | | Control | Uncoated | Acryl-PEG 2 kDa | Acryl-PEG 5 kDa |
|---|---|---|---|---|---|
| IL-12p70 | 25 µg/mL | 0 | >100 | — | <10 |
| | 250 µg/mL | | | | |
| IFN-γ | 25 µg/mL | 0 | >100 | >10 | >10 |
| | 250 µg/mL | | | — | <10 |
| IL-2 | 25 µg/mL | 0 | >10 | >10 | >10 |
| | 250 µg/mL | | | | |
| IL-10 | 25 µg/mL | 0 | >1 000 | >100 | >100 |
| | 250 µg/mL | | | | |
| IL-8 | 25 µg/mL | 5800 | <1 000 | <1 000 | <1 000 |
| | 250 µg/mL | | | >1 000 | |
| IL-6 | 25 µg/mL | 0 | >10 000 | >10 000 | >1 000 |
| | 250 µg/mL | | | >1 000 | >10 000 |
| IL-1β | 25 µg/mL | 0 | >1 000 | >100 | >100 |
| | 250 µg/mL | | | | |
| TNF-α | 25 µg/mL | 0 | >10 000 | >10 000 | >10 000 |
| | 250 µg/mL | | | | >1 000 |
| TNF-β | 25 µg/mL | 35 | <10 | — | <10 |
| | 250 µg/mL | | | | — |

Example 14

Formulation of the Graftfast PEGylated MIL-100(Fe) Nanoparticles as a Composite Patch Materials and Methods Gelatin from porcine skin (Gel) (300 g bloom, Mw≈90000); Poly-N-vinylpyrrolidone K30 (PVP) (Mw=50000-100000); polyvinylalcohol (Mw=18000); carboxymethylcellulose (CMC) (Mw=250 000) and Iron (III) chloride hexahydrate were purchased from Aldrich and used as received; methanol HPLC grade (Sigma-Aldrich); caffeine 98% (Alfa Aesar).

Preparation of the Patches
Preparation of the Drop-casted Patches

The casting solution was prepared with 20 mg of caffeine-containing graftfast-PEGylated MIL-100(Fe) nanoparticles dispersed on a 10 wt % PVP ethanol solution with an ultrasound tip (amplitude=10%, 30 sec). Final drop casting was performed immediately after particle dispersion pouring 1 mL over a Blenderm® film using a 2.0 mm×2.0 mm mold. The solvent was let evaporate overnight at room temperature.

Preparation of the Press-molding Patches 20 mg of the caffeine-containing graftfast-PEGylated MIL-100(Fe) nanoparticles and 50 mg of polymer (PVA or gelatin) were separately milled on a mortar, then mixed together and milled again. The resulting powder was readily put onto a 12 mm diameter-size wafer molded and pressed at 10 ton for 30 seconds.

The invention claimed is:

1. A process for preparing a porous solid with an outer surface modified by at least one polymer having no linear chain conformation; said at least one polymer being simultaneously synthesized in solution and grafted on the outer surface of said solid, comprising contacting:

a porous solid which is a Metal-Organic Framework (MOF) solid comprising a three-dimensional succession of units of formula (I):

$$M_mO_kX_lL_p$$

wherein:

M is a metal ion selected from the group consisting of $Fe^{2+}$, $Fe^{3+}$, $Zn^{2+}$, $Zn^{4+}$, $Ti^{4+}$, $Zr^{4+}$, $Ca^{2+}$, $Cu^{2+}$, $Gd^{3+}$, $Mn^{2+}$, $Mn^{3+}$, $Mg^{2+}$, $Ag^+$, $Si^{4+}$, and $Al^{3+}$;

m, k, l and p are numbers ≥0 chosen so as to respect the charge neutrality of the unit;

X is a ligand selected from the group consisting of OH, $Cl^-$, $F^-$, $I^-$, $Br^-$, $SO_4^{2-}$, $NO_3^-$, $ClO_4^-$, $R^1$—$(COO)_n^-$, $R^1$—$(SO_3)_n^-$, and $R^1$—$(PO_3)_n^-$, in which $R^1$ is a hydrogen atom, a linear or branched C1 to C8 alkyl, n=1 to 6; and L is a polyfunctionalized spacer ligand comprising a radical $R^0$ bearing q groups A, wherein:

q is a integer ranging from 2 to 6;

each occurrence of A is independently:

(i) a carboxylate

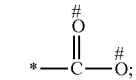

(ii) a phosphonate

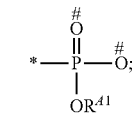

or (iii) an imidazolate

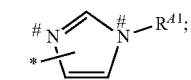

wherein $R^{41}$ is a hydrogen atom or a C1-C6 alkyl group;

wherein * denotes the point of attachment of the group A to the radical $R^0$;

wherein # denotes the possible points of attachment of the group A to the metal ion M;

$R^0$ represents:
(i) a C1-12 alkyl, C2-12 alkene or C2-12 alkyne radical;
(ii) a fused or non-fused monocyclic or polycyclic aryl radical, consisting of 6 to 50 carbon atoms; or
(iii) a fused or non-fused monocyclic or polycyclic heteroaryl, consisting of 4 to 50 carbon atoms;

the $R^0$ radical being optionally substituted by one or more groups independently chosen in the group consisting of OH, $NH_2$, $NO_2$ or a C1-C6 alkyl radical; and a polymer-precursor solution comprising an adhesion primer, and at least one radical polymerizable monomer;

under conditions enabling the formation of radical entities, and wherein said porous solid with an outer surface modified by at least one polymer having no linear chain conformation has no clogged pores after the implementation of said process so that encapsulation and release capacities of said porous solid are retained.

2. The process according to claim 1, wherein the conditions enabling the formation of radical entities comprise adding in the polymer-precursor solution, a reducing agent as a chemical activator.

3. The process according to claim 1, wherein the polymer-precursor solution comprises a solvent selected from the group consisting of water, acidified water, deionized water, acidified deionized water, distilled water, acidified distilled water, acetic acid, and hydroxylated solvents.

4. The process according to claim 1, wherein the adhesion primer is selected from cleavable aryl diazonium salts, aryl ammonium salts, aryl phosphonium salts and aryl sulfonium salts.

5. The process according to claim 1, wherein said adhesion primer is a cleavable diazonium salts of Formula (II)

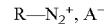

wherein,
$A^-$ represents a monovalent anion,
R represents an aryl group.

6. The process according to claim 1, wherein the polymer-precursor solution comprises a precursor of adhesion primer, said precursor of adhesion primer allowing in situ synthesis of adhesion primer before contacting with a porous solid.

7. The process according to claim 1, wherein the adhesion primer is a 4-nitrobenzene diazonium salt.

* * * * *